(12) United States Patent
Siciliano et al.

(10) Patent No.: US 10,732,177 B2
(45) Date of Patent: *Aug. 4, 2020

(54) METHODS AND COMPOSITIONS FOR DETECTING MULTIPLE ANALYTES WITH A SINGLE SIGNAL

(71) Applicant: Invisible Sentinel, Inc., Philadelphia, PA (US)

(72) Inventors: Nicholas Siciliano, Cherry Hill, NJ (US); Louis Leong, Junction City, NJ (US); Martin Patrick Keough, Lansdowne, PA (US); Ashley Shaniece Brown, Philadelphia, PA (US)

(73) Assignee: INVISIBLE SENTINEL, INC., Philadelphia, PA (US)

( * ) Notice: Subject to any disclaimer, the term of this patent is extended or adjusted under 35 U.S.C. 154(b) by 179 days.

This patent is subject to a terminal disclaimer.

(21) Appl. No.: 15/800,300

(22) Filed: Nov. 1, 2017

(65) Prior Publication Data

US 2018/0246085 A1 Aug. 30, 2018

Related U.S. Application Data

(63) Continuation of application No. 15/161,753, filed on May 23, 2016, now Pat. No. 9,823,240, which is a
(Continued)

(51) Int. Cl.
*G01N 33/543* (2006.01)
*C12Q 1/686* (2018.01)
*B01L 3/00* (2006.01)
*C12Q 1/6804* (2018.01)
*G01N 33/553* (2006.01)

(52) U.S. Cl.
CPC ...... *G01N 33/54306* (2013.01); *B01L 3/5023* (2013.01); *C12Q 1/6804* (2013.01); *C12Q 1/686* (2013.01); *G01N 33/543* (2013.01); *G01N 33/54353* (2013.01); *G01N 33/54366* (2013.01); *B01L 2300/069* (2013.01); *B01L 2300/0627* (2013.01); *G01N 33/553* (2013.01)

(58) Field of Classification Search
None
See application file for complete search history.

(56) References Cited

U.S. PATENT DOCUMENTS 3,581,227 A 5/1971 Podgorski
4,246,339 A 1/1981 Cole et al.
(Continued)

FOREIGN PATENT DOCUMENTS

AU 200025390 B2 7/2000
CA 2024458 A1 3/1991
(Continued)

OTHER PUBLICATIONS

Notice of Allowance dated Mar. 14, 2018 in U.S. Appl. No. 15/161,690.
(Continued)

*Primary Examiner* — Christopher L Chin
(74) *Attorney, Agent, or Firm* — Pepper Hamilton LLP

(57) ABSTRACT

Compositions, methods, and devices for the detection of multiple analytes with a single signal are provided.

20 Claims, 48 Drawing Sheets

Related U.S. Application Data continuation of application No. 13/789,002, filed on Mar. 7, 2013, now Pat. No. 9,347,938.

(60) Provisional application No. 61/608,774, filed on Mar. 9, 2012.

(56) References Cited

U.S. PATENT DOCUMENTS

| | | |
|---|---|---|
| 4,254,084 A | 3/1981 | Blum |
| 4,444,879 A | 4/1984 | Foster et al. |
| 4,446,232 A | 5/1984 | Liotta |
| 4,727,019 A | 2/1988 | Valkirs et al. |
| 4,797,260 A | 1/1989 | Parker |
| 4,828,801 A | 5/1989 | Lombardy wife Alric et al. |
| 4,920,046 A | 4/1990 | McFarland et al. |
| 4,976,926 A | 12/1990 | Matkovich |
| 4,994,240 A | 2/1991 | Hayashi |
| 5,003,988 A | 4/1991 | Guirguis |
| 5,133,363 A | 7/1992 | Guirguis |
| 5,137,691 A | 8/1992 | Parker |
| 5,141,850 A | 8/1992 | Cole et al. |
| 5,149,622 A | 9/1992 | Brown et al. |
| 5,155,022 A | 10/1992 | Naqui et al. |
| 5,155,049 A | 10/1992 | Kauvar et al. |
| 5,160,701 A | 11/1992 | Brown, III et al. |
| 5,166,054 A | 11/1992 | Naqui |
| 5,167,924 A | 12/1992 | Clark |
| 5,175,270 A | 12/1992 | Nilsen et al. |
| 5,185,127 A | 2/1993 | Vonk |
| 5,215,102 A | 6/1993 | Guirguis |
| 5,252,496 A | 10/1993 | Kang et al. |
| 5,296,347 A | 3/1994 | LaMotte, III |
| 5,358,690 A | 10/1994 | Guirguis |
| 5,451,504 A | 9/1995 | Fitzpatrick et al. |
| 5,474,902 A | 12/1995 | Uylen et al. |
| 5,541,069 A | 7/1996 | Mortensen et al. |
| 5,559,041 A | 9/1996 | Kang et al. |
| 5,620,657 A | 4/1997 | Sizto et al. |
| 5,622,871 A * | 4/1997 | May ................ G01N 33/54386 422/504 |
| 5,741,662 A | 4/1998 | Madsen et al. |
| 5,922,615 A | 7/1999 | Nowakowski et al. |
| 5,948,695 A | 9/1999 | Douglas et al. |
| 5,962,250 A | 10/1999 | Gavin et al. |
| 6,555,390 B2 | 4/2003 | Chandler |
| 6,716,641 B1 | 4/2004 | Sundrehagen |
| 6,766,817 B2 | 7/2004 | da Silva |
| 6,770,447 B2 | 8/2004 | Maynard et al. |
| 7,052,831 B2 | 5/2006 | Fletcher et al. |
| 7,205,159 B2 | 4/2007 | Cole et al. |
| RE39,664 E | 5/2007 | Gordon et al. |
| 7,285,255 B2 | 10/2007 | Kadlec et al. |
| 7,300,750 B2 | 11/2007 | Smart et al. |
| 7,377,904 B2 | 5/2008 | Conway et al. |
| 7,393,697 B2 | 7/2008 | Charlton |
| 7,435,577 B2 | 10/2008 | Lawrence et al. |
| 7,488,606 B2 | 2/2009 | Fleming et al. |
| 7,497,997 B2 | 3/2009 | Glezer et al. |
| 7,531,362 B2 | 5/2009 | Chan |
| 7,582,258 B2 | 9/2009 | Ruhl et al. |
| 7,638,093 B2 | 12/2009 | Wang et al. |
| 7,803,319 B2 | 9/2010 | Yang et al. |
| 7,815,854 B2 | 10/2010 | Cohen |
| 7,819,822 B2 | 10/2010 | Calasso et al. |
| 8,012,770 B2 | 9/2011 | Siciliano et al. |
| 8,183,059 B2 | 5/2012 | Siciliano et al. |
| 8,476,082 B2 | 7/2013 | Siciliano et al. |
| 9,341,624 B2 | 5/2016 | Siciliano et al. |
| 9,347,938 B2 * | 5/2016 | Siciliano ............. G01N 33/543 |
| 9,475,049 B2 | 10/2016 | Siciliano et al. |
| 9,557,330 B2 | 1/2017 | Siciliano et al. |
| 9,816,984 B2 | 11/2017 | Siciliano et al. |
| 9,823,240 B2 * | 11/2017 | Siciliano ............. G01N 33/543 |
| 10,018,626 B2 | 7/2018 | Siciliano et al. |
| 10,495,638 B2 | 12/2019 | Siciliano et al. |
| 2002/0115198 A1 | 8/2002 | Nerenberg et al. |
| 2002/0146346 A1 | 10/2002 | Konecke |
| 2002/0172937 A1 | 11/2002 | Dave et al. |
| 2002/0187561 A1 | 12/2002 | Wong et al. |
| 2003/0021727 A1 | 1/2003 | Weyker et al. |
| 2003/0073248 A1 | 4/2003 | Roth et al. |
| 2003/0207442 A1 | 11/2003 | Markovsky et al. |
| 2003/0207466 A1 | 11/2003 | Po Lee |
| 2004/0002063 A1 | 1/2004 | Chan et al. |
| 2004/0018576 A1 | 1/2004 | DeMatteo et al. |
| 2004/0214253 A1 | 10/2004 | Paek et al. |
| 2004/0256230 A1 | 12/2004 | Yager et al. |
| 2005/0069962 A1 | 3/2005 | Archer et al. |
| 2005/0124077 A1 | 6/2005 | Cole et al. |
| 2005/0130294 A1 | 6/2005 | Randall et al. |
| 2005/0163658 A1 | 7/2005 | Wang et al. |
| 2005/0191620 A1 | 9/2005 | McDevitt et al. |
| 2005/0277202 A1 | 12/2005 | Fleming et al. |
| 2006/0246435 A1 | 11/2006 | Kempin et al. |
| 2006/0257941 A1 | 11/2006 | McDevitt et al. |
| 2006/0275851 A1 | 12/2006 | Emmert-Buck et al. |
| 2007/0004003 A1 | 1/2007 | Kitamoto et al. |
| 2007/0009911 A1 | 1/2007 | Joo et al. |
| 2007/0020768 A1 | 1/2007 | Rundstrom et al. |
| 2007/0098601 A1 | 5/2007 | Mabuchi et al. |
| 2007/0166199 A1 | 7/2007 | Zhou et al. |
| 2007/0190667 A1 | 8/2007 | Cole et al. |
| 2007/0202542 A1 | 8/2007 | Babu et al. |
| 2007/0218500 A1 | 9/2007 | Mikoshiba et al. |
| 2007/0224701 A1 | 9/2007 | Rosenstein |
| 2007/0292941 A1 | 12/2007 | Handique et al. |
| 2008/0013949 A1 | 1/2008 | Yoshikane et al. |
| 2008/0019866 A1 | 1/2008 | Paek et al. |
| 2008/0199851 A1 | 8/2008 | Egan et al. |
| 2008/0318342 A1 | 12/2008 | Durack et al. |
| 2009/0104715 A1 | 4/2009 | Katada et al. |
| 2009/0108013 A1 | 4/2009 | Van Der Velde et al. |
| 2009/0140471 A1 | 6/2009 | Fletcher et al. |
| 2009/0148933 A1 | 6/2009 | Battrell et al. |
| 2009/0272974 A1 | 11/2009 | Park et al. |
| 2009/0311668 A1 | 12/2009 | Cheng |
| 2010/0009387 A1 | 1/2010 | Cheng |
| 2010/0034699 A1 | 2/2010 | Chan |
| 2010/0233028 A1 | 9/2010 | Iwasaki et al. |
| 2010/0261206 A1 | 10/2010 | Choi et al. |
| 2010/0322823 A1 | 12/2010 | Surapaneni et al. |
| 2010/0323369 A1 | 12/2010 | Marlborough et al. |
| 2011/0027908 A1 | 2/2011 | Siciliano et al. |
| 2011/0117673 A1 | 5/2011 | Johnson et al. |

FOREIGN PATENT DOCUMENTS

| | | |
|---|---|---|
| CA | 2037521 A1 | 11/1991 |
| CA | 2060216 A1 | 9/1992 |
| CA | 2353920 A1 | 7/2000 |
| CN | 1979164 A | 6/2007 |
| CN | 1989413 A | 6/2007 |
| CN | 101339190 A | 1/2009 |
| CN | 101655494 A | 2/2010 |
| CN | 101726594 A | 6/2010 |
| DE | 19859912 A1 | 7/2000 |
| EP | 0067921 A1 | 12/1982 |
| EP | 0246900 A1 | 11/1987 |
| EP | 0284232 A1 | 9/1988 |
| EP | 0310406 A2 | 4/1989 |
| EP | 0414513 A2 | 2/1991 |
| EP | 0456303 A2 | 11/1991 |
| EP | 0473065 A2 | 3/1992 |
| EP | 0505636 A1 | 9/1992 |
| EP | 1045248 A2 | 10/2000 |
| EP | 1901067 A2 | 3/2008 |
| EP | 2031393 A1 | 3/2009 |
| EP | 2072135 A1 | 6/2009 |
| GB | 1244321 A | 8/1971 |
| KR | 20020097364 A | 12/2002 |
| WO | 8204263 A1 | 12/1982 |
| WO | 8808534 A1 | 11/1988 |
| WO | 9112366 A1 | 8/1991 |

(56) References Cited

FOREIGN PATENT DOCUMENTS

| | | |
|---|---|---|
| WO | 9813519 A1 | 4/1998 |
| WO | 9836821 A1 | 8/1998 |
| WO | 0039581 A2 | 7/2000 |
| WO | 02059299 A2 | 8/2002 |
| WO | 02077013 A2 | 10/2002 |
| WO | 03016902 A1 | 2/2003 |
| WO | 2004097419 A1 | 11/2004 |
| WO | 2005091878 A2 | 10/2005 |
| WO | 2005119253 A1 | 12/2005 |
| WO | 2007097917 A1 | 8/2007 |
| WO | 2008154267 A2 | 12/2008 |
| WO | 2009034563 A2 | 3/2009 |
| WO | 2011014763 A1 | 2/2011 |
| WO | 2011044574 A1 | 4/2011 |

OTHER PUBLICATIONS

Fundamental Immunology, 3rd ed. (1993), ed. Paul, Raven Press, New York, N.Y.
Harlow et al., Antibodies: A Laboratory Manual, 1988, Cold Spring Harbor Laboratory Press, Cold Spring Harbor.
Jonio et al., Immunoglobulin Genes, 2nd Ed., 1995, Academic Press, San Diego.
Non-Final Office Action dated Jul. 6, 2015 from related U.S. Appl. No. 13/930,628.
Non-Final Office Action dated Nov. 3, 2015 from related U.S. Appl. No. 13/360,528.
Non-final Office Action dated Mar. 4, 2016 in U.S. Appl. No. 13/500,997.
Notice of Allowance dated Jan. 12, 2016 in related U.S. Appl. No. 13/930,628.
Notice of Allowance dated Mar. 16, 2016 for U.S. Appl. No. 13/789,002.
Notice of Allowance dated Jun. 10, 2016 in U.S. Appl. No. 13/360,528.
Office Action dated Apr. 4, 2017 in U.S. Appl. No. 15/161,753.
Office Action dated Apr. 12, 2017 in U.S. Appl. No. 15/141,141.
Notice of Allowance dated Jul. 25, 2017 in U.S. Appl. No. 15/161,753.
Notice of Allowance dated Jul. 27, 2017 in U.S. Appl. No. 15/141,141.
Notice of Allowance dated Jul. 15, 2019 in U.S. Appl. No. 15/383,330.
Non-Final Office Action dated Oct. 21, 2019 from related U.S. Appl. No. 15/290,965.
Notice of Related Applications currently filed herewith.

\* cited by examiner

Figure 12
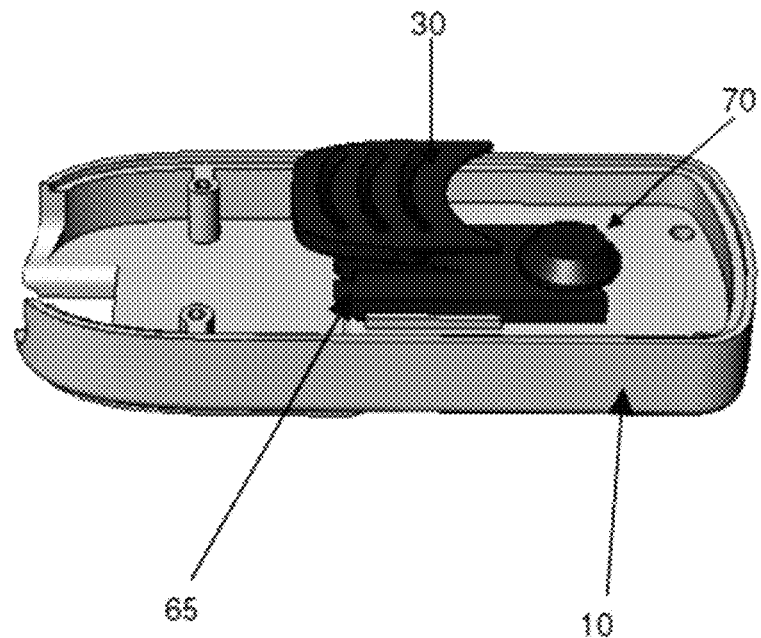
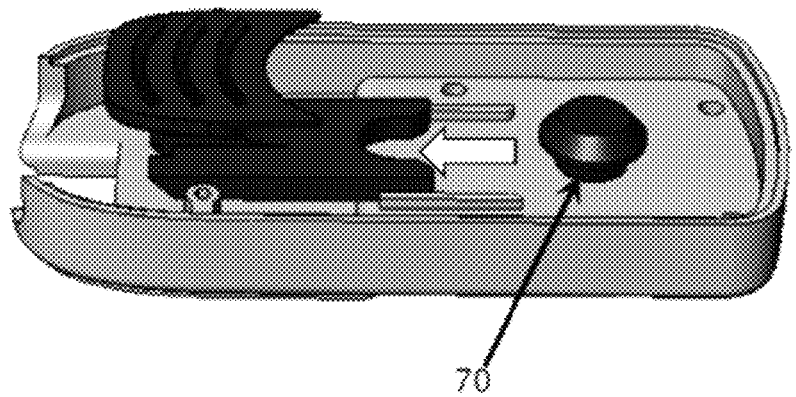
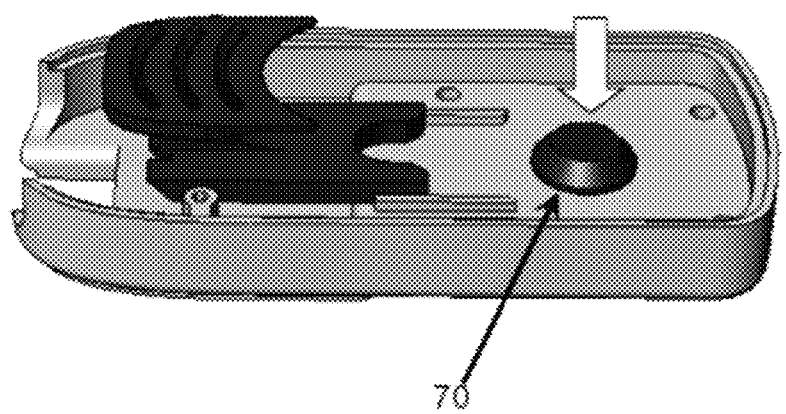

Figure 33
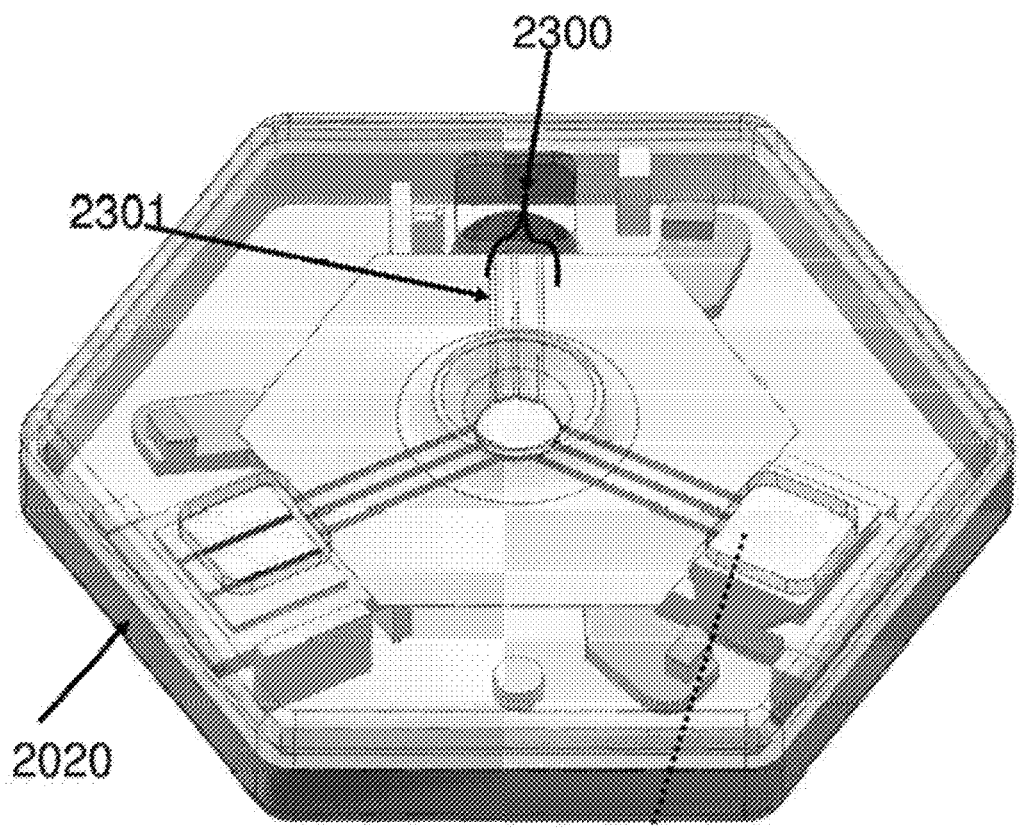
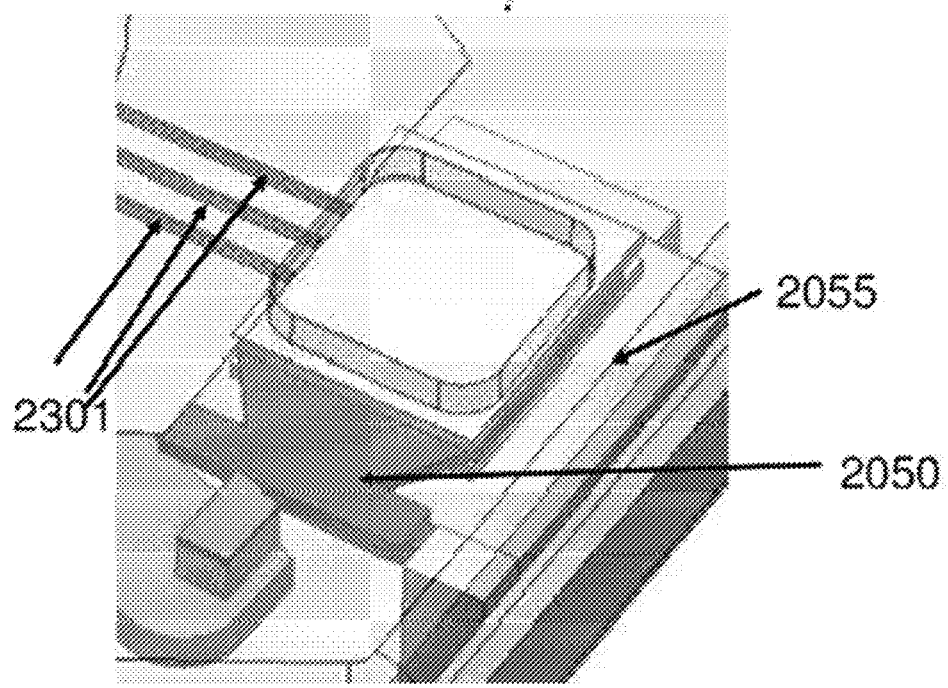

METHODS AND COMPOSITIONS FOR DETECTING MULTIPLE ANALYTES WITH A SINGLE SIGNAL

CROSS-REFERENCE TO RELATED APPLICATIONS

This application is a continuation of U.S. application Ser. No. 15/161,753, filed May 23, 2016, now issued as U.S. Pat. No. 9,823,240, which is a continuation of U.S. application Ser. No. 13/789,002, filed Mar. 7, 2013, now issued as U.S. Pat. No. 9,347,938, which claims priority to U.S. Provisional Application No. 61/608,774, filed Mar. 9, 2012, each of which is hereby incorporated by reference in its entirety.

FIELD OF INVENTION

Embodiments are directed to, in part, the detection of multiple analytes with a single signal.

BACKGROUND OF INVENTION

The detection of multiple analytes often requires the use of multiple signals or multiple reactions, spots, or wells to determine if a sample has multiple analytes. This can complicate interpretation and, in cases where an adulterant is classified as having two or more detectable characteristics, can make identification challenging for the end-user. Thus, to simplify and provide a consolidated qualitative report to the end-user, there is a need for methods and compositions that enable the detection of multiple analytes in a sample with a single signal. The present invention satisfies this need and others.

SUMMARY OF THE INVENTION

The present invention provides methods of concurrently detecting a first analyte and a second analyte comprising: contacting a solid support with a first analyte, a second analyte, a bridge unit comprising a second capture reagent, and a signal detection unit comprising a third capture reagent; and detecting the presence or absence of the signal detection unit which indicates the presence or absence of the first analyte and second analyte concurrently, wherein: a first capture reagent is affixed to the solid support; the first analyte comprises a first interaction unit that binds to the first capture reagent and a second interaction unit that binds to the bridge unit; and the second analyte comprises a first interaction unit that binds the bridge unit and a second interaction unit that binds to the signal detection unit.

The present invention also provides methods of concurrently detecting a first analyte, a second analyte, and a third analyte with a single signal comprising: contacting the first, second, and third analytes with a solid support, a first bridge unit, a second bridge unit, and a signal detection unit; and detecting the presence of the signal detection unit which indicates the presence of the first, second, and third analytes concurrently with a single signal, wherein: the first analyte comprises a first interaction unit and a second interaction unit; the second analyte comprises a first interaction unit and a second interaction unit; the third analyte comprises a first interaction unit and a second interaction unit; the solid support comprises a first capture reagent that binds to the first interaction unit of the first analyte; the first bridge unit binds to the second interaction unit of the first analyte and the first interaction unit of the second analyte; the second bridge unit binds to the second interaction unit of the second analyte and the first interaction unit of the third analyte; and the signal detection unit binds to the second interaction unit of the third analyte. The interaction units can be different from one another on each of the analytes.

In some embodiments, methods of concurrently detecting a first analyte and a second analyte are provided, the method comprising: contacting a solid support with a first analyte of interest, a second analyte of interest, a bridge unit comprising a second capture reagent, and a signal detection unit comprising a third capture reagent; and detecting the presence or absence of the signal detection unit which indicates the presence or absence of the first analyte of interest and second analyte of interest concurrently, wherein: a first capture reagent is affixed to the solid support; the first analyte of interest comprises a first interaction unit that binds to the first capture reagent and a second interaction unit that binds to the bridge unit; and the second analyte of interest comprises a first interaction unit that binds the bridge unit; a signal detection unit that binds to the second analyte, to the second analyte's first interaction unit or a second interaction unit, to a component of the first and second analyte complex or bridge unit that that is only present when the complex contains the first and second analyte.

Embodiments described herein also provide complexes comprising a solid support, a first analyte, a second analyte, a bridge unit, and a signal detection unit wherein each member of the complex binds to each other directly or indirectly.

Embodiments described herein also provide complexes comprising a solid support, a first analyte, a second analyte, a third analyte, a first bridge unit, a second bridge unit, and a signal detection unit, wherein the solid support, first analyte, second analyte, third analyte, first bridge unit, second bridge unit, and signal detection unit are bound to each other directly or indirectly.

Methods of concurrently detecting a first analyte of interest and a second analyte of interest are provided herein. In some embodiments, the method comprises contacting a solid support with a first analyte of interest, a second analyte of interest, a bridge unit comprising a second capture reagent, and a signal detection unit comprising a third capture reagent; and detecting the presence or absence of the signal detection unit which indicates the presence or absence of the first analyte of interest and second analyte of interest concurrently, wherein a first capture reagent is affixed to the solid support; the first analyte of interest comprises a first interaction unit that binds to the first capture reagent and a second interaction unit that binds to the bridge unit; and the second analyte of interest comprises a first interaction unit and a second interaction unit, wherein the first interaction unit binds the bridge unit; a signal detection unit that binds to: i) the second analyte, ii) to the second analyte's first interaction unit or second interaction unit, iii) to a component of the first and second analyte complex, or iv) a component of an analyte-bridge complex that is only present when the complex contains the first and second analytes.

In some embodiments, the first and second interaction unit of the first analyte of interest and the first and second interaction unit of the second analyte of interest are each, independently, a heterologous interaction unit. In some embodiments, the second interaction unit of the first analyte of interest and the first interaction unit of the second analyte of interest comprise the same heterologous interaction unit. In some embodiments, the second interaction unit of the first analyte of interest and the first interaction unit of the second analyte of interest comprise different heterologous interaction units. In some embodiments, the first interaction unit of the first analyte of interest and the second interaction unit of the second analyte of interest comprise the same heterologous interaction unit. In some embodiments, the first interaction unit of the first analyte of interest and the second interaction unit of the second analyte of interest comprise different heterologous interaction units.

Methods of concurrently detecting a first analyte of interest, a second analyte of interest, and a third analyte of interest with a single signal are provided. In some embodiments, the method comprises contacting the first, second, and third analytes of interest with a solid support, a first bridge unit, a second bridge unit, and a signal detection unit; and detecting the presence of the signal detection unit which indicates the presence of the first, second, and third analytes of interest concurrently with a single signal, wherein: the first analyte of interest comprises a first interaction unit and a second interaction unit; the second analyte of interest comprises a first interaction unit and a second interaction unit; the third analyte of interest comprises a first interaction unit and a fifth interaction unit; the solid support comprises a first capture reagent that binds to the first interaction unit of the first analyte of interest; the first bridge unit binds to the second interaction unit of the first analyte of interest and the first interaction unit of the second analyte of interest; the second bridge unit binds to the second interaction unit of the second analyte of interest and the first interaction unit of the third analyte of interest; and the signal detection unit binds to: i) the third analyte, ii) to the third analyte's first interaction unit or second interaction unit, iii) to a component of the first, second, or third analyte complex, or iv) a component of an analyte-bridge complex that is only present when the complex contains the first, second, and third analytes.

In some embodiment, the bridge units described herein are multivalent capture reagents. In some embodiments, the multivalent capture reagent is an immunoglobulin. In some embodiments, the immunoglobulin is IgM. The bridge unit can also be biotin.

Methods of concurrently detecting a plurality of analytes with a single signal with a device are provided. In some embodiments, the method comprises a) contacting a device for detecting a plurality of analytes with a single signal with one or more samples comprising a plurality of analytes, wherein the device comprises: a housing comprising: an inlet opening in fluid contact with a conjugate pad; a force member; a slidable locking member contacting the force member; an attachment member contacting the force member; a sliding button contacting the attachment member; and a detection membrane system comprising the conjugate pad, a test membrane, and an absorbent member, at least a portion of the conjugate pad, test membrane, and absorbent member are substantially parallel to each other, the force member contacts the detection membrane system and is capable of applying pressure substantially perpendicular to the detection membrane system, the sliding button moves the slidable locking member, the conjugate pad comprises a signal detection unit comprising a third capture reagent; the test membrane comprises a first capture reagent affixed to the test membrane; wherein the one or more samples comprises a first analyte of interest, a second analyte of interest, and a bridge unit comprising a second capture reagent, wherein the first analyte of interest comprises a first interaction unit that binds to the first capture reagent and a second interaction unit that binds to the bridge unit, and the second analyte of interest comprises a first interaction unit that binds the bridge unit and a second interaction unit; wherein the signal detection unit comprising the third capture reagent binds to: i) the second analyte, ii) to the second analyte's first interaction unit or second interaction unit, iii) to a component of the first and second analyte complex, or iv) a component of an analyte-bridge complex that is only present when the complex contains the first and second analytes; and b) detecting the presence or absence of the signal detection unit which indicates the presence or absence of the first analyte of interest and second analyte of interest concurrently.

In some embodiments, the method comprises moving the conjugate pad after a portion of the one or more samples has contacted and flowed through the conjugate pad, thereby exposing at least a portion of the test membrane for detection of the signal detection unit to indicate the presence or absence of the plurality of analytes with a single signal. In some embodiments, the conjugate pad is moved by moving the slidable locking member. In some embodiments, the first and second analyte are amplicons. In some embodiments, the first and second analytes are PCR reaction products. In some embodiments, the first analyte's first interaction unit is a digoxigenin label. In some embodiments, the first analyte's second interaction unit is a rhodamine label. In some embodiments, the second analyte's first interaction unit is a rhodamine label. In some embodiments, the second analyte's second interaction unit is a fluorescein label. In some embodiments, the third capture reagent binds to the second analyte's second interaction unit. In some embodiments, the third capture reagent is a biotinylated capture reagent. In some embodiments, the signal interaction unit is coated with streptavidin. In some embodiments, the signal interaction unit is streptavidin coated colloidal gold. In some embodiments, the first and second analytes are nucleic acid amplification products, wherein: the first analyte comprises a digoxigenin label and a rhodamine label; the second analyte comprises a rhodamine label and a fluorescein label; the first capture reagent is an anti-digoxigenin label antibody; the second capture reagent is an anti-rhodamine label antibody; the third capture reagent is a biotinylated anti-fluorescein label antibody; and the signal interaction unit is streptavidin coated colloidal gold.

BRIEF DESCRIPTION OF THE DRAWINGS

FIG. 12 depicts some components of a representative device in various positions according to some embodiments of the present invention.

FIG. 33 depicts an interior view of a representative device according to some embodiments of the present invention.

DESCRIPTION OF EMBODIMENTS

Figure 1:
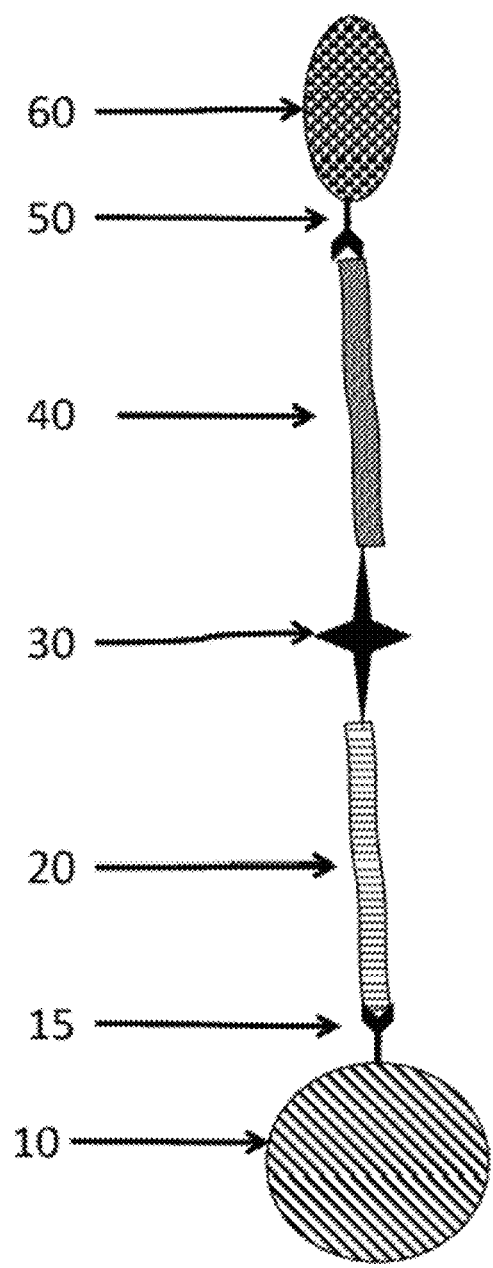
FIG. 1 illustrates, among other aspects, the representative detection of two analytes with a single signal.

Before compositions and methods provided herein are described, it is to be understood that the embodiments are not limited to the particular processes, compositions, or methodologies described, as these may vary. It is also to be understood that the terminology used in the description is for the purpose of describing some embodiments, and is not intended to limit the scope of the embodiments.

Various methods and embodiments are described herein. The methods and embodiments can be combined with one another. The definitions and embodiments described herein are not limited to a particular method or example unless the context clearly indicates that it should be so limited.

As used herein, the phrase "detection of an analyte," "detecting an analyte" refers the detection of multiple analytes with a single signal. The detection of multiple analytes can be, as described herein, at least, or exactly, 2, 3, 4, or 5 analytes with a single signal.

It must be noted that, as used herein and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications mentioned herein are incorporated by reference in their entirety to the extent to support the presently described subject matter. Nothing herein is to be construed as an admission that the subject matter is not entitled to antedate such disclosure by virtue of prior invention.

As used herein, the term "about" means plus or minus 10% of the numerical value of the number with which it is being used. Therefore, about 50% means in the range of 45%-55%. Additionally, in phrase "about X to Y," is the same as "about X to about Y," that is the term "about" modifies both "X" and "Y."

As used herein, the term "optional" or "optionally" means that the subsequently described structure, event or circumstance may or may not occur, and that the description includes instances where the event occurs and instances where it does not.

As used herein, the term "sample" means any fluid medium or liquid that may contains a particular item (e.g. analyte) or suspected of containing a particular item. In some embodiments, samples may be used which are high in dissolved solids without further processing, and samples containing high solids (non-dissolved) may be analyzed, in some embodiments, through the use of a filter or used in conjunction with additional manual steps. Samples may also be non-filtered or purified prior to being used in a method or device described herein. Samples may be a liquid, a suspension, extracted or dissolved sample, or a supercritical fluid. If a sample is going to be used in a flow device (vertical or lateral) some flow properties must exist in the sample or extract to allow flow through the devices and systems described herein. Examples of samples include, but are not limited to, blood, food swabs, food extracts, food suspensions, food cultures, bacterial cultures, viral cultures, amplification reactions, saliva, biological fluid, PCR reactions, and the like. The sample can also be derived from a another sample. For example, a PCR reaction can be performed on a nucleic acid mixture that has been extracted, isolated, and/or purified from another sample (e.g., food, cellular, viral, bacterial, blood, and the like). The PCR reaction would be considered to be a sample derived from another sample.

A "food suspension" refers to raw or cooked food that has been placed or suspended in a solution. The food solution may be mixed, vortexed or blended. A "food culture" is a food sample that is cultured under conditions to enrich the sample. This process can also be referred to as "enrichment." The enrichment can be used to facilitate sample analysis to better detect the presence or absence of multiple analytes with a single signal. The sample can also be a reaction sample that is derived from a different sample. An example of a reaction sample is an "enrichment." For example, a blood or food sample may be processed (e.g. cultured, purified, separated into components, and the like) and the processed sample can be tested for the detection of multiple analytes. In some embodiments, two analytes are detected in a blood sample or a food sample. In some embodiments, the analytes can be detected by performing two amplification reactions that are specific for the two analytes and then the two amplification products can be detected with a single signal to detect the presence of the two analytes in a sample concurrently. In some embodiments, three analytes are detected using a single signal. The detection can be concurrent, that is the signal is only generated when all the analytes are present in the same sample. The concurrent signal generation can be effectuated through the creation of a bridging complex, which is described herein. Non-limiting embodiments of the bridging complex can be seen in FIGS. 1-3.

As used herein, the term "solid support" means a material that is substantially insoluble in a selected system, or which can be readily separated (e.g., by precipitation) from a selected system in which it is present. Solid supports useful in practicing the present methods can include groups that are activated or capable of activation to allow certain compounds or molecules (e.g. capture reagents, antibodies, and the like) to be bound to the solid support. The solid support may, for example, be agarose, sepharose, polyacrylamide, agarose/polyacrylamide co-polymers, dextran, cellulose, polypropylene, polycarbonate, nitrocellulose, glass paper, or any other suitable substance capable of providing a suitable solid support. In some embodiments, the solid support may be in the form of granules, a powder or a gel suitable for use in chromatography. The solid support can also be a membrane, such a nitrocellulose, PVC, and the like. Other types of membranes can also be used and there is no specific requirement for the type of membrane that can be used. In some embodiments, the solid support is a test membrane. Examples of test membranes are described herein.

As used herein, the term "analyte" includes, but is not limited to, antigens, nucleic acid molecules encoded by a cell, virus, bacteria or other type of microorganism, amplification products (e.g. amplicons), a peptide, a sugar, and the like. In some embodiments, the analyte is not an antibody or functional fragment thereof. Nucleic acid molecules can be detected as described herein by using the methods described herein in combination with other known methods or devices, such as amplification methods (e.g. PCR, RT-PCR, and the like), hybridization methods, labeled primers, and the like. The term "target molecule" can be used interchangeably with the term "analyte." The amplification methods can be used to amplify the amount of nucleic acid molecules present in a sample to facilitate the detection of the analyte. Other types of analytes that can be detected using the methods described herein include, but are not limited to antigens, antibodies, receptors, ligands, chelates, proteins, enzymes, nucleic acids, DNA, RNA, pesticides, herbicides, inorganic or organic compounds, or any material for which a specific binding reagent may be found. The analyte can also refer to different epitopes present on the same protein or polypeptide. The analyte can also refer to analytes from pathogenic or non-pathogenic organisms. The analytes can also be referred to as an analyte of interest in a sample. That is, the analyte can be referred to as an agent that a user is determining the presence or absence of in a sample.

As discussed herein, the analyte can be an amplification product, such as a product of a PCR reaction. The PCR product is amplifying a nucleic acid sequence from a test sample. Thus, detection of the PCR product in sample is determining whether the nucleic acid sequence that the PCR product is based upon is present in the initial sample. For example, if one of skill in the art is determining whether a food sample is contaminated with *E. Coli*, nucleic acid sequences that are specific for *E. Coli* can be amplified (e.g. by PCR) and then detected according to the methods described herein. The detection of the amplification products (i.e. amplicons) indicates that the food sample contained the native nucleic acid sequences that are specific for *E. Coli*. This is example is non-limiting and can be applied to detecting other nucleic acid sequence or other types of analytes present in a native sample. The analyte can be what is in the initial sample or an analyte that is derived from the initial sample by, for example, using PCR. When the plurality of analytes is being detected with a single signal according to the methods provided herein, the analytes can also have heterologous tags or interaction units, and the modified analyte is also referred to as the analyte. In some embodiments, the analyte will be free of heterologous interaction units, such as fluorescent tags, biotin, digoxigenin, and the like.

Figure 2:
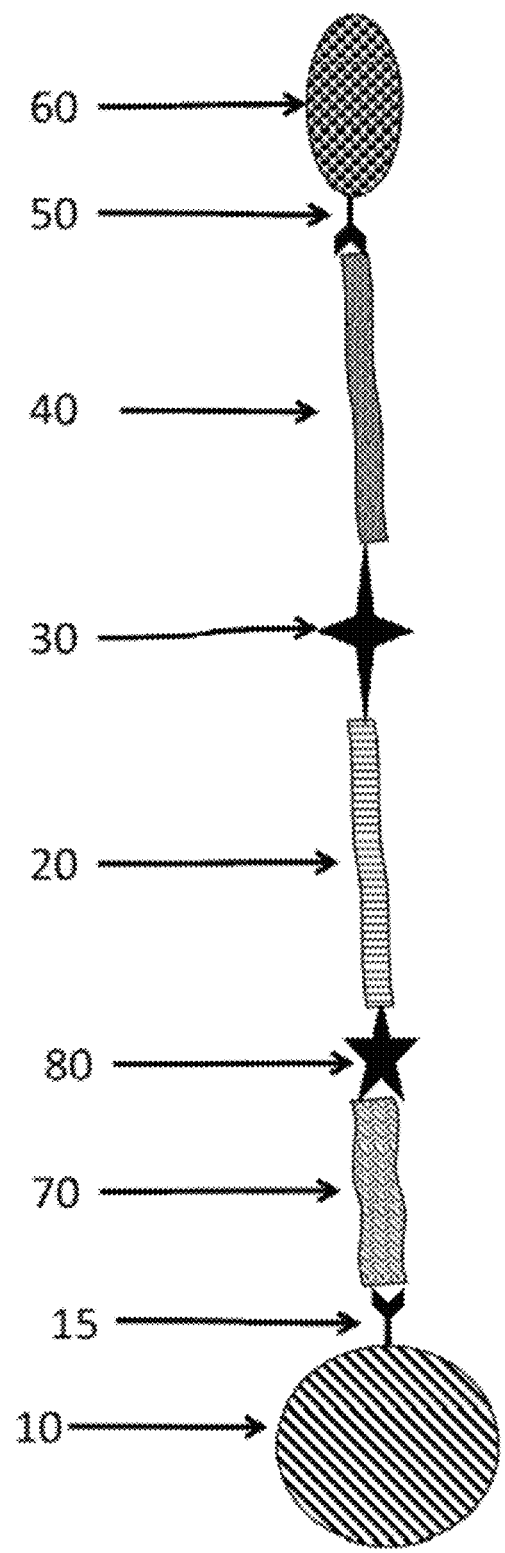
FIG. 2 illustrates, among other aspects, the representative detection of three analytes with a single signal.

An analyte is different from a reagent that is used to detect the presence or absence of an analyte. Thus, a reagent that is added to the sample to determine if the analyte is present is not an analyte of interest. For example, in a typical sandwich assay, a first antibody is attached to a solid support. The solid support coated with an antibody is contacted with a sample to determine the presence or absence of an antigen that binds to the antibody. A secondary antibody is then also added to detect the antigen. The presence of the secondary antibody is then often detected by the addition of a third antibody that has, for example. an enzyme conjugated to it so that it can be detected through various means (e.g. HRP-linked antibodies). The secondary antibody is not an analyte of interest because it is a reagent used to detect the primary antigen. Therefore, a sandwich assay does not detect the presence of a plurality of analytes with a single signal according to the methods described herein because the secondary antibody is a reagent, or tool, to detect the presence or absence of the antigen, or an analyte of interest. An analyte is also not a component or portion that is found on a bridging entity. For example, in U.S. Published Application No. 2010/0273145 FIGS. 1 and 2 show an analyte binding to a bridging entity, which then binds to a signaling entity to detect the presence of the analyte. Neither the bridging unit, or any portion thereof, or the signaling entity is an analyte or analyte of interest. These components are reagents used to detect the analyte, which in the case of U.S. Published Application No. 2010/0273145 is the detection of a single analyte. U.S. Published Application No. 2010/0273145 is hereby incorporated by reference with regards to its figures and the explanation of their components.

In some embodiments, the analyte is a protein, such as a pathogen protein. A pathogen protein refers to a protein that is from a pathogen. Examples of pathogens include, but are not limited to, viruses, prokaryotes and, for example, pathogenic eukaryotic organisms such as unicellular pathogenic organisms and multicellular parasites. Pathogens also can include protozoan pathogens which include a stage in the life cycle where they are intracellular pathogens. As used herein, the term "intracellular pathogen" means a virus or pathogenic organism that, at least part of its reproductive or life cycle, exists within a host cell and therein produces or causes to be produced, pathogen proteins. A pathogen can also be a food-borne pathogen.

Bacterial pathogens include, but are not limited to, such as bacterial pathogenic gram-positive cocci, which include but are not limited to: pneumococcal, staphylococcal, and streptococcal. Pathogenic gram-negative cocci include, but are not limited to: meningococcal and gonococcal. Pathogenic enteric gram-negative bacilli include, but are not limited to: enterobacteriaceae, *pseudomonas*, acinetobacteria, eikenella, melioidosis, *salmonella*, shigellosis, hemophilus, chancroid, brucellosis, tularemia, *yersinia* (*pasteurella*), *streptobacillus moniliformis*, spirilum, *Listeria monocytogenes*, Erysipelothrix rhusiopathiae, diphtheria, cholera, anthrax, donovanosis (granuloma inguinale), and bartonellosis. Pathogenic anaerobic bacteria include, but are not limited to, those that are responsible for: tetanus, botulism, other clostridia, tuberculosis, leprosy, and other mycobacteria. Pathogenic spirochetal diseases include, but are not limited to: syphilis, treponematoses, yaws, pinta and endemic syphilis, and leptospirosis. Other infections caused by higher pathogen bacteria and pathogenic fungi include, but are not limited to: actinomycosis, nocardiosis, cryptococcosis, blastomycosis, histoplasmosis, and coccidioidomycosis, candidiasis, aspergillosis, mucormycosis, sporotrichosis, paracoccidiodomycosis, petriellidiosis, torulopsosis, mycetoma, chromomycosis, and dermatophytosis. Rickettsial infections include, but are not limited to, *rickettsia* and rickettsioses. Examples of mycoplasma and chlamydial infections include, but are not limited to: mycoplasma cpneumonia, lymphogranuloma venereum, psittacosis, and perinatal chlamydial infections. Pathogenic protozoans and helminths and infectious eukaryotes thereby include, but are not limited to: amebiasis, malaria, leishmaniasis, trypanosomiasis, toxoplasmosis, *Pneumocystis carinii*, babesiosis giardiasis trichinosis filariasis schistosomiasis, nematodes, trematodes or flukes, and cestode (tapeworm) infections. Bacteria also include, but are not limited to, *Listeria, E. coli, Campylobacter species*, and *Salmonella* species. In some embodiments, *E. coli* is *E. coli* 0157.

Examples of viruses include, but are not limited to, HIV, Hepatitis A, B, and C, FIV, lentiviruses, pestiviruses, West Nile Virus, measles, smallpox, cowpox, ebola, coronavirus, and the like. Other pathogens are also disclosed in U.S. Patent Application Publication No. 20080139494, which are incorporated herein by reference.

In some embodiments, the pathogen is a food borne pathogen. The analyte can be present on a food borne pathogen. Food borne pathogens are pathogens (e.g. viral or bacterial) that cause illness after eating contaminated food. The food itself does not directly cause the illness, but it is rather the consumption of the food borne pathogen that is present on the food that causes the illness. In some embodiments, the food borne pathogen is *E. coli, Listeria*, a *Campylobacter* species, or a *Salmonella* species. In some embodiments, the analyte is chosen from a food borne pathogen analyte. For example, the food borne pathogen analyte can be, but is not limited to, chosen from an *E. coli* analyte, a *Listeria* analyte, a *Campylobacter* species analyte, or a *Salmonella* species analyte. In some embodiments, the analyte is the specific 0-Antigen. In some embodiments, the O-antigen is the *E. coli* antigen and/or a *Salmonella* species 0-antigen and can be used for *E. coli* and *Salmonella* detection. In some embodiments, the analyte is a flagellin antigen. In some embodiments, the analyte is the *Campylobacter* flagellin antigen. In some embodiments the analyte is a virulence factor gene such as the Shiga toxin gene amplified from pathogenic *E. coli* or *Salmonella*. In some embodiments, the analyte is a DNA or RNA sequence that is amplified via an amplification method (e.g. PCR or RT-PCR) and then detected according to the methods described herein.

As described herein, an analyte can be an amplification product. The amplification product, such as PCR product (e.g. a double stranded PCR product), can be labeled with interaction units. The production of a labeled amplification product with the units can be made by the use of primers labeled or conjugated with the two interaction units. In some embodiments, an analyte will have two different interaction units so that the bridging complex can be assembled and the detection of multiple analytes is possible through a signal detection unit.

As used herein, the term "signal detection unit" means a unit that can be detected to determine if the analyte or analytes are present in a sample. The signal detection unit can be any reagent or composition that can be detected. In some embodiments, the signal detection unit is attached to a capture reagent. Thus, the signal detection unit can be used to detect the presence of the capture reagent binding to its specific binding partner. The capture reagent can comprise a detection reagent directly or the capture reagent can further comprise a particle that comprises the detection reagent. In some embodiments, the capture reagent and/or particle comprises a color, colloidal gold, a radioactive tag, a fluorescent tag, or a chemiluminescent substrate. In some embodiments, the signal detection unit comprises a near-infrared or infrared tag or substrate. In some embodiments, the signal detection unit comprises a color, colloidal gold, a radioactive tag, a fluorescent tag, or a chemiluminescent substrate. In some embodiments, the signal detection unit comprises a nanocrystal, functionalized nanoparticles, up-converting nanoparticles, cadmium selenide/cadmium sulfide fusion nanoparticles, quantum dots, and a Near-Infrared (NIR) fluorophore or material (such as, but not limited to, materials such as lanthanide clusters and phthalocyanines, as well as light emitting-diodes consisting of CuPc, PdPc, and PtPc) capable of emitting light in the NIR spectrum. In some embodiments, a capture reagent and/or particle is conjugated to the signal detection unit, such as but not limited to, colloidal gold, silver, radioactive tag, fluorescent tag, or a chemiluminescent substrate, near-infrared compound (e.g. substrate, molecule, particle), or infrared compound (e.g. substrate, molecule, particle), nanoparticle, emissive nanoparticle, quantum dot, magnetic particle, or an enzyme.

The signal detection unit can also be, for example, a viral particle, a latex particle, a lipid particle, a fluorescent particle, a near-infrared particle, or infrared particle. As used herein, the term "fluorescent particle" means a particle that emits light in the fluorescent spectrum. As used herein, the term "near-infrared particle" means a particle that emits light in the near-infrared spectrum. As used herein, the term "infrared particle" means a particle that emits light in the infrared spectrum. In some embodiments, the colloidal gold has a diameter size of: about 20 nm, about 30 nm, or about 40 nm, or in the range of about 20-30 nm, about 20-40 nm, about 30-40 nm, or about 35-40 nm. In some embodiments, the particle comprises a metal alloy particle. In some embodiments, the metal alloy particle has a diameter from about 10 to about 200 nm. Examples of metal alloy particles include, but are not limited to, gold metal alloy particles, gold-silver bimetallic particles, silver metal alloy particles, copper alloy particles, Cadmium-Selenium particles, palladium alloy particles, platinum alloy particles, and lead nanoparticles.

Figure 5:
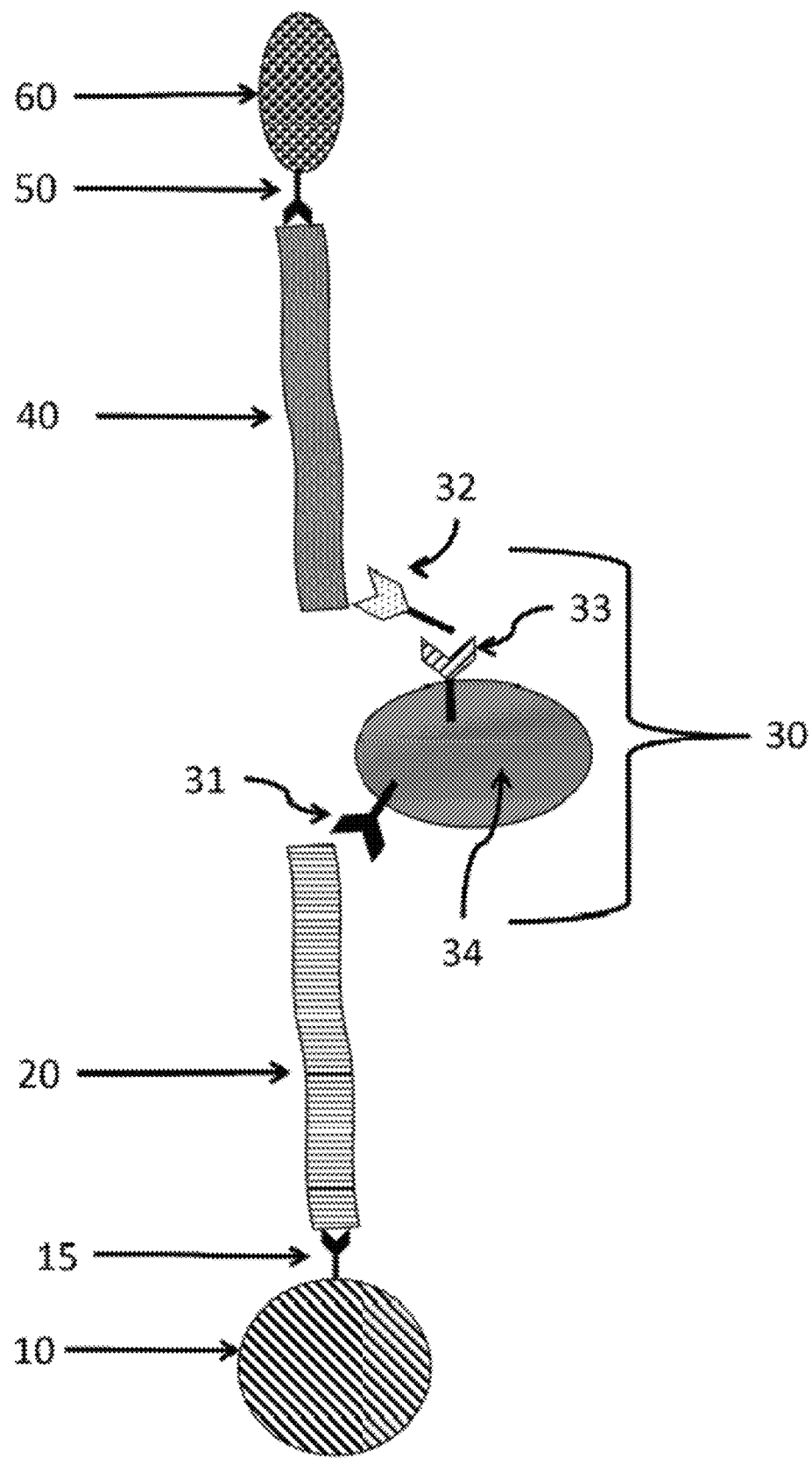
FIG. 5 illustrates, among other aspects, the representative detection of two analytes with a single signal using a multi-component bridging unit.
Figure 6:
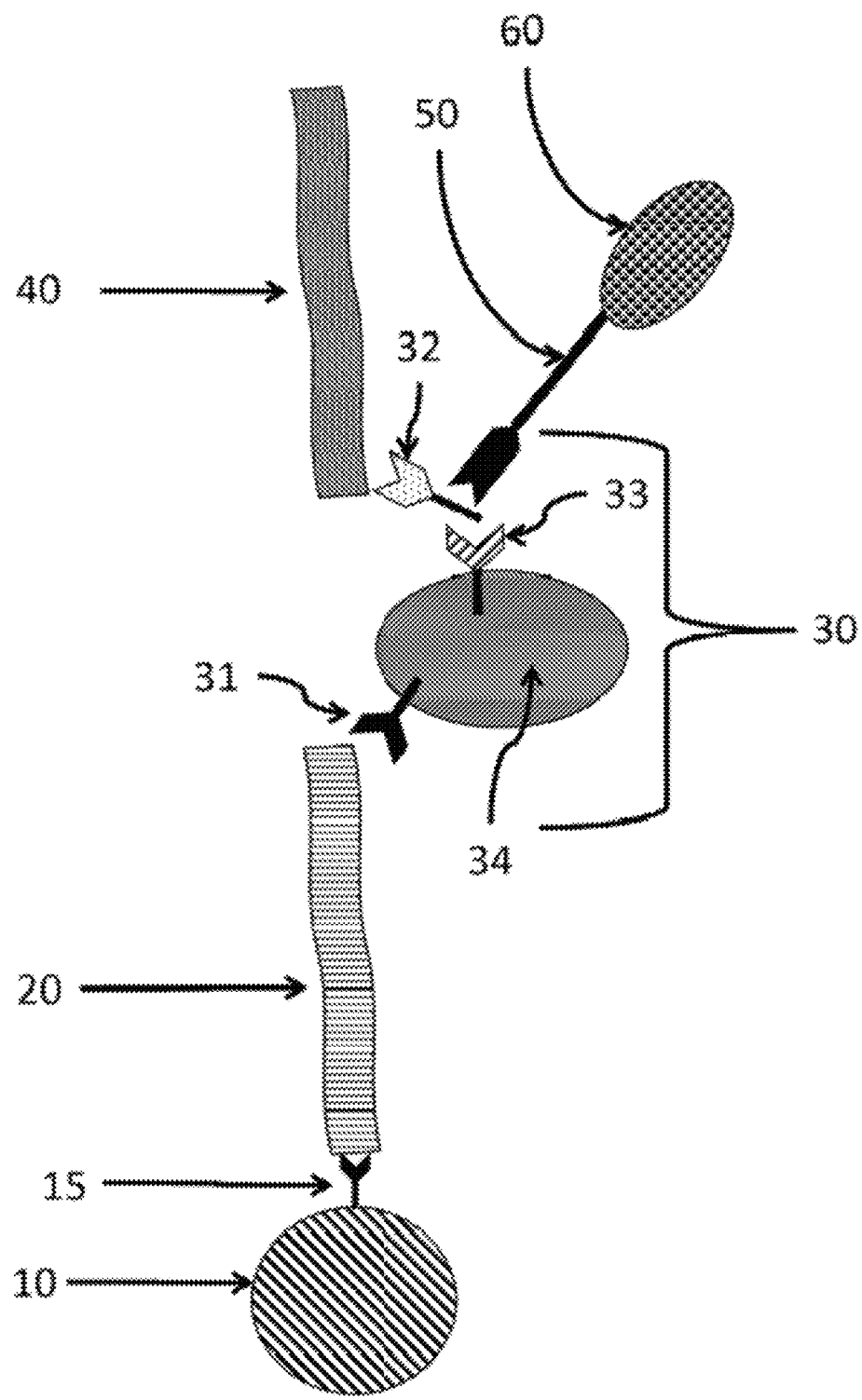
FIG. 6 illustrates, among other aspects, the signal detection unit binding to a component of the bridging unit that is only present when the plurality of analytes is present in the complex.

As discussed herein the signal detection can will bind to one of the analytes. A non-limiting example of the signal detection unit binding to an analyte is shown in FIG. 1. FIG. 1, which is described in more detail herein, shows the signal detection unit 60 binding to the analyte 40 through a capture reagent 50. However, the signal detection unit can also bind to other portions of the complex. Any component that is necessarily present only when both the plurality of analytes is present in the complex can be a binding partner for the signal detection unit. Often, but not exclusively this will be one of the analytes, but can also be a capture reagent that is bound to the analyte. In contrast, in some embodiments, the signal detection unit does not bind solely to the analyte that is bound to the solid support, the solid support, or the capture reagent bound directly to the solid support, if present on the solid support. For example, in FIG. 1, the signal detection unit will not bind directly to the solid support 10, the capture reagent 15, or the analyte 20. Without being bound to any particular theory, if the signal detection unit binds directly with the solid support 10, the capture reagent 15, or the analyte 20, the method would provide a false positive as the signal would be detected without the plurality of analytes necessarily being present. For example, FIG. 6, illustrates the signal detection unit binding to a component of a multi-component bridging unit. Embodiments of the bridging unit, and a multi-component bridging unit, are described herein and, for example, with references to FIGS. 4 and 5. FIG. 6 illustrates a signal detection unit 60 with its capture reagent 50 binding to a component of the bridging unit 30. The bridging unit comprises 30 a particle 34, a first capture reagent 31, a second capture reagent 32, and a third capture reagent 33. FIG. 6 illustrates the signal detection unit binding to the second capture reagent 32. The capture reagent 32 will only be present in the complex if both analytes are present in the complex. If capture reagent 32 is not present this means that there is no bridged complex of the plurality of analytes. Therefore, the signal detection unit will only be part of the complex if the plurality of analytes are present in the complex, thus avoiding false positives. If both analytes are not present the capture reagent 32 will not be part of the complex, and, therefore, there will be no binding partner for the signal detection unit. Accordingly, the signal detection unit will only be detectable when the plurality of analytes are present. Therefore, in some embodiments, the signal detection unit binds to any component that is only present when the plurality of analytes are also present. Other properties, characteristics, and structural features of the multi-component bridge unit are also disclosed herein and are readily apparent based upon the present disclosure.

Examples of devices in which the presently described methods can be used are described in, for example, in U.S. Pat. No. 8,012,770, U.S. patent application Ser. No. 13/360,528, filed Jan. 27, 2012, PCT Publication No. WO 2011/044574, each of which is incorporated herein by reference in its entirety. The presently describes methods, however, can be used with any number of devices or formats, such as multi-well plates, arrays, microarrays, or in an "ELISA" type format. Examples of devices are also described herein, but these examples are non-limiting. The methods described herein can also be used in conjunction with lateral flow devices. In a lateral flow device the different portions of the device are in the same plane as opposed to a vertical flow device. Non-limiting examples of the lateral flow devices can be found in U.S. Pat. Nos. 6,485,982, 6,818,455, 6,951,631, 7,109,042, RE39,664, and the like, each of which are hereby incorporated by reference. The lateral flow devices can be adapted for the methods described herein as they are described for the vertical flow devices. In a lateral flow device, the region that indicates a positive or negative result can comprise the capture reagent that binds to one of the analytes. The bridge unit can either be present in one of the lateral flow regions or mixed with the analytes before addition to the device—this can also be done for other devices and solid supports. The signal detection unit can also be incorporated into one of the lateral flow regions. As is clear from the present disclosure the type of device or solid support is not critical and the methods can be adapted based upon the examples and embodiments described herein.

As used herein, the term "amplicon" means an amplification product such as a nucleic acid molecule that is amplified by a PCR reaction or other amplification reaction or method. As discussed herein, an amplicon can be an analyte. The amplicon can be a double-stranded nucleic acid molecule. The amplification product can be detected directly or indirectly through the use of antibodies or other capture reagent systems, including those that are described herein. The amplification product can also be detected through hybridization methods in whole or in part as described herein. The amplification product can also be produced, for example, through RT-PCR or linear amplification.

In some embodiments, the amplicon is a PCR product. The PCR reaction products (e.g. amplicons) can be labeled such that they are detectable either by another antibody or antibody like system, such as but not limited to biotin-avidin/streptavidin system, systems, hapten systems, BRDU labeling of DNA, intercalating agents that label DNA, labeled dNTPS, and the like can also be used where the PCR products are labeled. The analyte, which can, for example, but not limited to, be a nucleic acid (single stranded or double stranded) and can be recognized or detected with an antibody or other capture reagent system, such as those described herein. The nucleic acid molecule can be labeled with a biotin label or other type of label that can be detected using a method described herein. Other examples of labels include fluorescent labels. The fluorescent labels can be for example, fluorescein (e.g. fluorescein isothiocyanate (FITC)), rhodamine (e.g. tetramethylrhodamine (TAMRA)), and the like. The amplicons can be generated with these labels by using labeled primers. The labels can be incorporated into the amplicon through the amplification procedure and, thus, become part of the analyte. The labels would be considered heterologous tags because the labels are not found in the native sequence that is used as the template for the amplicon. Capture reagents (e.g. antibodies) can be used that bind to the labels to help in forming the complexes that are described herein, which enable the detection of multiple analytes with a single signal. These labels can act as interaction units. A non-limiting example of how the labels can act as interaction units such that multiple analytes can be detected with a single signal is shown in FIG. 3.

For example, in some embodiments, a PCR reaction is performed with a hapten and/or biotin labeled DNA or RNA primers with homology to an analyte nucleic acid sequence. The analyte nucleic acid sequence can be, but not limited to, a toxin gene and/or a toxin molecule (e.g. Shiga toxin) from a meat sample. The sample, however, can be any sample, and the analyte can be any other type of analyte described herein. The PCR reactions can be performed to produce multiple analytes with the interaction units. Following amplification with the primers, the PCR sample can be detected using a method described herein. The PCR reaction can also be performed with digoxigenin and/or TAMRA and/or with FITC and TAMRA labeled primers. These can create the differentially labeled amplicons that can be bridged together through the use of capture reagents to enable the detection of multiple analytes with a single signal. An example of such a complex is shown in FIG. 3.

Figure 3:
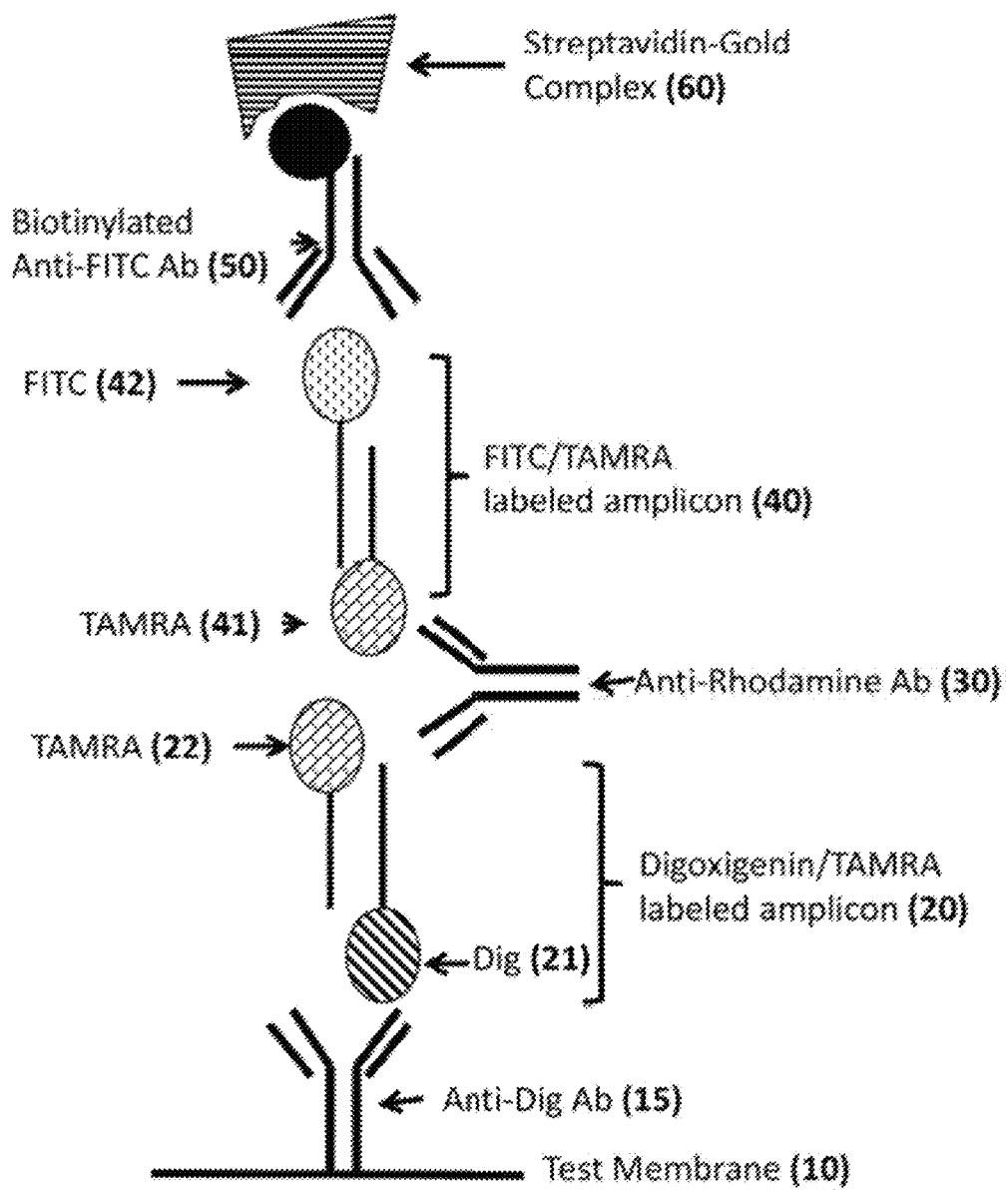
FIG. 3 illustrates, among other aspects, two amplification products being detected with colloidal gold.

FIG. 3 illustrates a test membrane (i.e., solid support 10) with an Anti-Dig antibody (i.e., capture reagent 15), a Digoxigenin/TAMRA labeled amplicon (i.e., a first analyte 20, a first interaction unit 21, and a second interaction unit 22), an anti-rhodamine antibody ((i.e. bridge unit 30), a FITC/TAMRA labeled amplicon (i.e., a second analyte 40, a first interaction unit 41, and a second interaction unit 42); and a streptavidin-gold complex binding to a biotinylated anti-FITC antibody (i.e., a signal generation unit 60 and a third capture reagent 50).

Briefly, after the PCR reactions are performed, the amplicons can be contacted with a solid support, a bridging unit, and a signal detection unit. The solid support can have a capture reagent that binds to an interaction unit on the first analyte. The bridging unit can have, or be, a capture reagent that binds to interaction units on the first and second analytes such that the binding to the interaction units on the first and second analytes brings the analytes together into a complex. The signal detection unit can bind to an interaction unit present on the one of the second analyte. The signal detection unit can then emit a detectable signal or the signal detection unit can be detected by the addition of another detection system. For example, in FIG. 3, the signal detection unit is a capture reagent (e.g. antibody) that binds to the interaction unit on the second analyte. The signal detection unit is biotinylated. The presence of the signal detection unit can be then be determined by the addition of streptavidin. The streptavidin will only bind to a complex that has both analytes present. In the non-limiting example shown in FIG. 3, the streptavidin is labeled with colloidal gold which enables the detection. However, other labels or detection systems could be used to detect the streptavidin. In the embodiments of the vertical flow devices described herein, the test membrane is the solid support with the capture reagent, and the conjugate pad can comprise the signal detection unit or the molecule that detects the binding of the signal detection unit to the interaction unit of the second analyte.

Figure 7:
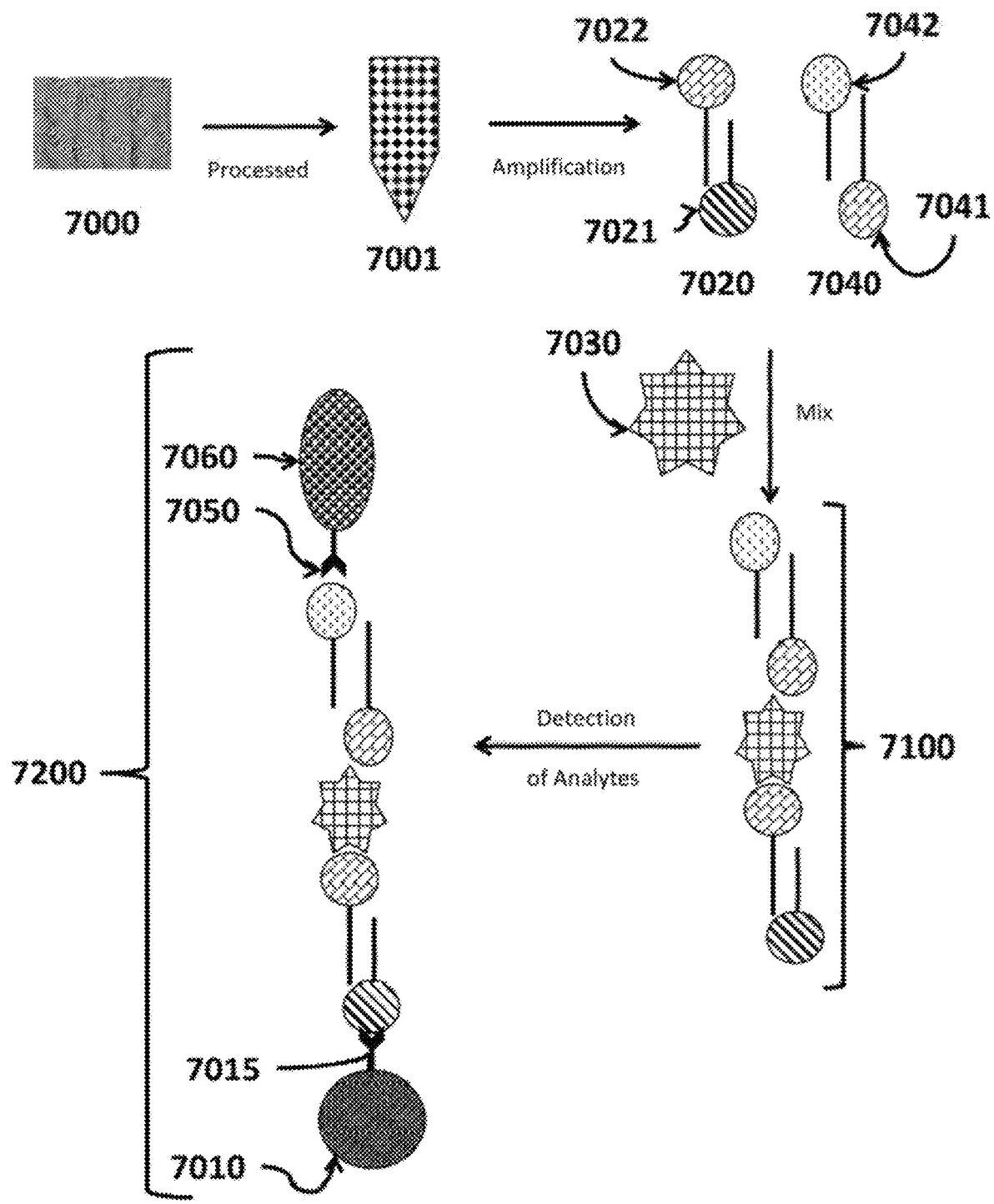
FIG. 7 illustrates, among other aspects, a non-limiting workflow for detecting a plurality of analytes with a single signal.

FIG. 7 illustrates a non-limiting work flow procedure that could be used to detect a plurality of analytes with a single signal using amplicons to detect the presence of an analyte of interest in a sample. A food sample 7000 is analyzed to determine the presence or absence of pathogenic *E. Coli*. The food sample 7000 is processed (e.g. enriched, cultured, nucleic acid, purification, isolation, extraction, or other similar steps) to extract, isolate or otherwise make available the nucleic acids present in the food sample. The nucleic acid sequences present in the processed sample 7001 can be amplified, such as but not limited to by PCR, to amplify the specific pathogenic *E. Coli* sequences. Examples of these sequences are described herein. No specific primer set need be used as those can be modified based upon the target sequence to be amplified. As described herein, the primers can be labeled, thereby creating labeled amplicons (analytes with heterologous interaction units). The first analyte 7020 and the second analyte 7040 will be generated if the target sequences are present in the food sample and the processed sample. The analytes are shown with heterologous interaction units (7021, 7022, 7041, and 7042). The analytes can be mixed with a bridge unit 7030. The mixture will form a bridged complex 7100. The analytes can then be detected by contacting the bridged complex with a solid support 7010 comprising a capture reagent 7015 and a signal detection unit 7060 comprising a capture reagent 7050. As discussed herein, the a signal detection unit 7060 comprising a capture reagent 7050 can be absorbed onto a membrane and allowed to interact with the bridged complex. The solid support 7010 comprising a capture reagent 7015 can be a test membrane with an antibody. These elements can be incorporated into a device as described herein. Although FIG. 7 shows the steps being performed separately they can also be performed in different order and some steps may be combined. For example, the step of mixing the analytes with the bridge unit can also be combined with contacting the analytes with the signal detection unit comprising a capture reagent. The detection step of adding to the complex to the solid support could then be done subsequently. In some embodiments, the analytes, bridge unit, signal interaction unit comprising a capture reagent, and the solid support comprising a capture reagent can be mixed together simultaneously or nearly simultaneously and then the signal detection unit can be detected. The signal detection unit will only be detected or detected above background levels (i.e. above a negative control) when the plurality of the analytes are present in the sample being tested. That is, in FIG. 7, the complex 7200 will only be formed if both analytes, and thus both target sequences are present in the food sample 7000, are present. The complex 7200 will not be formed if one of the analytes is missing. The workflow shown in FIG. 7 can also include a washing step to wash away any unbound material or components that do not form a complex 7200. Washing steps may also be incorporated into any method described herein.

In some embodiments of the methods described herein, the method of detecting a plurality of analytes with a single signal comprises amplifying a plurality of target nucleic acid sequences present in a sample. The target sequences can be the analytes or the amplified products can be the analytes. The detection of the amplified sequences (e.g., PCR products) indicates the presence of the template sequences in the original sample.

In some embodiments, methods of concurrently detecting a plurality of analytes with a single signal comprise a) contacting a device for detecting a plurality of analytes with a single signal with one or more samples comprising a plurality of analytes; and detecting the presence or absence of the signal detection unit which indicates the presence or absence of the first analyte of interest and second analyte of interest concurrently. The device can be any device used to detect the presence or absence of analyte including, but not limited to the devices described herein. In some embodiments, the device comprises: a housing comprising: an inlet opening in fluid contact with a conjugate pad; a force member; a slidable locking member contacting the force member; an attachment member contacting the force member; a sliding button contacting the attachment member; and a detection membrane system comprising the conjugate pad, a test membrane, and an absorbent member, at least a portion of the conjugate pad, test membrane, and absorbent member are substantially parallel to each other, the force member contacts the detection membrane system and is capable of applying pressure substantially perpendicular to the detection membrane system, the sliding button moves the slidable locking member, the conjugate pad comprises a signal detection unit comprising a third capture reagent; the test membrane comprises a first capture reagent affixed to the test membrane.

In some embodiments, the one or more samples comprises a first analyte of interest, a second analyte of interest, and a bridge unit comprising a second capture reagent, wherein the first analyte of interest comprises a first interaction unit that binds to the first capture reagent and a second interaction unit that binds to the bridge unit, and the second analyte of interest comprises a first interaction unit that binds the bridge unit and a second interaction unit. In some embodiments, the signal detection unit comprises the third capture reagent that binds to the second analyte, to the second analyte's first interaction unit or second interaction unit, to a component of the first and second analyte complex, or to a component of the bridge unit that that is only present when the complex contains the first and second analytes.

In some embodiments, the detecting comprises moving the conjugate pad after a portion of the one or more samples has contacted and flowed through the conjugate pad, thereby exposing at least a portion of the test membrane for detection of the signal detection unit to indicate the presence or absence of the plurality of analytes with a single signal. In some embodiments, the conjugate pad is moved by moving the slidable locking member. In some embodiments, the one or more samples are contacted with the conjugate pad prior to compressing the detection membrane system. The method can be performed with multiple samples to detect the plurality of analytes. For example, if a plurality of amplification reactions are performed to produce a plurality of amplicons (analytes) each of the plurality of amplifications reactions is considered a separate sample. To detect the plurality of analytes with a single signal the samples have to be mixed. The plurality of samples can be mixed prior to contacting the device or be contacted with the device (solid support) sequentially, or simultaneously.

In some embodiments, the first and second analyte are amplicons. In some embodiments, the first and second analytes are PCR reaction products. In some embodiments, the first analyte's first interaction unit is a digoxigenin label. In some embodiments, the first analyte's second interaction unit is a rhodamine label. In some embodiments, the second analyte's first interaction unit is a rhodamine label. In some embodiments, the second analyte's second interaction unit is a fluorescein label. In some embodiments, the third capture reagent binds to the second analyte's second interaction unit. In some embodiments, the third capture reagent is a biotinylated capture reagent. In some embodiments, the signal interaction unit is coated with streptavidin. In some embodiments, the signal interaction unit is streptavidin coated colloidal gold. In some embodiments, the first and second analytes are nucleic acid amplification products, wherein: the first analyte comprises a digoxigenin label and a rhodamine label; the second analyte comprises a rhodamine label and a fluorescein label; the first capture reagent is an anti-digoxigenin label antibody; the second capture reagent is an anti-rhodamine label antibody; the third capture reagent is a biotinylated anti-fluorescein label antibody; and the signal interaction unit is streptavidin coated colloidal gold.

As used herein and throughout, the terms "attached" or "attachment" can include both direct attachment or indirect attachment. Two components that are directly attached to one another are also in physical contact with each other. Two components that are indirectly attached to one another are attached through an intermediate component. For example, Component A can be indirectly attached to Component B if Component A is directly attached to Component C and Component C is directly attached to Component B. Therefore, in such an example, Component A would be said to be indirectly attached to Component B.

The term "capture reagent" means a reagent capable of binding a target molecule or analyte to be detected in a sample. Examples of capture reagents include, but are not limited to, antibodies or antigen binding fragments thereof, an oligonucleotide, and a peptoid. Other examples of capture reagents include, but are not limited to, small molecules or proteins, such as biotin, avidin, streptavidin, hapten, digoxigenin, BRDU, single and double strand nucleic acid binding proteins or other intercalating agents, and the like, or molecules that recognize and capture the same. These are non-limiting examples of capture reagents. Other types of capture reagents can also be used.

As discussed herein, a capture reagent can also refer to, for example, antibodies. Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

Non-limiting examples of binding fragments encompassed within the term "antigen-specific antibody" used herein include: (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue $(Gly_4Ser)_3$ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof. The capture reagent or antibody can also be a VHH region, a bi-specific antibody, a peptide fragment comprising an antigen binding site, or a compound that binds to an antigen of interest. The antigen of interest can be an amplicon or other type of analyte.

These antibodies can be purchased or obtained using conventional techniques known to those skilled in the art, and the fragments are screened for utility in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and Biacore analysis, to identify one or more hybridomas that produce an antibody that specifically interacts with a molecule or compound of interest.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature.

The term "capture reagent" also includes chimeric antibodies, such as humanized antibodies, as well as fully humanized antibodies. In some embodiments the capture reagent is a Goat anti-*E. coli* 0157:H7 antibody Cat #: 70-XG13 (Fitzgerald Industries); *E. coli* 0157:H7 mono Cat #: 10-E13A (Fitzgerald Industries); *E. coli* 0157:H7 Cat #: 10C-CR1295M3 (Fitzgerald Industries); *E. coli* 0157:H7 mono Cat #: 10-E12A (Fitzgerald Industries); or Goat anti-mouse IgG Cat #: ABSE-020 (DCN). The capture reagent can also be, for example, protein A, protein G, and the like. The capture reagent can also be an antibody that binds or specifically binds to a fluorescent label (e.g. fluorescein or rhodamine), a hapten, digoxigenin and the like. A capture reagent, such a streptavidin can be conjugated with colloidal gold. The streptavidin-gold complex can then be used, for example, to bind to a biotinylated product, such as a biotinylated antibody. A non-limiting example can be seen in FIG. 3. The labels shown in FIG. 3 are for illustrative purposes only and other permutations can be used.

The capture reagent can also include an anti-antibody, i.e. an antibody that recognizes another antibody but is not specific to an analyte, such as, but not limited to, anti-IgG, anti-IgM, or ant-IgE antibody.

As used herein, the term "concurrently" refers to the detection of multiple analytes simultaneously or nearly simultaneously. As used herein, "A method of concurrently detecting a plurality of analytes with a single signal," or variations thereof, refers to a method that uses a single assay (e.g. single well, single dot, single location on an array) or a single use of a device to detect the plurality of analytes with a single signal. If different devices, wells, or arrays are used to detect the plurality of analytes with the same signal this is not a method of concurrently detecting a plurality of analytes with a single signal. For a method to be a method of concurrently detecting a plurality of analytes with a single signal the method must generate only a single signal (examples of signals are described herein) in a single location (well, dot, line on a membrane or other type of solid support, and the like), that informs the user that the plurality of analytes are present in the sample. For example, the same signal being used in different wells to indicate whether a single analyte is present in that well (or spots on an array) and then analyzing the multiple wells (or spots) to determine if the plurality of analytes are present is not a method of concurrently detecting a plurality of analytes with a single signal.

As used herein, the term "single signal" means detection of a signal based upon a single moiety or method. For example, if the single signal is the color red, then the plurality of analytes indicated by only upon the presence of the color red. That is, the color red, in this non-limiting example, indicates that the plurality analytes are present in the sample. In contrast, if one analyte is indicated by the color red and a second analyte is indicated by the color yellow, the use of two colors (i.e., signals) is not the detection of a plurality of analytes with a single signal. The signal is not limited to colorimetric detection. Examples are provided herein of signals that can be used.

The term "detecting" or "detection" is used in the broadest sense to include qualitative and/or quantitative measurements of a target analyte.

As used herein, the term "interaction unit" means a part of the analyte or a heterologous tag or label that is attached to the analyte that that is recognized or bound by another molecule (e.g. the capture reagent, the bridge unit, or the signal detection unit). The interaction unit can be part of the analyte itself or can be a heterologous tag or label. The interaction unit can also be an antibody or other type of capture reagent that recognizes the analyte. In some embodiments, the analyte can comprise more 1, 2, 3, 4, or 5, interaction units. In some embodiments, the interaction unit is a capture reagent that binds to another interaction unit present on the analyte itself or a heterologous tag that is part of the analyte. For example, if the analyte is a peptide or part of a protein, a part of the protein or peptide itself can be the interaction unit recognized by the capture reagent, bridge unit, or the signal detection unit. In some embodiments, the peptide can also be covalently attached to a heterologous tag or label and the heterologous tag or label or the complex of the peptide with the heterologous tag or label is considered the interaction unit. Thus, in some embodiments, an analyte comprises a first interaction unit and/or a second interaction unit. In some embodiments, the interaction unit(s) can be intrinsic to the analyte itself or the interaction unit(s) could be added through some other method, such as cross-linking, covalent attachment through a chemical reaction, non-covalent interactions (e.g. antibody-antigen, hybridization between a part of the analyte and another molecule, and the like). Where the interaction unit is formed by the hybridization of two molecules (e.g. two nucleotide sequences), such that the part of the hybridization product that is recognized by another molecule would be considered the interaction unit. The interaction units can also be added to the analyte through an amplification reaction. This can be produced through the use of primers that contain the interaction units. Interaction units can also have detectable signals, but it is not these signals that are detected.

As used herein, the term "heterologous" in reference to the interaction unit means a group, molecule or moiety that is not native to the analyte. For example, an amplification product can comprise just nucleic acid molecules or nucleotide bases. The amplification product, however, can be conjugated to or attached to a heterologous tag, such as, but not limited to, hapten, biotin, digoxigenin, a fluorescent molecule (e.g. fluorescein or rhodamine) and the like. Examples of heterologous interaction units include, but are not limited to, hapten, biotin, nucleic acid molecules, peptide fragments (e.g. His-tags, GST-tags, and the like), enzymes, streptavidin, avidin, fluorescent molecules, and the like. This list is non-limiting and any interaction unit can be used. Analytes can be labeled with molecules such as digoxigenin, rhodamine, fluorescein, DNP, BRDU, and then be detected by capture reagents that are specific for a given molecule.

According to some embodiments, methods of detecting a plurality of analytes is provided. The presently described methods can be used to detect multiple analytes. An unexpected and surprising result is that multiple analytes can be detected using a single signal. This has the unexpected result that the presence, or absence, of multiple analytes can be detected with only the detection of one signal. This is in contrast to the detection of the presence of multiple analytes using distinct signals in the same reaction to detect the presence of multiple analytes in a sample or requiring the performing of separate reactions and methods to detect multiple analytes. That is, the embodiments described herein provide, in part, methods of detecting multiple analytes concurrently with a single signal, such that the detection of a single signal indicates the presence of the multiple analytes in a sample or that the absence of the single signal indicates the absence of the multiple analytes in the sample. The present embodiments provides methods of detecting at least 2, 3, 4, or 5 analytes concurrently with a single signal. In some embodiments, the method can be used to detect 2, 3, 4, or 5 different analytes concurrently with a single signal. Although many examples are provided for detecting 2 analytes, the methods can be adapted and modified based upon the present disclosure for the detection of 3, 4, or 5 analytes.

As used herein, the term "different analytes" means the analytes are not the same. The different analytes, however, can be referred to with the same name, but be from different organisms or from different strains of the same organism. For example different organisms contain genes and proteins that have the same function and, therefore, have been given the same name. But the genes or proteins are from different sources and thus are considered different analytes. They may or may not have different sequences. Different analytes can also means analytes from different organisms. For example, there are any many strains of *E. coli*. Not all strains of *E. coli* cause a food-borne illness. The present methods can be used, for example, to detect a plurality of analytes from a pathogenic *E. coli* strain as opposed to detecting an analyte from a non-pathogenic *E. coli* strain. Although reference made be made throughout the present disclosure to specific types of analytes, the analytes can be any type of analyte, such as but not limited, to the classes of analytes described herein.

For example, in some embodiments, methods of concurrently detecting a first analyte and a second analyte are provided. In some embodiments, the method comprises contacting a solid support, which comprises a first capture reagent with a first analyte, a second analyte, a bridge unit, which comprises a second capture reagent, and a signal detection unit comprising a third capture reagent; and detecting the presence of the signal detection unit which indicates the presence of the first analyte and second analyte. In some embodiments, the first capture reagent is affixed to the solid support. In some embodiments, the first analyte comprises a first interaction unit that binds to the first capture reagent and a second interaction unit that binds to the bridge unit; the second analyte comprises a first interaction unit that binds the bridge unit and a second interaction unit that binds to the signal detection unit. The signal detection unit can then be detected. If the signal detection unit is detected, it indicates that the multiple analytes are present.

Without desiring to be bound by any theory, the multiple analytes can be detected concurrently by forming a complex. In some embodiments, the complex comprises the solid support, the first analyte, the second analyte, the bridge unit, and the signal detection unit wherein each member of the complex binds to each other directly or indirectly. The sample can be washed while retaining the solid support and the complex will only be detected if the complex is formed. Examples of these complexes can be seen in FIGS. 1-3, which are further described herein.

In some embodiments, methods of concurrently detecting a first analyte and a second analyte are provided, the method comprising: contacting a solid support with a first analyte of interest, a second analyte of interest, a bridge unit comprising a second capture reagent, and a signal detection unit comprising a third capture reagent; and detecting the presence or absence of the signal detection unit which indicates the presence or absence of the first analyte of interest and second analyte of interest concurrently, wherein: a first capture reagent is affixed to the solid support; the first analyte of interest comprises a first interaction unit that binds to the first capture reagent and a second interaction unit that binds to the bridge unit; and the second analyte of interest comprises a first interaction unit that binds the bridge unit; a signal detection unit that binds to the second analyte, to the second analyte's first interaction unit or a second interaction unit, to a component of the first and second analyte complex or bridge unit that that is only present when the complex contains the first and second analyte.

FIG. 1 illustrates a complex that could be formed to detect two analytes concurrently with a single signal. FIG. 1 illustrates a capture reagent 15 affixed to a solid support 10. The capture reagent 15 binds to the first analyte 20. The bridge unit 30 binds to the first analyte. The bridge unit also binds to the second analyte 40. FIG. 1 also illustrates a signal detection unit 60 comprising a capture reagent 50 that binds to the second analyte 40. FIG. 1 illustrates that this complex only forms when all of the members are present and can bind to one another. The signal detection unit can then be detected. FIG. 3 also shows an embodiment of detecting two analytes with a single signal. FIG. 3 shows specific labels (e.g. FITC, TAMRA, DIG, biotin, streptavidin, etc. . . . ), but these labels can be modified according to the present disclosure.

In some embodiments, the method comprises one or more washing steps. The washing step can be used to remove unbound materials. For example, if the solid support is contacted with a first sample, the solid support can be washed to remove any unbound material. In some embodiments where the solid support is a bead, the beads can be contacted with the sample and then the beads can be washed. Washing beads is routine and well known to one of skill in the art. The method of washing beads or other types of solid supports can be altered or chosen based upon the specific solid support that is used and is often not a critical feature.

In some embodiments, the sample with the first analyte is contacted with the solid support. In some embodiments, the mixture is washed such that any materials not bound to the solid support are no longer present. In some embodiments, the solid support is also contacted with the same sample or a different sample comprising the second analyte and/or the bridge unit. The mixture can then be washed again to remove any unbound material. In some embodiments, a signal detection unit comprising a capture reagent is added. A washing step can also be included to remove any unbound signal detection units. The signal detection unit can then be detected or another reagent can be added that detects the presence of the signal detection unit. In some embodiments, all of the steps are performed simultaneously or nearly simultaneously. During the performance of the method, a washing step may be inserted where appropriate.

In some embodiments, the different analytes or samples can be mixed together before or simultaneously applied to the solid support. The samples can be, for example, amplification reaction mixtures that were used to produce, or attempted to produce, the analytes. In some embodiments, different amplification reactions will be performed to amplify the plurality of analytes. Therefore, prior to the samples or analytes being applied to the solid support the samples or analytes can be mixed together. The samples or analytes can also be mixed with the capture reagents and/or bridging units prior to being contacted with the solid surface.

In some embodiments, the first and second interaction unit of the first analyte and the first and second interaction unit of the second analyte are each independently a heterologous interaction unit. In some embodiments, an interaction unit of the first analyte and an interaction unit of the second analyte is a hapten. In some embodiments, the interaction unit of the first analyte and the second analyte is fluorescein or rhodamine molecule. Accordingly, in some embodiments, the first analyte and second analyte have at least one interaction unit in common. The commonality of the interaction unit will enable the bridging unit to bring the two analytes into a detectable complex. In some embodiments, the first and second analytes do not have the same interaction unit. In such a case for some embodiments, the bridging entity would be a bivalent capture reagent (e.g. bivalent antibody) that can link the two analytes to one another. The bivalent capture reagent would be able to bind to both the first and second analytes simultaneously. In some embodiments, each of the interaction units present on the plurality of analytes are different. In some embodiments, some of the interactions units are different, but some of the interaction units are the same. In some embodiments, the analyte comprises a hapten interaction unit and a biotin interaction unit. In some embodiments, the first analyte comprises a digoxigenin interaction unit and a rhodamine interaction unit; the second analyte comprises a rhodamine interaction unit and a FITC interaction unit, and the bridging unit binds to the rhodamine interaction unit. The bridging unit can then form the complex that contains both the first and second analyte. This can be seen, for example, in FIG. 3.

In some embodiments, the plurality of the analytes are the same type of analyte. For example, each of the analytes being detected can be a peptide. In some embodiments, each of the analytes is a nucleic acid molecule, such as an amplification product (e.g. amplicon). The analytes can also be any type, including, but not limited to, the analytes described herein. In some embodiments, the analytes are different. In some embodiments, a first analyte is an amplification product and a second analyte is a protein or peptide. Any combination of analytes can be used.

As used herein, the term "bridge unit" or "bridge" means a molecule(s) that can link two or more analytes in a complex. That is, for example, the bridge unit can bind to an interaction unit on a first analyte and an interaction unit on a second analyte. If only detecting two analytes, one bridge unit may be used. If detecting three analytes, two bridge units can be used. In some embodiments, the methods use "n−1" bridge units, where "n" is the number of analytes being detected. In some embodiments, a single bridge unit is used to detect more than 2 analytes. Examples of bridge units include, but are not limited to, immunoglobulin molecules (e.g. IgM, IgE, IgG, IgA, and the like), streptavidin, and a molecule that comprises a plurality of capture reagents such that the bridge unit can bind to more than one interaction unit. In some embodiments, the bridge unit is a multivalent capture reagent.

In some embodiments, the bridge unit is a complex of compounds, substances, or macromolecules. For example, a bridge unit could comprise a nanoparticle coated with antibodies and a separate antibody. In this non-limiting example, the nanoparticle coated with antibodies can contain antibodies that bind to an analyte or interaction unit on the analyte and also contain antibodies that bind to the separate antibody. The separate antibody can bind to a different analyte. The interaction of the nanoparticle coated with antibodies and the separate antibody would then be able to bridge together the different analytes. A non-limiting illustration of this bridge complex can be seen in FIGS. 4 and 5, which is also described below. Other variations of the bridge being a complex could also be made. The exact structure and form of the bridge unit is not essential so long as it can "bridge" a plurality of analytes in a complex. Thus, the bridge could be made up of multiple subunits or components to bridge the analytes together. Although the bridge unit can be illustrated and discussed bridging two analytes, the bridge unit can be designed to bridge more than 2 analytes, such as 3, 4, 5, or more. Therefore, in some embodiments, the bridge unit bridges 2, 3, 4, 5, or more analytes. In some embodiments, the bridge unit bridges at least 2, 3, 4, or 5 analytes. The non-limiting example of bridging 2 analytes is for illustrative purposes only and the embodiments disclosed herein are not limited to bridging only 2 analytes.

As discussed herein, the present methods can be applied to detecting more than 2 analytes. For example, a method of detecting a first analyte, a second analyte, and a third analyte concurrently with a single signal is provided. For the detection of additional analytes, the methods can be adapted in a similar manner. In some embodiments, the method comprises contacting the first, second, and third analytes with a solid support, a first bridge unit, a second bridge unit, and a signal detection unit; and detecting the presence of the signal detection unit which indicates the presence of the first, second, and third analytes concurrently with a single signal, wherein the first analyte comprises a first interaction unit and a second interaction unit; the second analyte comprises a first interaction unit and a second interaction unit; the third analyte comprises a first interaction unit and a second interaction unit; the solid support comprises a first capture reagent that binds to the first interaction unit of the first analyte; the first bridge unit binds to the second interaction unit of the first analyte and the first interaction unit of the second analyte; the second bridge unit binds to the second interaction unit of the second analyte label and the third interaction unit of the third analyte; and the signal detection unit binds to the second interaction unit of the third analyte. Without being bound to any theory, it is expected that the analytes can be concurrently detected because the first, second, and third analytes form a complex, wherein the complex comprises the solid support, the first analyte, the second analyte, the third analyte, the first bridge unit, the second bridge unit, and the signal detection unit wherein each member of the complex binds to each other directly or indirectly.

FIG. 2 illustrates a complex that can be formed to detect three analytes, which is analogous to the example illustrated in FIG. 1. FIG. 2 illustrates a solid support 10 with a capture reagent 15 bound to a first analyte 70. The first analyte is bound to a first bridge unit 80. The first bridge unit is bound to a second analyte 20, which is also bound to a second bridge unit 30. The second bridge unit is also bound to a third analyte 40, which is bound to a capture reagent 50. The capture reagent is also attached to a signal detection unit 60. Thus, FIG. 2 illustrates a non-limiting example of how three analytes can be detected with a single signal.

Figure 4:
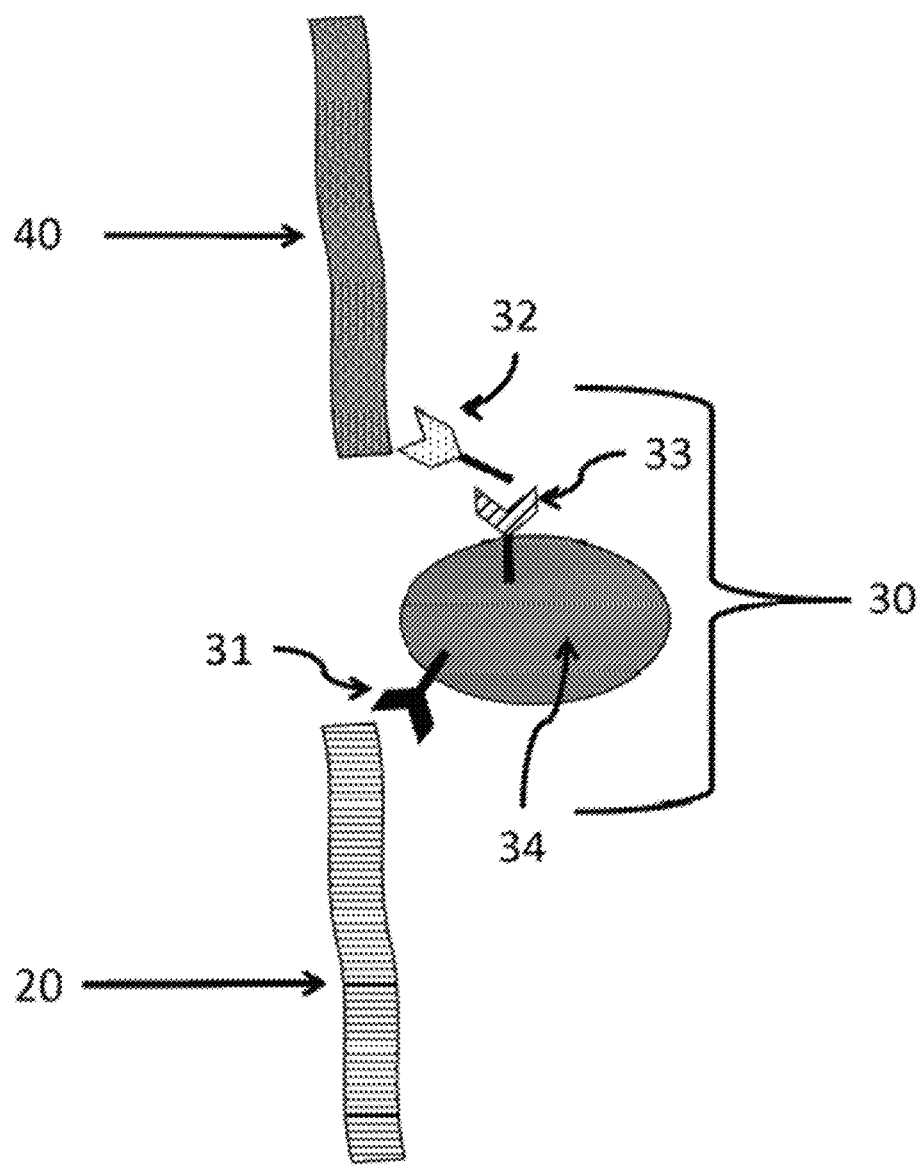
FIG. 4 illustrates, among other aspects, a multi-component bridging unit.

FIG. 4 illustrates a non-limiting bridge complex made up of more than one molecule, macromolecule, or substance. This can be referred to as a multi-component bridge complex. FIG. 4 illustrates a bridge unit 30 that comprises a particle 34, a first capture reagent 31, a second capture reagent 32, and a third capture reagent 33. The bridge unit 30 is able to bring together the first analyte 20 and the second analyte 40 and from a complex linking the first analyte 20 and the second analyte 40. FIG. 4 illustrates a particle 34 (e.g. nanoparticle, polystyrene, agarose, and the like) coated with a first capture reagent 31 that binds to the first analyte 20, either directly or indirectly through an interaction unit, a third capture reagent 33, which is also present on the particle 34, that binds to a second capture reagent 32 that is bound to the second analyte 40. This complex can then be detected according to the methods and compositions described herein, which is illustrated in FIG. 5. FIG. 5 shows the bridges complex of FIG. 4 interacting with a solid support 10 with a capture reagent 15 bound to a first analyte 20 and a signal detection unit 60 comprising a capture reagent 50 that binds to the second analyte 40. As discussed herein, the illustration of the signal detection unit binding to the second analyte is for illustrative purposes only. The signal detection unit can also bind other parts of the complex so long as the signal detection unit is not binding to the analyte that is interacting with the solid support or the solid support itself. The solid support 40 can be, for example, a test membrane, such as the test membrane that is shown in FIG. 3. Other examples of solid supports are provided herein.

The present invention provides complexes comprising a solid support, a first analyte, a second analyte, a bridge unit, and a signal detection unit wherein each member of the complex binds to each other directly or indirectly. In some embodiments, the solid support is bound to the first analyte, the bridge unit is bound to the first analyte and the second analyte, and the signal detection unit is bound to the second analyte. In some embodiments, the solid support comprises a first capture reagent, the first analyte comprises a first interaction unit and a second interaction unit, the second analyte comprises a first interaction unit and a second interaction unit, the bridge unit comprises one or more capture reagents that independently bind to the second interaction unit of the first analyte and the first interaction unit of the second analyte, and the signal detection unit comprises a capture reagent that binds to the second interaction unit of the second analyte.

In some embodiments, the complex comprises a solid support, a first analyte, a second analyte, a third analyte, a first bridge unit, a second bridge unit, and a signal detection unit, wherein the solid support, the first analyte, second analyte, third analyte, first bridge unit, second bridge unit, and signal detection unit are bound to each other directly or indirectly. In some embodiments, the solid support binds to the first analyte, the first bridge unit binds to the first analyte and the second analyte, the second bridge unit binds to the second analyte and the third analyte, and the signal detection unit binds to the third analyte. In some embodiments, the solid support comprises a first capture reagent, the first analyte comprises a first interaction unit and a second interaction unit, the second analyte comprises a first interaction unit and a second interaction unit, the third analyte comprises a first interaction unit and a second interaction unit, the first bridge unit comprises one or more capture reagents that independently bind to the second interaction unit of the first analyte and the first interaction unit of the second analyte, the second bridge unit comprises one or more capture reagents that independently bind to the second interaction unit of the second analyte and the first interaction unit of the third analyte, and the signal detection unit comprises a capture reagent that binds to the second interaction unit of the third analyte.

In some embodiments, the presently described methods can be used to detect a food borne pathogen by the detection of a plurality of food-borne pathogen analytes with a single signal. For example, a sample may be processed to isolate an analyte (e.g. an antigen or a toxin, or a food borne pathogen nucleic acid may be isolated or amplified). The plurality of analytes (e.g. food borne pathogen protein and/or an amplicon) can be detected concurrently with the methods described herein. The methods can then provide greater confidence in the specificity of the test and avoid false negatives. In some embodiments, a positive result that indicates the presence of a food borne pathogen requires the detection of 2, 3, or 4 analytes. The present methods can be used to detect the analytes concurrently with a single signal. The single signal provides an easier result to interpret since the signal will only be detectable if all of the plurality of analytes being detected are present in the sample. Thus, if 2 analytes are being detected then the signal will only be detectable if both analytes are present. In some embodiments, the signal is only detectable when 3 analytes are present. This type of methods can be applied to other methods of detection.

In some embodiments, the method can be used to detect 3 classes of analytes to provide a positive test for food contamination. In some embodiments, one of the analytes is a toxin (e.g. Shiga toxin 1 and/or 2). The toxin can be detected itself or the nucleotide sequence that encodes or controls the production of the toxin can be detected. In some embodiments, one of the analytes is eae gene, which can also be referred to as a virulence factor. The eae gene can be found, or expressed in, for example, enterohemorrhagic *Escherichia coli*.

In some embodiments one of the analytes is a serotype analyte, which can be an antigen that is specifically produced by a strain of a food borne pathogen. In some embodiments, the serotype analyte is an *E. coli* serotype. In some embodiments, the *E. coli* serotype is O26, O45, O103, O111, O121, and O145. Therefore, in some embodiments, a positive test for food borne contamination requires the detection of 3 analytes with a single signal, wherein the 3 analytes are the Shiga toxin (e.g. Shiga toxin 1 and/or 2), the eae gene, and a serotype analyte chosen from *E. coli* serotype is O26, O45, O103, O111, O121, and O145. In some embodiments, the serotype analyte is a protein specifically expressed by a pathogenic strain. In some embodiments, the analyte is a nucleic acid sequence that encodes the antigen. In some embodiments, the nucleic acid sequence is a fragment of the coding sequence of the antigen. The specific fragment is not critical and one of skill in the art can determine the sequences or fragments thereof to amplify using routine methods. As discussed herein, the target sequence can be amplified and optionally labeled with a heterologous interaction unit. The analytes can then be detected according to the methods provided herein.

For example, if a positive test for a virus requires the presence of two distinct nucleic acid sequences, the two nucleic acid sequences can be detected concurrently with a single signal using the methods described herein as opposed to detecting the two nucleic acid sequences separately with more than one signal. Additionally, if the presence of cancer requires the detection of a plurality of genes being expressed in sample, the genes can be detected concurrently with a single signal by using analytes that correlate with their expression (e.g. by using RT-PCR to amplify the gene product) according to a method described herein. Therefore, the presently described methods have wide applicability and can be used with any plurality of analytes (target molecules) and even with analytes that are not the same.

In some embodiments, methods are provided for detecting two or more analytes comprising detecting the multiple analytes using a flow (vertical or lateral) device. Examples of vertical flow devices and methods of using them are provided in U.S. Pat. Nos. 8,012,770, 8,183,059 and U.S. patent application Ser. Nos. 13/500,997, 13/360,528, 13/445,233, each of which is hereby incorporated by reference in its entirety. The devices can be adapted for the detection of multiple analytes using a single signal.

Accordingly, embodiments provided herein provide methods of detecting multiple analytes with a single signal by using vertical flow and devices employing vertical flow. Vertical flow allows the analyte and/or the sample to flow through the layers/membranes of the analyte detection membrane system. By "through layers" or "through membranes" is meant to refer to the sample flowing through the layers and vertically across the layers. In some embodiments, the sample does not flow horizontally or laterally across the different layers/membranes.

The following terms are used in conjunction with the description of various vertical flow devices. Other terms are defined relevant to some vertical flow devices or uses thereof are described throughout as well.

The term "pressure actuator" and "force actuator" can be used interchangeably and refer to a component that can exert, for example, pressure through the application of force. A force actuator can also be referred to as a force member. Examples of include, but are not limited to, various force members that are described herein. Other examples include, but are not limited to, pistons or other solid support structures. The force actuator's position relative to another component can be raised, lowered, or moved laterally. The position of the force actuator can be controlled manually or through a signal processing unit (e.g. computer). The ability to control the position of the force actuator can be used to regulate the force (e.g. pressure) being applied to another component, such as, but not limited to, an analyte detection membrane system. By regulating the force applied to the membrane system the flow rate of the sample can be regulated. The force can be used to keep the flow rate of the sample through the membrane system constant or the flow rate can be variable. The flow rate can also be stopped and allow the sample to dwell on different layers of the membrane system. For example, the sample's flow rate can be zero or near zero when the sample contacts the conjugate pad. After resting on the conjugate pad the flow rate can be increased by modulating the pressure being applied by the force actuator. The sample can then through the entire membrane system, or the force being applied can be modulated to allow the sample to dwell (rest) on another layer of the membrane system. Force can be precisely regulated, either manually or by using a signal processing unit (e.g. computer) the flow rate can be modified at any point as the sample vertically flows through the membrane system. The flow rate can also be regulated based upon the absorbency of the membranes in the membrane system and/or the number of the membranes of the system. Based upon the absorbency the flow rate can be modulated (e.g. increased or decreased).

The flow rate can be measured in any units including but not limited to µl/min or µl/sec, and the like. The flow rate during a dwell can be, for example, 0 µl/sec, or less than 1, 0.9, 0.8, 0.7, 0.6, 0.5, 0.4, 0.3, 0.2, or 0.1 µl/sec or µl/min. The flow rate can be monitored manually or by a signal processing unit (e.g. computer) and regulated by the same. The flow rate can be regulated and monitored by well-known and routine methods known to one of skill in the art in addition to those described herein. In some embodiments, the flow rate is about 0 to 1 ml/min, about 0-10 ml/min, about 1-9 ml/min, about 1-8 ml/min, about 1-7 ml/min, about 1-6 ml/min, about 1-5 ml/min, about 1-4 ml/min, about 1-3 ml/min, about 1-2 ml/min, about 0.5-1.5 ml/min, about 1-1.5 ml/min, or about 0.5-1 ml/min. In some embodiments, the flow rate is about 1, 2, 3, 4, 5, 6, 7, 8, 9, or 10 ml/min. In some embodiments, the flow rate is at least 1, 2, 3, 4, 5, 6, 7, 8, 9, or 10 ml/min. In some embodiments, the flow rate is 1, 2, 3, 4, 5, 6, 7, 8, 9, or 10 ml/min.

In some embodiments, the devices used to detect multiple analytes with a single signal comprise a housing comprising a first housing member and a second housing member. In some embodiments, the first and second housing members can be constructed as a single unit. The housing can comprise an inlet opening. The inlet opening allows the introduction of a sample onto the chromatographic assay. In some embodiments, the first housing member comprises the inlet opening. The inlet opening can be of sufficient size to handle an appropriate amount of volume of a solution that is added to the device. In some embodiments, the size of the opening is large enough to handle about 0.1 to 3 ml, about 0.1 to 2.5 ml, about 0.5 to 2.0 ml, about 0.1 to 1.0 ml, about 0.5 to 1.5 ml, 0.5 to 1.0 ml, and 1.0 to 2.0 ml.

In some embodiments, the housing comprises a conjugate pad, a permeable membrane, a test membrane, and/or an absorbent member. In some embodiments, the housing comprises an analyte detection membrane system. In some embodiments, the analyte detection membrane system comprises a conjugate pad, a permeable membrane, a test membrane, and an absorbent member. In some embodiments, the analyte detection membrane system is free of a permeable membrane. In some embodiments, the analyte detection membrane system comprises in the following order: a conjugate pad, a permeable membrane, a test membrane, and an absorbent member.

As used herein, the term "conjugate pad" refers to a membrane or other type of material that can comprise a capture reagent. The conjugate pad can be a cellulose acetate, cellulose nitrate, polyamide, polycarbonate, glass fiber, membrane, polyethersulfone, regenerated cellulose (RC), polytetra-fluorethylene, (PTFE), Polyester (e.g. Polyethylene Terephthalate), Polycarbonate (e.g., 4, 4-hydroxy-diphenyl-2, 2'-propane), Aluminum Oxide, Mixed Cellulose Ester (e.g., mixture of cellulose acetate and cellulose nitrate), Nylon (e.g., Polyamide, Hexamethylene-diamine, and Nylon 66), Polypropylene, PVDF, High Density Polyethylene (HDPE)+nucleating agent "aluminum dibenzoate" (DBS) (e.g. 80 u 0.024 HDPE DBS (Porex)), and HDPE. Examples of conjugate pads also include, Cyclopore® (Polyethylene terephthalate), Nucleopore® (Polyethylene terephthalate), Membra-Fil® (Cellulose Acetate and Nitrate), Whatman® (Cellulose Acetate and Nitrate), Whatman #12-S (rayon)), Anopore® (Aluminum Oxide), Anodise® (Aluminum Oxide), Sartorius (cellulose acetate, e.g. 5 µm), and Whatman Standard 17 (bound glass). The conjugate pad can also be made of a material that dissolves after coming into contact with a sample or other liquid. The dissolving of the conjugate pad can be performed so that other layers of the systems described herein can be revealed or exposed for either visual inspection (e.g. detection of an analyte) or for spectrometer inspection (e.g. detection of an analyte by a spectrometer).

In some embodiments, the conjugate pad or test membrane comprises a capture reagent. In some embodiments, the conjugate pad or test membrane is contacted with the capture reagent and then allowed to dry before being used in the vertical flow device. The conjugate pad or test membrane can also comprise other compositions to preserve the capture reagent such that it can be stably stored at room temperature or under refrigeration or freezing temperatures. In some embodiments, the conjugate pad or test membrane is soaked with a buffer prior to the capture reagent being applied. In some embodiments, the buffer is a blocking buffer that is used to prevent non-specific binding. In some embodiments, the buffer comprises Borate, BSA, PVP40 and/or Tween-100, or any mixture thereof. In some embodiments, the buffer is 10 mM Borate, 3% BSA, 1% PVP40, and 0.25% Tween-100. In some embodiments the capture reagent is applied to the pad or membrane in a solution comprising trehalose and sucrose. In some embodiments, the capture reagent is applied to the pad, membrane, or both, in a solution comprising trehalose, sucrose and phosphate and/or BSA. In some embodiments, the capture reagent is applied in a solution that is 5% trehalose, 20% sucrose, 10 mM phosphate, and 1% BSA. In some embodiments, the test membrane comprises a capture reagent that binds to a labeled amplicon. In some embodiments, the capture reagent is an antibody that recognizes or binds to digoxigenin, fluorescein (e.g. FITC), rhodamine (TAMRA), and the like.

In some embodiments, the conjugate pad comprises streptavidin. The streptavidin can also be further labeled as described herein. In some embodiments, the streptavidin is the capture reagent that binds to a biotinylated antibody that is used to detect multiple analytes with a single signal.

In some embodiments, the removable member contacts a first surface of the conjugate pad and the adhesive member contacts a second surface of the conjugate pad.

In some embodiments, the device comprises an adhesive member. The adhesive member can comprises an adhesive member inlet that allows the sample to flow through the conjugate pad and contact the test membrane. In some embodiments, the adhesive member inlet is the same size or shape as the removable member inlet. In some embodiments, the adhesive member inlet is a different size or shape as the removable member inlet. In some embodiments, the inlets in the adhesive member are the same shape but have different areas. Inlets with different areas would be considered to have different sizes. The adhesive member can be made up of any substance suitable for adhering one member or membrane to another member or membrane. In some embodiments, the adhesive member is impermeable to liquid. In some embodiments, the adhesive member contacts the removable member.

In some embodiments of the device, the permeable membrane is attached to or adhered to a test membrane. In some embodiments, the permeable membrane is laminated onto the test membrane. The permeable membrane can be a membrane of any material that allows a sample, such as a fluid sample, to flow through to the test membrane. Examples of test membrane include, but are not limited to, nitrocellulose, cellulose, glass fiber, polyester, polypropylene, nylon, and the like. In some embodiments, the permeable membrane comprises an opening. The opening can be present to allow visualization or detection of the test membrane. In some embodiments, the opening in the permeable membrane is substantially the same size as the inlet opening in the housing. Examples of permeable membranes include, but are not limited to, Protran BA83, Whatman, and the like.

As discussed herein, one example of a solid support is a test membrane. As used herein and throughout, the "test membrane" refers to a membrane where detection of a binding partner to a capture reagent occurs. Test membranes include, but are not limited to a nitrocellulose membrane, a nylon membrane, a polyvinylidene fluoride membrane, a polyethersulfone membrane, and the like. The test membrane can be any material that can be used by one of skill in the art to detect the presence of a capture reagent's binding partner (e.g. labeled analyte, antigen or epitope). The test membrane can also comprise a capture reagent. In some embodiments, the test membrane is contacted with a capture reagent and the capture reagent is allowed to dry and adhere to the test membrane. Examples of test membranes include, but are not limited to Protran BA83, Whatman, Opitran BA-SA83, and 0.22 μm white plain (Millipore Product No. SA3J036107). Test membranes may also be comprised of nanoparticle matrices to which capture reagents are bound. Nanocrystals can be arranged into 2D sheets and 3D matrices with materials such as, but not limited to, carbon based particles, gold or metal alloy particles, co-polymer matrices, as well as monodisperse semiconducting, magnetic, metallic and ferroelectric nanocrystals. The test membrane can comprise a plurality of capture reagents. In some embodiments, the test membrane comprises 1, 2, 3, 4, 5, 6, 7, 8, 9, or 10 capture reagents. In some embodiments, the test membrane comprises a plurality of areas each with a different capture reagent. In some embodiments, the plurality of areas do not completely overlap or coincide with one another.

In some embodiments, the device or housing also comprises an absorbent member. The absorbent member can also be referred to as a "wick pad" or "wicking pad." The absorbent member absorbs the fluid that flows through the device when the sample is applied to the device and provides for the wicking force that aids in the flow of the sample when it is applied to the device. "Absorbent member" is meant to refer to a material that has a capacity to draw (wick) and retain solution away from a surface that the material is in contact with. Use of a combination of material of increasing or decreasing absorbance can also allow for control of sample movement.

The absorbent member can be any material that can facilitate the flow of the sample through the conjugate pad and to the test membrane. Examples of absorbent members include, but are not limited to cellulose, super absorbent polymers, glass fiber pads (e.g. C083 (Millipore)), and the like. In some embodiments, the housing comprises a plurality (e.g. 2 or more) of absorbent members. In some embodiments, the housing comprises 2, 3, 4, or 5 absorbent members. In some embodiments, the device comprises one absorbent member. In some embodiments, the absorbent member comprises one or more membranes up to 10 individual membranes, and each membrane may be the same material or a different material. In some embodiments, the device consists of only 1 membrane that is an absorbent member.

Figure 23:
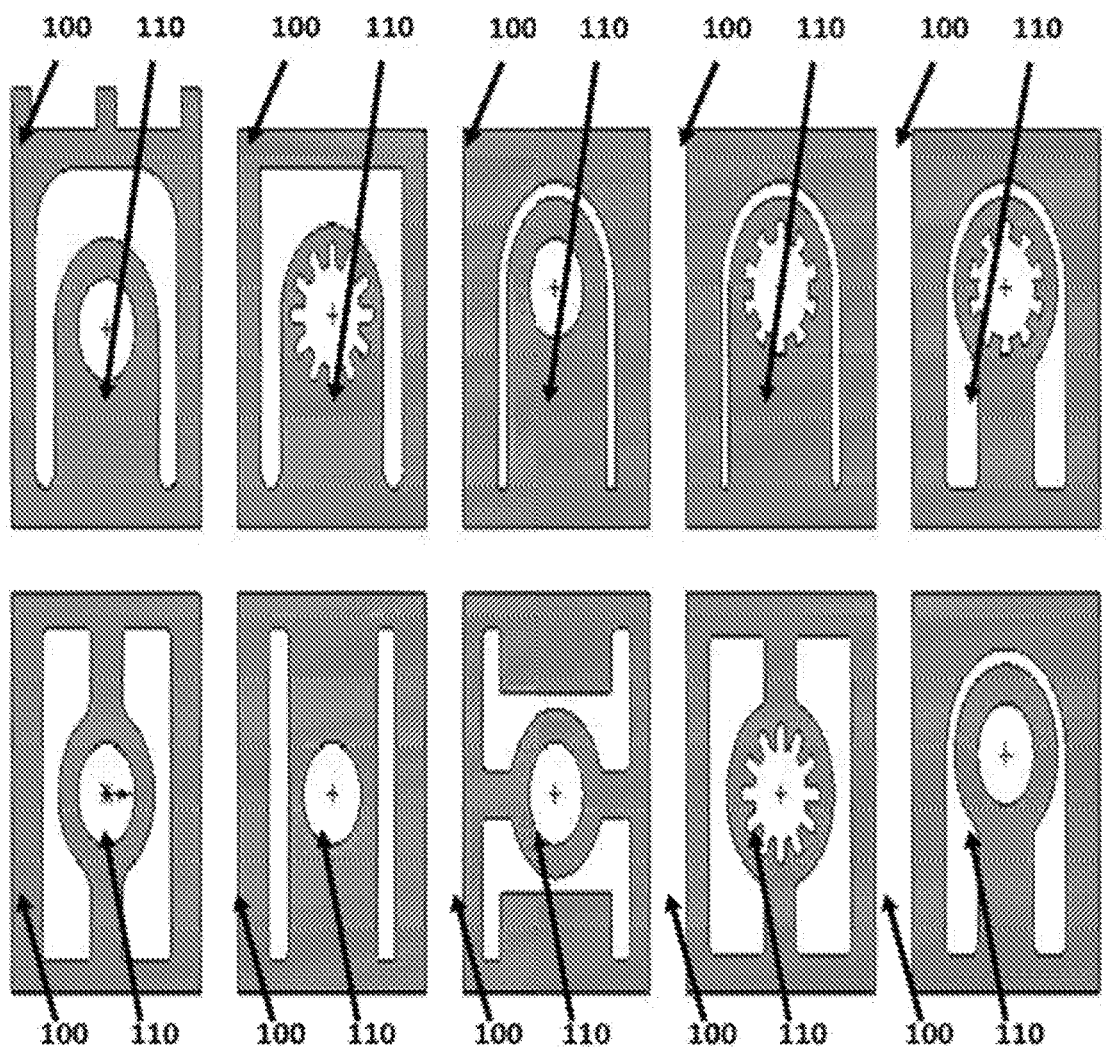
FIG. 23 depicts representative force members for a representative device according to some embodiments of the present invention.

In some embodiments, the device comprises a force member. Examples of force members are described below and can be seen in the drawings. These examples are non-limiting and other forms of force members can be used. The force member can, in some embodiments, be used to apply pressure or to compress the other components of the analyte detection membrane system against one another. In some embodiments, the force member can be made out of any material including, but not limited to plastic or stainless steel. As shown in FIG. 23, clips can act as force members. The stainless steel can be laser cut such that it can act as a clip. Non-limiting examples of these clips can be seen in FIG. 23. The force member acts to apply pressure to the membrane system. The force member is not limited to a clip, but rather can be any shape (see, Figures for non-limiting examples) that can apply pressure to the membrane system (e.g. nanoparticle matrices) and piston like structures strategically placed within the assembly. In some embodiments, the force member is a piston. The force member can be used to apply pressure or to compress the other components of the analyte detection membrane system against one another. In some embodiments, the force member can comprise a shaft and a head. The force member can have a mushroom type shape where the head is wider than the shaft. In some embodiments, the head is narrower than the shaft. The force member comprising a head and a shaft can be a single unit or can be made up of multiple parts that contact one another to form the force member. For example, the head could be one unit that can be separated from the shaft. Upon assembly the head and shaft are contacted with one another to make the force member. In another example, the head and shaft are one cohesive unit and are manufactured together and not as separate parts that are later assembled to form the force member. The force member allows the device to work with vertical flow as opposed to relying upon lateral flow.

In some embodiments, the force member contacts a surface of the absorbent member. In some embodiments, the force member contacts a surface of the absorbent member and a surface of the removable layer. In some embodiments, the force member compresses the membrane detection system from above and below the membrane detection system. For example, in some embodiments, the force member can sandwich all the layers of the membrane detection system. In some embodiments the force member is attached to a support member.

In some embodiments, the device comprises, in the following order, a removable member, a conjugate pad, and an adhesive member.

The device can also comprise a support member. The support member, in some embodiments, contacts a surface of the absorbent member. The support member can also have a support member inlet. The inlet can be the same size and/or shape as the inlet in the removable member and/or the adhesive member. In some embodiments, the support member comprises an inlet that is a different size and/or shape as the inlet in the removable member and/or the adhesive member. The support member can be made from any material including, but not limited to, plastic. In some embodiments, the second housing member serves as the support member.

The devices described herein can be used in assays to detect the presence of a capture reagent's binding partner. These assays can as shown herein be used to detect multiple analytes for the detection of single signals. For example, an antigen can be detected by an antibody using the devices of the present invention. The term "Vertical flow" is used throughout. The term "vertical flow" refers to the direction that the sample flows across the different membranes and members present in a device. Vertical flow refers to a sample flowing through the membrane (e.g. top to bottom) as opposed to lateral flow, which refers to a sample flowing across (e.g. side to side) a membrane, pad or absorbent member. In a lateral flow device the membranes and pads sit horizontally adjacent to one another substantially on the same plane. In a vertical flow device each membrane or pad is substantially parallel or completely parallel to each other and occupy substantially different spatial planes in the device. The membranes and pads may occupy similar planes when they are compressed or put under pressure. In some embodiments, at least a portion of each member, membrane, or pad is layered on top of each other. In some embodiments, at least a portion of each layer of member, membrane, or pad is substantially parallel to each other. In some embodiments, at least a portion of each layer is in a different spatial plane than each other layer.

To allow vertical flow to occur efficiently, in some embodiments and when present, the conjugate pad, permeable membrane, test membrane and the absorbent member are substantially parallel to each other. In some embodiments, the conjugate pad, permeable membrane, test membrane and the absorbent member are present in different spatial planes. In some embodiments, the housing also comprises a hydrophobic membrane that can slow or stop the vertical flow of the sample. The hydrophobic membrane can be in contact with the test membrane, which would allow the sample to dwell or rest upon the test membrane. The dwell can allow for increased sensitivity and detection. The vertical flow is modulated by the pressure that is applied to the membranes, pads, and/or members. In some embodiments, the pressure is applied perpendicular to the test membrane and/or the conjugate pad. In some embodiments, the pressure can be applied so that the conjugate pad is compressed against the housing. The compression against the housing can be such that the conjugate is in direct contact with the housing, O-ring, or collar, or through an intermediate so that the conjugate pad and the test membrane are compressed against one another.

The force member can apply pressure that is substantially perpendicular to the test membrane. Without being bound to any particular theory, the pressure facilitates the vertical flow. The pressure allows each layer of the membrane stack to be in contact with another layer. The pressure can also be relieved to stop the flow so that the test sample can dwell or rest upon the test membrane, which can allow for greater sensitivity. The pressure can then be reapplied to allow the vertical flow to continue by allowing the sample to flow into the absorbent member(s). The force member can apply pressure such that the conjugate pad contacts a portion of the housing (e.g., first or second housing members or removable layer). In some embodiments, the conjugate pad contacts the housing when it is not under the pressure being exerted by the force member but upon the force member exerting pressure the conjugate pad is compressed against a portion of the housing.

In some embodiments, the conjugate pad contacts the perimeter of the inlet opening. The inlet opening can also comprise a collar or other similar feature, such as an O-ring. In some embodiments, the conjugate pad contacts the perimeter of a collar and/or an O-ring. In some embodiments, the conjugate pad is capable of being compressed against the perimeter of the inlet opening, which can include, in some embodiments, a collar and/or an O-ring.

"Capable of being compressed against the perimeter of the inlet opening" refers to a membrane or pad (e.g. conjugate pad) being compressed either directly in contact with the perimeter of the inlet opening or being compressed against another layer or material (e.g. membrane) that is in contact with the perimeter of the inlet opening.

In some embodiments, the conjugate pad is not in direct physical contact with the housing but is in fluid contact with the housing. "Fluid Contact" means that if a sample is applied to the device through the inlet opening or other opening the fluid will contact the conjugate pad. In some embodiments, the conjugate pad can be separated from the housing by another membrane, such as a permeable membrane, where the other membrane is in direct physical contact with the housing or in direct physical contact with the collar or O-ring. When the sample is applied to the device the fluid can contact the other membrane first and then contact the conjugate pad. This is just one example of the conjugate pad being in fluid contact with the housing. There are numerous other embodiments where the conjugate pad is not in direct physical contact with the housing, the collar, or the O-ring, but is in fluid contact with the housing.

The force member can apply any pressure that is sufficient to facilitate vertical flow across the different membrane layers. In some embodiments, the layers of the device (e.g. conjugate pad, permeable membrane, test membrane, and absorbent member) are compressed under a force chosen from about 5 lbf to 100 lbf, about 5 lbf to 50 lbf, about 10 lbf to 40 lbf, about 15 lbf to 40 lbf, about 15 lbf to 25 lbf, or about 30 lbf to 40 lbf. In some embodiments, the layers of the device (e.g. conjugate pad, permeable membrane, test membrane, and absorbent member) are compressed under a force chosen from about 1 lbf to 100 lbf, about 1 lbf to 50 lbf, about 1 lbf to 5 lbf, about 1 lbf to 10 lbf, about 1 lbf to 15 lbf, about 1 lbf to 20 lbf, about 1 lbf to 30 lbf, or about 1 lbf to 25 lbf. The force can also compress a hydrophobic or impermeable membrane as well if one is present in the device.

In some embodiments of a device that can be used to detect multiple analytes with a single signal, the force member contacts a first surface of an absorbent member. In some embodiments, a conjugate pad contacts a test membrane. In some embodiments, a first surface of a test membrane contacts a permeable membrane. In some embodiments, a second surface of the test membrane contacts a second surface of the absorbent pad. In some embodiments, the device comprises a hydrophobic membrane, and, for example, the hydrophobic membrane contact a second surface of the test membrane. In some embodiments, the hydrophobic membrane contacts a first surface of the absorbent pad. In some embodiments, a conjugate pad contacts an adhesive member. In some embodiments, a test membrane contacts an adhesive member.

In some embodiments of a device that can be used to detect multiple analytes with a single signal, a first surface of the conjugate pad contacts the housing and a second surface of the conjugate pad contacts a first surface of the permeable membrane, wherein the second surface of the permeable membrane contacts a first surface of the test membrane, wherein a second surface of the test membrane contacts a first surface of the absorbent pad, wherein a second surface of the absorbent pad contacts the force member. In some embodiments, the first surface of the conjugate pad contacts a perimeter of the inlet opening of said housing. In some embodiments, the first surface of the conjugate pad contacts a perimeter of a collar or an O-ring.

In some embodiments of a device that can be used to detect multiple analytes with a single signal, a first surface of the conjugate pad contacts the housing and a second surface of the conjugate pad contacts a first surface of the adhesive member, wherein the second surface of the adhesive member contacts a first surface of the test membrane, wherein a second surface of the test membrane contacts a first surface of the absorbent pad, wherein a second surface of the absorbent pad contacts the support member. In some embodiments, the first surface of the conjugate pad contacts a perimeter of the inlet. In some embodiments, the first surface of the conjugate pad contacts a perimeter of a collar or an O-ring.

The device can also comprise an attachment member. In some embodiments, the attachment member is flexible or made from a flexible material. In some embodiments, the attachment member is fixed or made from a non-flexible material. The fixed attachment member can be, for example, a hinge and the like that can, for example, contact the conjugate pad or another layer or membrane of the system and can mediate its displacement. The fixed attachment member, such as, but not limited to, a fixed hinge or other compressible material that acts like a hinge and can return to a shape or dimension upon compression release. The attachment member can be capable of displacing the conjugate pad. The attachment member can also just be plastic and although can flex, its flexing properties are not used in the functioning of the device.

The flexible material can be, for example, an elastic or elastomer material. An attachment member can be, for example, attached to a conjugate pad and/or a hydrophobic membrane. The attachment member can also be attached to any membrane or member of the device. Examples of attachment members include, but are not limited to, elastomer band, rubber band, spring, and the like. In some embodiments, the attachment member can be made of a shape memory material. In some embodiments, the attachment member makes it possible to create a delay between moving the locking member and moving the conjugate pad or any other type of membrane or pad that the attachment member is attached to. In some embodiments, the movement of the pad or membrane does not happen at the same time as the sliding button or locking member is moved. In some embodiments of a device that can be used to detect multiple analytes with a single signal, and not being bound to any particular theory, as the sliding button or locking member is moved energy is accumulated in the attachment member and this energy is used to pull on a pad or membrane that it is attached to the attachment member after the pressure has been released. In some embodiments, the locking member is moved away from the force member (i.e., the force member no longer contacts the locking member) before the conjugate pad is moved or removed. The conjugate pad, in some embodiments, is moved once the compression or pressure being exerted by the force member is completely removed.

The attachment member can also be attached to either a sliding button or locking member. The attachment member can be attached through any means such as, adhesives, staples, tying, and the like to the other components. In some embodiments, the membrane or pad has notches in the membrane or pad that allow the attachment member to attach to the membrane or pad. A non-limiting example can be seen in FIG. 9.

In some embodiments of a device that can be used to detect multiple analytes with a single signal, the housing comprises a locking member. The locking member can be a slidable locking member that can move within the device. The locking member can be used to lock the force member in a position such that the force created by the force member upon the different layers is maintained. The locking member is, for example, locking the force member in place so that the pressure cannot be relieved unless the locking member is moved to allow the force member to change positions (i.e. lowered). The locking member, can for example, fit under the head of the force member, which would keep the force member in the raised position. The locking member can also be situated so that it keeps the force member in a particular position (e.g. raised or lowered). The locking member can be made of any material including, but not limited to, plastic and the like. The locking member can, for example, contact the force member either directly or indirectly through another component that prevents the force member from releasing the pressure. In some embodiments, the locking member contacts the force member to compress the conjugate pad.

The locking member can also contact the attachment member such that movement of the locking member will move the attachment member, any other membrane (e.g. conjugate pad, hydrophobic membrane, test membrane, or absorbent member) or other component that is attached to the attachment member. For example, if the locking member is moved to relieve the pressure of the force member thereby allowing the force member to change positions (e.g. from raised to a lower position), the movement of the locking member will also deform/accumulate energy into the attachment member so it can move the membrane or pad once the pressure has been sufficiently reduced. When the conjugate pad is attached to the attachment member and the locking member is moved this will also move the conjugate pad once the pressure has been sufficiently reduced. In some embodiments, the pressure is completely removed. The conjugate pad can be, for example, moved such that it is removed from the device. In some embodiments, the conjugate pad is moved to reveal the test membrane through the inlet opening. The amount of the test membrane that is revealed will depend upon the type of detection that is used. For a visual detection more of the test membrane may need to be revealed in the inlet opening. For a non-visual, e.g. fluorescent, near-infrared, infrared, radioactive or chemiluminescent detection, less or none of the test membrane may need to be revealed. In some embodiments, the conjugate pad is moved so that it no longer can be seen or detected through the inlet opening. In some embodiments, the movement of the conjugate pad can create another opening other than the inlet opening to visualize or detect the test membrane. In some embodiments, the conjugate pad is dissolved to visualize or detect the test membrane (e.g. detection of the analyte or multiple analytes with a single signal). The conjugate pad can be made of a dissolvable material such that when the conjugate pad comes into contact with the sample or another solution the conjugate pad partially or completely dissolves.

In some embodiments of a device that can be used to detect multiple analytes with a single signal, the attachment member is also attached to the impermeable or hydrophobic membrane. When the attachment member is moved the movement will also move or remove the impermeable or hydrophobic membrane. As discussed herein, the presence of the impermeable or hydrophobic membrane can allow the test sample to dwell or rest upon the test membrane by slowing or stopping the vertical flow. When the impermeable or hydrophobic membrane is moved or removed, either by its attachment to the attachment member or through other means, the vertical flow is no longer impeded or inhibited.

In some embodiments of a device that can be used to detect multiple analytes with a single signal, the housing comprises a sliding button. A sliding button can also be referred to as a sliding member. The sliding button can cross the inner and outer surfaces of the housing. In some embodiments, the sliding button or sliding member protrudes to an outer surface of the housing. In some embodiments, the sliding button is attached either directly or indirectly to the locking member. When the sliding button is attached (directly or indirectly) to the locking member the movement of the sliding button also moves the locking member. The attachment member in some embodiments can be attached to the sliding button. In some embodiments, the attachment member is attached to both the sliding button and the locking member. The sliding button and the locking member can also be constructed as a single unit.

In some embodiments of a device that can be used to detect multiple analytes with a single signal, any one or more of the inlets comprise an opening chosen from a range of about 0.2 to about 20 $cm^2$. In some embodiments, any one or more of the inlets is about 1 to about 2 cm in diameter. In some embodiments, any one or more of the inlets is about 1 or about 1.5 cm in diameter. In some embodiments, any one or more of the inlets is about 1, about 2, about 3, about 4, or about 5 cm in diameter. In some embodiments, where there is more than one inlet, the inlets can be different sizes or the same sizes. The size of each inlet is independent of one another. In some embodiments of the devices and systems described herein, the devices or systems comprises 1, 2, 3, 4, or 5 inlets. In some embodiments of the devices and systems described herein, the devices or systems comprises at least 1, 2, 3, 4, or 5 inlets.

In some embodiments of a device that can be used to detect multiple analytes with a single signal, the inlet opening comprise an opening chosen from a range of about 0.2-20 $cm^2$. In some embodiments, the inlet opening is about 1 to about 2 cm in diameter. In some embodiments, the inlet opening is about 1 or about 1.5 cm in diameter. In some embodiments, the inlet opening is about 1, about 2, about 3, about 4, or about 5 cm in diameter.

In some embodiments of a device that can be used to detect multiple analytes with a single signal, a device for detecting an analytes comprises a first member and a second member. In some embodiments, the first member and second member are in contact with each other. In some embodiments, the first member comprises one or more inlets. In some embodiments, between the first and second member is an analyte detection membrane system. In some embodiments, the analyte detection membrane system between the first and second member comprises a conjugate pad, an adhesive member, a test membrane and an absorbent member. In some embodiments, the analyte detection membrane system comprises in the following order: a conjugate pad; an adhesive member; a test membrane; and an absorbent member. As discussed herein, in some embodiments, at least a portion of each of the conjugate pad, test membrane, and absorbent member are substantially parallel to each other. In some embodiments, at least a portion of each of the conjugate pad, test membrane, and absorbent member are in a different spatial plane.

In some embodiments of a device that can be used to detect multiple analytes with a single signal, the analyte detection membrane system is compressed between the first and second member (e.g. of the force member). In some embodiments, the analyte detection membrane system is compressed between a plane formed by the first member and a plane formed by the second member wherein the planes formed by the first and second members are substantially parallel to each other and the analyte detection membrane system. In some embodiments, the planes are parallel to each other and the analyte detection membrane system. In some embodiments, the first and second members that compress the analyte detection membrane system is a force member. For example, the force member can be referred to as comprising a first and second member to create the force that compresses the analyte detection membrane system.

In some embodiments of a device that can be used to detect multiple analytes with a single signal, the first and second member are attached to one another along an edge of the first member that is parallel to an edge of the second member. In some embodiments, the first and second member are attached by a spring, hinge, and the like. The manner by which the first and second member are attached is not limited and can be by any structure that enables the analyte membrane system to be compressed between the first and second member. In some embodiments, the first and second member are contiguous with one another and form a clip. Examples of clips (e.g. force members) are shown throughout the present application (e.g. FIG. 16). The clip, can be for example cut from metal or other type of material that allows the first member to be flexible such that the analyte detection membrane system can be inserted between the first and second members. In some embodiments, the first member is removable.

In some embodiments of a device that can be used to detect multiple analytes with a single signal, the first member is attached or in contact with the conjugate pad, wherein the movement or removal of the first member moves the conjugate pad or removes the conjugate pad from the device. In some embodiments, the conjugate pad is removable.

In some embodiments of a device that can be used to detect multiple analytes with a single signal, the conjugate pad is removed from the device comprising the first and second member by removing only the conjugate pad.

In some embodiments of a device that can be used to detect multiple analytes with a single signal, the conjugate pad comprises a tab. The tab can be used to remove or to facilitate the removal of the conjugate pad.

Figure 18:
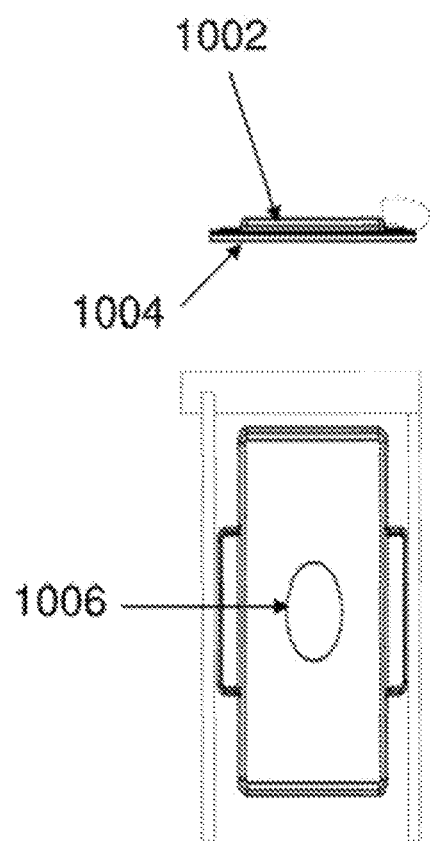
FIG. 18 depicts a side view and a top view of a representative device according to some embodiments of the present invention.
Figure 19:
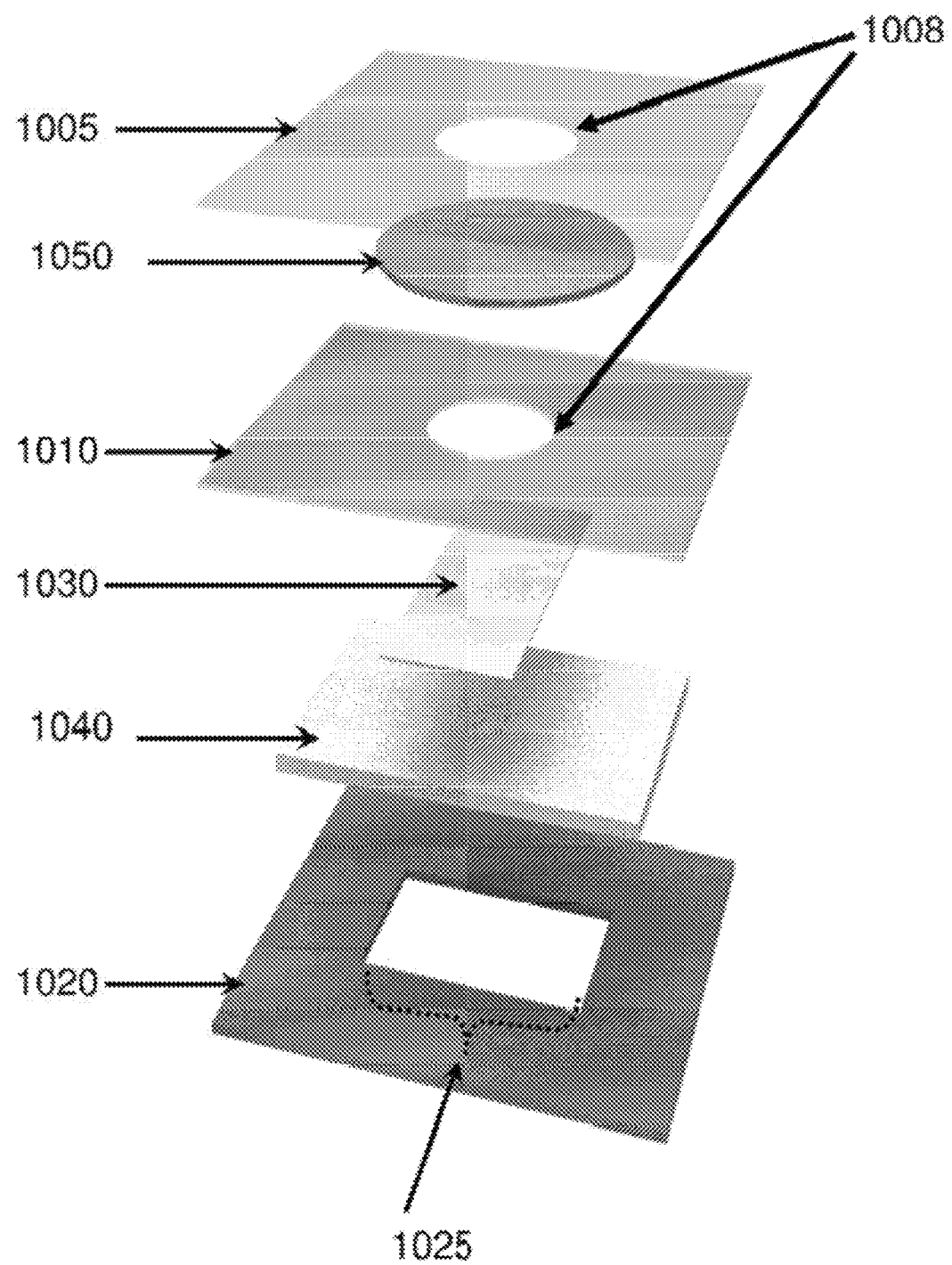
FIG. 19 depicts one type of analyte detection membrane system for a representative device according to some embodiments of the present invention.

In some embodiments of a device that can be used to detect multiple analytes with a single signal, the devices described herein are placed in a container. In some embodiments, the container is a pouch or a bag. In some embodiments, the container comprises an inlet. In some embodiments, the container comprises a removable or movable member or layer that when moved or removed exposes the inlet allowing the sample to be applied to the analyte detection membrane system. Examples of a removable or movable member or layer includes, but is not limited to, a flap or tab. A flap or tab, for example, is shown in FIGS. 18 and 19. In some embodiments, the removable layer or movable layer can also act as a seal for the container. The seal can protect the conjugate pad and/or the analyte detection membrane system.

In some embodiments of the devices and systems described herein, the removable or movable layer is in contact with or attached to the conjugate pad.

In some embodiments of a device that can be used to detect multiple analytes with a single signal, a device for detecting an analyte comprises a first outer member and a second outer member comprising a first inner member and a second inner member, wherein the first inner member and second inner member are in contact with each other. In some embodiments, the first outer member comprises an inlet. In some embodiments, the first inner member comprises an inlet. In some embodiments, the first outer member and the first inner member comprise an inlet. In some embodiments, between the first and second inner members is an analyte detection membrane system. In some embodiments, the device comprises a conjugate pad. In some embodiments, the device lacks a conjugate pad. In some embodiments, the analyte detection membrane system comprises a test membrane and an absorbent member and optionally a conjugate pad. In some embodiments, the analyte detection membrane system comprises in the following order a test membrane and an absorbent member. In some embodiments, at least a portion of each of the optional conjugate pad, test membrane, and absorbent member are substantially parallel to each other. In some embodiments, as discussed above, the analyte detection membrane system is compressed between the first inner member and second inner member. In some embodiments, the device and/or system comprises an adhesive member as described herein. In some embodiments, the device comprises a filtration membrane. In some embodiments, the filtration membrane can be within the analyte detection membrane system. In some embodiments, the a first surface of the filtration membrane contacts a surface of the first inner member and a second surface of the filtration membrane contacts another membrane or member of the analyte detection membrane system. In some embodiments, a second surface of a filtration membrane contacts a surface of a test membrane. The filtration membrane can be any material as described herein. For example, the filtration membrane, in some embodiments, can be the same materials that can be a conjugate pad, test, membrane, absorbent member, and the like. In some embodiments, the filtration membrane is a glass fiber pad.

In some embodiments of a device that can be used to detect multiple analytes with a single signal, where the conjugate pad is not present within the device or the system, the conjugate is supplied as a liquid or as a material that can be dissolved in a liquid (e.g. water, buffered solution, saline, and the like). The conjugate can be supplied in a separate container (e.g. tube) and be provided with a device or system described herein. Where the conjugate is supplied in a container the conjugate is incubated with the sample before the sample is applied to the analyte detection membrane system. The sample can be produced by any method and/or as described herein. For example, a piece of meat can be swabbed or wiped and to produce a test sample. The test sample can then be incubated or contacted with the conjugate to produce a test sample-conjugate mixture. This mixture can then be applied to the analyte detection membrane system as described herein using a device and/or system as described herein. In some embodiments, the test sample-conjugate mixture is applied directly to the test membrane. In some embodiments, the test sample-conjugate mixture is filtered or passes through another membrane prior to contacting the test membrane.

In some embodiments of a device that can be used to detect multiple analytes with a single signal, the analyte detection membrane system is compressed between the first and second inner members. In some embodiments, the analyte detection membrane system is compressed between a plane formed by the first inner member and a plane formed by the second inner member wherein the planes formed by the first inner member and the second inner member are substantially parallel to each other and the analyte detection membrane system. In some embodiments, the planes are parallel to each other and the analyte detection membrane system. In some embodiments, the planes are substantially parallel to the first and second outer members.

In some embodiments of the devices described herein and throughout, the conjugate pad is not compressed by the first and second inner members or by the force members described herein.

In some embodiments of a device that can be used to detect multiple analytes with a single signal, the first outer member comprises a removable or movable tab. In some embodiments, the conjugate pad is attached to said first outer member. In some embodiments, the conjugate pad is attached to the removable or movable tab. In some embodiments, the first outer member and second outer member form a container and the container encapsulates the first and inner second member. In some embodiments, the container is a pouch, bag (e.g. sealable (e.g. zipper, adhesive, and the like) or any other type of container that can encompass the analyte detection membrane system and that is compressed between the first and second inner members.

In some embodiments of a device that can be used to detect multiple analytes with a single signal, the container comprises a removable or movable tab. The removable or movable tab can be any shape and can be completely removable or removed to an extent that exposes the inlet. In some embodiments, the tab when moved or removed removes or moves the conjugate pad. The conjugate pad can be moved, for example, a sufficient distance so that the results of the test membrane can be analyzed (e.g. visualized).

In some embodiments of a device that can be used to detect multiple analytes with a single signal, a first surface of the conjugate pad is in contact with the first outer member and a second surface of the conjugate pad is in contact with the first inner member.

In some embodiments of a device that can be used to detect multiple analytes with a single signal, the first and second inner members are attached to one another along an edge of the first inner member that is parallel to an edge of the second inner member. In some embodiments, the first and second inner members are attached by a spring, hinge, and the like. The manner by which the first and second inner members are attached is not limited and can be by any structure that enables the analyte membrane system to be compressed between the first and second member. In some embodiments, the first and second inner members are contiguous with one another and form, for example, a clip. Examples of clips are shown throughout the present application. The clip, can be for example, cut from metal or other type of material that allows the first inner member to be flexible such that the analyte detection membrane system can be inserted between the first and second members. In some embodiments, the first inner member is removable.

As discussed herein, the devices and systems can comprise a removable or movable layer (e.g. tab). The removable or movable layer can be removed or moved by manual force, such as, but not limited to, pealing or tearing. The removable or movable layer can also be removed or moved by mechanical force. The manner by which the removable or movable layer is moved can by any means. Examples of a removable or movable layer includes but is not limited to, tabs, flaps, and the like. As discussed herein, this flap or tab can act as a seal and the like.

As discussed herein, the conjugate pad can comprise an analyte specific capture reagent. In some embodiments, the conjugate pad comprises a plurality of analyte specific capture reagents. In some embodiments, the conjugate pad comprises 1, 2, 3, 4, or 5 analyte specific capture reagents. The analyte can be any molecule that can be specifically recognized by a capture reagent. Examples of analytes include a polynucleotide molecule (e.g. DNA, RNA, siRNA, antisense oligonucleotide) a peptide, a protein, a saccharide, a polysaccharide, a carbohydrate, and the like. The antigen can also refer to different epitopes present on the same protein or polypeptide. The analyte can also refer to antigens from pathogenic or non-pathogenic organisms.

In some embodiments of a device that can be used to detect multiple analytes with a single signal, the devices may be housed singly, in pairs, or in multiple configurations. The housing can be watertight to prevent leakage and can be manufactured from a variety of inert materials, such as polymer materials. The inlet, in some embodiments, can be of sufficient volume to contain any required amount of sample or reagents to be used with the invention.

Because the membranes, members, or pads of the device are, in some embodiments, chemically inert, they may have to be activated at any reaction site where it is desired to immobilize a specific binding reagent against solvent transport. Various methods may be required to render the reagent immobilized according to the particular chemical nature of the reagent. Generally, when the media is nitrocellulose or a mixed nitrocellulose ester, no special chemical linkage is required for the immobilization of reagents. Various techniques may be used for other materials and reagents which include functionalization with materials such as carbonyldiimidazole, glutaraldehyde or succinic acid, or treatment with materials such as cyanogen bromide. Other suitable reactions include treatment with Schiff bases and borohydride for reduction of aldehyde, carbonyl and amino groups. DNA, RNA and certain antigens may be immobilized against solvent transport by baking onto the chromatographic material. Baking may be carried out at temperatures ranging from about 60° C. to about 120° C. for times varying from about five minutes to about 12 hours, and in some embodiments, at about 80° C. for about two hours.

Embodiments described herein also provide systems comprising the devices described herein and a buffer container. The systems can be used to detect multiple analytes with a single signal. The buffer container can be any buffer that the sample that is being tested can be mixed with and then applied to the device. For example, the sample can be taken from a source and the sample can be mixed with the buffer. The buffer can be a lysis buffer that will lyse the cells or a buffer that maintains the pH of the sample so that the analysis can be done properly. The buffer container can be any shape and can be included outside or inside the housing of the device.

In some embodiments, a system is provided that comprises a sample collector. The sample collector can be any material that can take a sample from a source and allow the sample to be tested. For example, the sample collector can be a swab, such as a cotton-swab. In some embodiments, the sample collector is an inoculator. In some embodiments, the housing comprises the sample collector and a portion of the sample collector is in the inside of the housing. In some embodiments, the sample collector is partially outside and partially inside the housing. In some embodiments, the sample collector is completely outside the housing.

Kits for detecting multiple analytes with a single signal is also provided, wherein the kits comprise a device described herein. The kit can include a device as described herein, a sample collector, a buffer container, an instruction manual, a positive control, a negative control, or any combination thereof. With respect to the kit, a positive control is a sample that is known to contain the analyte(s) that can be detected with the device present in the kit. In contrast the negative control, would not contain an analyte that can be detected by the kit. For example, the negative control when used in conjunction with the anti-antibody would be able to demonstrate that the device is working properly.

Buffers can also be included in the present invention. Examples of buffers include, but are not limited to, 1×PBS (10 mM Phosphate, 137 mM Sodium Chloride, 2.7 mM Potassium Chloride), a wash buffer (e.g. 10 mM Sodium Phosphate, 150 mM NaCl, 0.5% Tween-20, 0.05% Sodium Azide), a membrane buffer (e.g. 10 mM Sodium Phosphate, 0.1% Sucrose, 0.1% BSA, 0.2%, PVP-40 pH 7.21, filtered with 0.2 µm filter.), Polyclonal Conjugate Block Buffer (e.g. 50 mM Borate, 10% BSA, pH 8.93); Polyclonal Conjugate Diluent (e.g. 50 mM Borate, 1% BSA, pH 9.09), or Blocking Buffers (e.g. 10 mM Sodium Phosphate, 0.1% Sucrose, 0.025% Silwet pH 7.42; 10 mM Sodium Phosphate, 1% Sucrose, 1% Trehalose, 0.01% BSA, 0.025% Tween-20; 0.05% Sodium Azide, 0.025% Silwet pH 7.4; 10 mM Sodium Phosphate, 0.1% Sucrose, 0.1% BSA, 0.2% PVP-40 pH 7.21). The buffer can also be, but is not limited to, a blocking buffer (e.g. 10% BSA in deionized water, pH 7.4 or 1% BSA in deionized water, pH 7.4); 10 mM Borate, 3% BSA, 1% PVP40, and 0.25% Tween-100; and the like.

The conjugate pad and the test membrane can be contacted with any of the buffers described herein either in the presence or absence of a capture reagent and, in some embodiments, allowed to dry.

Examples of buffers that are lysis buffers include, for example, but are not limited to, 2% Tween (v/v) and 0.1% Triton (v/v); 2% Tween (v/v) and 0.1% SDS (w/v); 2% Tween (v/v) and 0.1% BSA (w/v); 2% Tween (v/v) and 1% BSA (w/v), 0.1% SDS (w/v), 1% BSA (w/v), or any combination thereof. The lysis buffers can also be, for example, 5% Tween/PBS; 2% Tween/PBS+0.1% SDS; 2% Tween/PBS+1% BSA. Other examples of lysis buffers include, but are not limited to, 5% Tween-80 (v/v); 5% Triton X-100 (v/v); 5% NP40 (v/v); 2% Tween-80 (v/v); 2% Triton X-100 (v/v); 2% NP40 (v/v); 1% Tween-80 (v/v); 1% Triton X-100 (v/v); and 1% NP40 (v/v). The detergents and other components of the buffers can be made with any suitable buffer suitable for proteins, and includes, but is not limited to, water and phosphate buffered saline. The lysis buffers can be used to prepare the samples prior to the samples making contact with the devices described herein. In some embodiments, a lysis buffer is not used. A lysis buffer is not used on a sample when a surface protein or surface analyte is desired to be detected in the method. Accordingly, in some embodiments, the sample is not subject to lysis or conditions that would cause a cell to be lysed. Where a cell is being used the cell could be part of the bridging complex and replace an amplicon that is shown, for example, in FIG. 3. The cell could be labeled or unlabeled so long as there is a capture reagent that can create a similar bridging complex.

The present subject matter also provides for methods of detecting multiple analytes comprising contacting a sample with a device and/or system as described herein, wherein the sample contacts the conjugate pad and the test membrane, wherein a positive reaction with the test membrane indicates the presence of the multiple analytes. In some embodiments, the conjugate pad comprises a signal detection unit or a capture regent that binds to the signal detection unit. In some embodiments, the test membrane comprises a second analyte-specific capture reagent. This can bind to an interaction unit present on the analyte. The sample can have, for example, the differentially labeled amplicons. For example, the test membrane can comprise a first capture reagent that binds to an interaction unit present on the first analyte. The conjugate pad can have a capture reagent that binds to the signal detection unit. The analytes can be incubated with the bridging unit and/or the signal detection unit prior to being applied to the device and contacting the conjugate pad and/or test membrane. A positive reaction is indicated when the complex of the analytes, capture reagents, and signal detection units are present. Otherwise the signal is not generated. A capture reagent can be applied to the test membrane so that it will indicate a positive reaction when it binds to its specific binding partner. The system and devices can be utilized to form the complexes described herein. For example, after a PCR reaction occurs that creates differentially labeled amplification products, the products are incubated with the antibodies that can be used to create the bridging complex. The incubation mixture is then added to the device. The sample flows through the conjugate pad that contains a capture reagent and then interacts with the test membrane that contains another capture reagent. In some embodiments, the conjugate pad is removed or moved so that the signal can be detected. Movement of the conjugate pad in a vertical flow device is described herein. If all of the analytes are present, the bridging complex is created and the single signal can be detected. The specific capture reagent on the test membrane can be applied in any manner such that when it is detected it can form a line, a circle, a plus sign, a broken line, an "X" or any other pattern. In some embodiments, the control line indicating that the device is working properly will cross the analyte specific line and when the multiple analytes are present and detected the detectable label will form a plus sign. The detection can be determined by the detection of the detection reagent as described herein and by routine methods known to one of skill in the art. Similar methods can be used, for example, in an ELISA system.

In some embodiments, a sample contacts the device, which is then followed by a buffer being applied to the device after the sample has contacted the device. For example, a sample comprising the analytes can be contacted with the conjugate pad such that the sample is transferred to the conjugate pad. Following the contact with the conjugate pad a separate solution can be applied to the device to facilitate or initiate the vertical flow through the devices described herein.

In some embodiments, as described herein, the capture reagent is an antibody. In some embodiments, the sample that is tested is a solution but can also be a mixture of solution or buffer and solid material that can be applied to the device. The solution will then solubilize the analyte(s) and allow the conjugate pad's capture reagent to come into contact with the appropriate analyte present in the sample. In some embodiments, the sample comprises a cell lysate. In some embodiments, the cell lysate has been clarified by centrifugation or other means to remove non-soluble materials.

In some embodiments, the methods comprise contacting a test sample with a sample collector and contacting the sample collector with the device. The test sample can be a sample comprising amplicons which are created from multiple analytes. In some embodiments, the methods comprise contacting the sample collector with a solution or buffer, wherein the solution or buffer is applied to the device. In some embodiments, the samples are contacted with the conjugate pad prior to the sample coming into contact with the test membrane. In some embodiments, the sample is contacted with the conjugate pad and the test membrane simultaneously.

In some embodiments, the method comprises moving the conjugate pad of the devices described herein, wherein the movement of the devices exposes the test membrane for detection. In some embodiments, the locking member moves the conjugate pad. In some embodiments, the conjugate pad is attached to the locking member and/or the sliding button member. In some embodiments, movement or removal of the removable member moves or removes the conjugate pad. In some embodiments, the conjugate pad is attached to the removable member and/or the adhesive member. In some embodiments, when the removable member is moved or removed the adhesive member is also moved with respect to its original position or removed from the device. The analyte can be those that are discussed herein or any other analyte that can be detected using the methods and devices described herein. In some embodiments, the method comprises applying the sample to the device and allowing the sample to flow through the device via vertical flow.

In some embodiments the detection or indication of the presence or absence of multiple analytes occurs in less than 60 seconds. In some embodiments, the detection or indication of the presence or absence of multiple analytes occurs in about 30 to about 60 seconds. In some embodiments, the detection or indication of the presence or absence of multiple analytes occurs in less than 2 minutes. In some embodiments, the detection or indication of the presence or absence of multiple analytes occurs in about 30 seconds.

In some embodiments, devices for detecting multiple analytes with a single signal are provided. In some embodiments, the device comprises a housing. The device can comprise a first housing member and a second housing member to form the housing. In some embodiments, the first and second housing members are separate members. The first and second housing members can be manufactured as a single piece. The single piece, in some embodiments, can be separated into the two housing members to allow for the introduction of the materials into the housing (e.g. device). In some embodiments, the device comprises an inlet. The inlet can be in either housing member (e.g. first or second housing member). The inlet can be oriented above the conjugate pad, such that a sample that is introduced into the device through the inlet contacts the conjugate pad prior to contacting the test membrane. The device is oriented such that regardless of any pressure being applied to the device, the sample will flow vertically down through the layers of membranes (e.g. analyte detection membrane system). Accordingly, in some embodiments, the second housing member comprises the inlet opening. In some embodiments, the second housing member is on top of the first housing member. The inlet can be any size or shape as described herein so long as the size and shape is sufficient for the introduction of a sample into the device such that the sample can contact the analyte detection membrane system.

The device can comprise one or more force members. The force members can apply pressure to the analyte detection membrane system. The force is applied perpendicular or substantially perpendicular to the membranes or layers of the analyte detection membrane system. In some embodiments, the device comprises at least 1, 2, 3, 4, or 5 force members. In some embodiments, the device comprises at least 1, 2, 3, 4, or 5 force members. In some embodiments, the device comprises a plurality of force members. The force members can be in contact with a housing member. In some embodiments, a first surface of the force member is in contact with a housing member (e.g. first or second housing member). In some embodiments, a second surface of the force member contacts the analyte detection membrane system. As described herein, the force member can be used to compress the analyte detection membrane system to facilitate the flow of the sample through the analyte detection membrane system. The pressure can facilitate the sample to flow vertically through the analyte detection membrane system. The force members can be oriented in the device independently of one another. The force members can also be manipulated such that each force member applies a pressure to a distinct analyte detection membrane system and that the force applied to each analyte detection membrane system is different or, in some embodiments, the same or substantially the same.

In some embodiments of a device that can be used to detect multiple analytes with a single signal, the device comprises one or more movable locking members. In some embodiments, the movable locking member contacts a force member. In some embodiments, the movable locking member contacts each force member present in the device. For example, in a device comprising a first and second force members, the movable locking member is in contact with the first force member and the second force member. The movable locking member, in some embodiments, supports the force member such that the force member is in a raised position. The raised position can be determined by comparing the force member's position when it is in contact with the movable locking member to when the force member is not in contact with the movable locking member. In the absence of contact between the force member and the movable locking member, the force member is in a first position. When the movable locking member is in contact with the force member, the force member is in a second position. In some embodiments, the second position of the force member is considered to be a raised position. The raised position can be used to compress the layers (e.g. membranes) of the analyte detection membrane system. When the movable locking member is not in contact with the force member, in some embodiments, the analyte detection membrane system is not compressed.

The device can comprise one or more movable locking members. In some embodiments, the device comprises a plurality of, or 1, 2, 3, 4, or 5 movable locking members. In some embodiments, the device comprises at least 1, 2, 3, 4, or 5 movable locking members. In some embodiments, the device comprises a number of movable locking members that is equal to the number of force members present in the device.

The movable locking members can also comprise a moving member, such as, but not limited to, a handle. The moving member can be used, for example, to turn or move the movable locking member such that the locking member contacts the force member. In some embodiments, the moving member disengages the locking members from the force member such that the force member changes positions (e.g. from a raised position to a lower position). The moving member can be used to relieve or apply the pressure being applied on the analyte detection membrane system. The moving member can also be used to relieve or apply compression of the analyte detection membrane system. In some embodiments, the moving member rotates the locking member around a central axis of the device. For example, after applying the sample to the device and the sample flows through at least one analyte detection membrane system, the moving member is moved, which rotates the movable locking member in either a clockwise or counterclockwise direction. The rotation of the movable locking member allows the force member to be lowered into a different position. The rotation of the movable locking member can also allow the pressure that is applied to the analyte detection membrane system to be relieved. In some embodiments, the pressure is completely relieved, or, in some embodiments, the pressure is only partially relieved.

In some embodiments of a device that can be used to detect multiple analytes with a single signal, the moving member that moves the movable locking member protrudes through the first or second housing member. In some embodiments, the moving member is accessible through the moving member outlet. In some embodiments, the moving member rotates around a central axis of the device when moved. In some embodiments, the moving member moves the movable locking member laterally (e.g. horizontally) or vertically. In some embodiments, the movable locking member moves laterally (e.g. horizontally) or vertically when moved.

The moving member and the movable locking member can be constructed as a single piece or as two pieces. In some embodiments, where the movable locking member and the moving member are two separate pieces and are constructed to interact with one another such that the movement of one moves the other. For example, one of the two pieces can have a "male member" that protrudes from the surface and inserts into the "female member" of the other piece to form the interaction.

The movement of the movable locking member by the moving member can also be used to move or remove the conjugate pad present in the analyte detection membrane system. As discussed herein, the conjugate pad can be removed to allow visualization or the analysis of the test membrane. The conjugate pad, as discussed herein, can be removed completely from the analyte detection membrane system or an amount that is sufficient to allow visualization or analysis of the test membrane. Analysis of the test membrane can be based solely upon visual inspection, or in some embodiments, an optical reader can be used to analyze the test membrane to determine the absence or presence of an antigen in the sample.

In some embodiments of a device that can be used to detect multiple analytes with a single signal, the device comprises a plurality, or two or more analyte detection membrane systems. In some embodiments, the device comprises at least 1, 2, 3, 4, or 5 analyte detection membrane systems. In some embodiments, the device comprises 1, 2, 3, 4, or 5 analyte detection membrane systems. The analyte detection membrane system can be as described herein and throughout the present application.

In some embodiments of a device that can be used to detect multiple analytes with a single signal, the device comprises one or more flexible or non-flexible attachment members. In some embodiments, the device comprises a plurality of flexible or non-flexible attachment members. In some embodiments, the device comprises at least 1, 2, 3, 4, or 5 flexible or non-flexible attachment members. In some embodiments, the device comprises 1, 2, 3, 4, or 5 flexible or non-flexible attachment members. In some embodiments, the flexible or non-flexible attachment member contact the movable locking member. In some embodiments, the flexible or non-flexible attachment member contact the movable locking member and the conjugate pad. The flexible or non-flexible attachment member can be used to remove or move the conjugate pad away from the rest of the layers (e.g. membranes) of the analyte detection membrane system. In some embodiments, the device comprises a number of flexible or non-flexible attachment members that is equal to the number of analyte detection membrane systems present in the device. In some embodiments, the device comprises a number of flexible attachment members that is equal to the number of force members present in the device. The flexible or non-flexible attachment members can also be used to retract the conjugate pad so as to reveal or expose a portion or all of the test membrane.

For example, in some embodiments, a device comprises three analyte detection membrane systems and three force members. A device with more than one analyte detection membrane system can be used to detect different analytes or different multiple analyte sets. In such a device, for example, the device comprises a first, second, and third attachment member. The first attachment member can be in contact with the conjugate pad of the first analyte detection membrane system and a movable locking member. Additionally, in some embodiments, the second attachment member can be in contact with the conjugate pad of the second analyte detection membrane system and a movable locking member. In some embodiments, the third attachment member can be in contact with the conjugate pad of the third analyte detection membrane system and a movable locking member. In some embodiments, the first, second, and third attachment members are in contact with the same movable locking member. In some embodiments, the first, second, and third attachment members are in contact with different movable locking members. For example, in some embodiments, the first and second attachment members are in contact with the same movable locking member and the third attachment member is in contact with a different movable locking member. Each attachment member is independently contacted with one or more movable locking members.

In some embodiments of a device that can be used to detect multiple analytes with a single signal, the movable locking member comprises one or more movable locking member extensions. In some embodiments, the movable locking member extensions contacts a force member. In some embodiments, the device comprises a number of movable locking member extension that is the same as the number of force members that are present in the device. In some embodiments, the movable locking member extension partially encircles or encompasses the force member. In some embodiments, the movable locking member extension completely encircles or encompasses the force member. The shape of the movable locking member or member extension can be any shape to keep the force member in a raised position. In some embodiments, the extension is a hook or hook-like shape that partially or completely encircles or encompasses the force member. The shape is not essential so long as the shape acts as a support for the force actuator (e.g. force member).

The number of movable locking member extensions can the same or different as the number of force members present in a device described herein. In some embodiments, a device comprises a plurality of movable locking member extensions. In some embodiments, a device comprises at least 1, 2, 3, 4 or 5 movable locking member extensions. In some embodiments, a device comprises 1, 2, 3, 4 or 5 movable locking member extensions. For example, in some embodiments, a device comprises a first, second, and third force members attachment members and a first, second, and third movable locking member extensions. In this non-limiting example, for example, the first force member contacts the first movable locking member extension, the second force member contacts the second movable locking member extension, and the third force member contacts the third movable locking member extension.

In some embodiments of a device that can be used to detect multiple analytes with a single signal, the movable locking member comprises an attachment member extension, which can be flexible or inflexible. In some embodiments, the attachment member extension contacts the attachment member. In some embodiments, the attachment member extension comprises an attachment member extension nodule. The nodule can be any shape or size that allows the attachment member to be secured to so that the attachment member securely maintains its contact with the movable locking member. In some embodiments, the one or more movable locking member extensions extend radially (e.g. outward) from the center of the movable locking member.

The number of attachment member extension can the same or different as the number of analyte detection membrane systems present in a device described herein. In some embodiments, a device comprises a plurality of flexible or non-flexible attachment member extensions. In some embodiments, a device comprises at least 1, 2, 3, 4 or 5 flexible or non-flexible attachment member extensions. In some embodiments, a device comprises 1, 2, 3, 4 or 5 flexible or non-flexible attachment member extensions. For example, in some embodiments, a device comprises a first, second, and third attachment members and a first, second, and third attachment member extensions. In this non-limiting example, for example, the first attachment member contacts the first attachment member extension, the second attachment member contacts the second attachment member extension, and the third attachment member contacts the third attachment member extension.

In some embodiments, the devices described herein comprise flexible and non-flexible attachment members and/or member extensions. Throughout the present disclosure, reference made be made to an attachment member or member extensions that are flexible or non-flexible. If one embodiment discloses a flexible member it is understood that another embodiment is also disclosed where the member is non-flexible unless context dictates to the contrary.

In some embodiments of a device that can be used to detect multiple analytes with a single signal, the device comprises a channel system. The channel system can be used to transport the sample (e.g. fluid) from the inlet opening of the device to the analyte detection membrane system(s) present in the device. As used herein, the "channel system" refers to the entire system regardless of how many individual channels are a part of the system. For example, the channel system can comprises two or more channels, such as, but not limited to, capillaries, that transport fluid from the inlet to an analyte detection membrane system. In some embodiments, the channel system comprises one or more branches (e.g. arms). The one or more branches can be transport fluid to one or more analyte detection membrane systems. In some embodiments, the channel system comprises 1, 2, 3, 4, or 5 branches. In some embodiments, the device comprises a number of branches in the channel system that is equal to the number of analyte detection membrane systems present in the device.

In some embodiments of a device that can be used to detect multiple analytes with a single signal, each branch of the channel system comprises capillary tubes that transport the fluid from the inlet to the analyte detection membrane system. In some embodiments, each branch comprises a plurality of capillary tubes. In some embodiments, each branch comprises at least 1, 2, 3, 4, or 5 capillary tubes. In some embodiments, the channel system does not comprise capillary tubes or tube-like formations but is made from a material that allows a portion of the sample to be transported from the inlet to the conjugate pad of the analyte detection system. In some embodiments, the channel system is a porous material that can be used to transport the sample from the inlet to the analyte detection membrane system. In some embodiments, the channel system is made from the same material as the conjugate pad. In some embodiments, the channel system and the conjugate pad are a contiguous piece of material. In some embodiments, the channel system comprises a Porex material. These porous materials allow the inlet to be in fluid communication with the analyte detection membrane system. In some embodiments, the porous material comprises polyethylene, polypropylene, polytetrafluourouethylene (PTFE), PVDF, ethyl vinyl acetate, Nylon 6, thermoplastic polyurethane (TPU), SCP, and the like. In some embodiments, the conjugate pad and the channel system are the same materials or different materials. In some embodiments, the channel system does not comprise a porous material and/or a capillary tube system.

In some embodiments of a device that can be used to detect multiple analytes with a single signal, the channel system contacts the inlet. In some embodiments, the channel system contacts the top of the analyte detection membrane system. In some embodiments, the channel system contacts the top of the conjugate pad or a membrane that is on top of the conjugate pad. In some embodiments, the channel system contacts an edge of the conjugate pad or an edge of a membrane that is on top of the conjugate pad. Regardless of how the sample contacts the analyte detection membrane system, in some embodiments, the sample flows vertically through analyte detection membrane system. Therefore, although the sample may flow horizontally (e.g. laterally) from the inlet to the analyte detection membrane system, the sample is not analyzed until it flows vertically through the analyte detection membrane system. This is distinctly different from lateral flow systems where a sample flows laterally (e.g. horizontally) through multiple membranes or test layers.

In some embodiments of a device that can be used to detect multiple analytes with a single signal, the channel system divides the sample into equal portions, wherein each equal portion contacts an independent analyte detection membrane system. In some embodiments, the channel system divides the sample into one or more unequal portions. The one or more unequal portions are then transported to independent analyte detection membrane systems.

For example, in a device that comprises a first and second analyte detection membrane systems the device comprises a channel system that comprises a first and second branch. In some embodiments, the first branch contacts the first analyte detection membrane system and the second branch contacts the second analyte detection membrane system. Upon application of the sample to the device (e.g. through the inlet opening), the sample is transported in equal portions through the first and second branches of the channel system to the first and second analyte detection membrane systems. In some embodiments, the sample is transported in unequal portions through the first and second branches of the channel system to the first and second analyte detection membrane systems. The sample can be divided into unequal portions, for example, based upon the number of capillaries present in each branch. For example, the first branch can comprise more capillaries than the second branch. The greater number of capillaries will allow more of the sample to be transported through the first branch than the second branch, thereby delivering unequal portions to the first and second analyte detection membrane systems.

Accordingly, the branches of the channel system may have the same number of capillaries or different numbers of capillaries. The numbers of capillaries in each branch of the channel system is independent of each branch. That is each branch of the channel system can have the same number or a different number of capillaries as another branch. Therefore, in some embodiments, the device's channel system can be described as a capillary channel system. In some embodiments, the channel system is enclosed in a channel housing that is separate and distinct from the first and second housing members described herein for the device itself. In some embodiments, the channel housing is transparent, translucent, opaque, or partially translucent.

As discussed herein, the test membrane can be analyzed either visually with the human eye or through a machine, such as an optical reader to determine the presence or absence of multiple analytes with a single signal. In some embodiments, the analysis is done through a portal. In some embodiments, the device comprises one or more portals that are sufficient in size to allow visualization of a test membrane of one or more of the analyte detection membrane systems. In some embodiments, a single portal is used to visualize each of the test membranes present in the device. In some embodiments, the device does not comprise a portal. In embodiments, where the device does not comprise a portal, the test membrane can still be visualized by using a transparent or translucent housing for the device. In some embodiments, the first and/or second housing are transparent or translucent. Where the first and/or second housings are transparent or translucent this can allow an analyte detection membrane systems and its test membrane when it is revealed upon moving or removing the conjugate pad. In some embodiments, the device comprises a plurality of portals. In some embodiments, the device comprises at least 1, 2, 3, 4, or 5 portals. In some embodiments, the device comprises 1, 2, 3, 4, or 5 portals. In some embodiments, a device comprises 1 portal that is continuous and exposes each analyte detection membrane system present in the device to visual inspection.

As discussed herein, the force members can be allowed to move between at least two positions (e.g. raised or lowered; engaged or disengaged). In some embodiments, the force member is lowered and is encompassed by a force actuator outlet. Thus, in some embodiments, the device comprises one or more force actuator outlets that that can accept the force member as it is lowered. In some embodiments, the device comprises a plurality of force actuator outlets. In some embodiments, the force actuator outlet is a groove. In some embodiments, the force actuator outlet is a circle or substantially circular. The force actuator outlet can be used to suspend the force actuator (e.g. force member) at a particular position. The force actuator outlet can also be used to retain the force actuator in a second position. In some embodiments, the circumference of the force actuator outlet is greater than the circumference of the portion of the force member that is entering the outlet. In some embodiments, the circumference of the force actuator outlet is greater than the largest circumference of the force member. In some embodiments, the circumference of the force actuator outlet is not greater than the largest circumference of the force member, wherein the force member has areas with at least two different circumferences. For example, force members are described herein that would have two different circumferences. A force member can comprise a cap with one circumference and a support structure that supports the cap with a different circumference. The support structure can, in some embodiments, have a smaller circumference than the cap. In some embodiments, the force actuator outlet can have a circumference that is larger than the support structure circumference, but smaller than the cap structure circumference. In some embodiments, the number of force actuator outlets is the same or different than the number of the force members present in a device.

The force actuator outlet can also be a continuous depression in a housing member that can accept each and every force member in the device when it is lowered and no longer compressing the analyte detection membrane system. The outlet can be used to temporarily house the force member or it can be permanent, such that the force member cannot be raised again to compress or further compress the analyte detection membrane system.

As discussed herein and throughout the present application, the conjugate pad, permeable membrane, test membrane, and absorbent member can be or are compressed by the force member under certain forces as described herein and including, but not limited to a force from about 1 lbf to about 100 lbf. In some embodiments, where there are multiple analyte detection membrane systems, the pressure applied to each membrane detection system can be different or it can be the same. For example, in a device that has a first, second, and third analyte detection membrane system, the first analyte detection membrane system can be compressed under a force of 5 lbf, the second analyte detection membrane system can be compressed under a force of 10 lbf, and the third analyte detection membrane system can be compressed under a force of 25 lbf. In another example, in some embodiments, the first and second analyte detection membrane systems are compressed under the same pressure and the third analyte detection membrane system is compressed under a pressure that is different from the first and second analyte detection membrane systems. The differences in pressure can be used to use different flow rates, which can be useful for different analytes. The pressure is correlated with the flow rate. The pressure can be manipulated by the position of the force member and how much the layers of the analyte detection membrane system are compressed. The specific force used can be determined and measured by one of skill in the art using known and routine methods.

As described herein, in some embodiments, the present invention provides a system comprising any device described herein, a buffer container and/or a sample collector. In some embodiments, the present invention provides a kit comprising any device described herein and one or more of a positive control, a negative control, an instruction booklet, a buffer container, and/or a sample collector, or any combination thereof.

The methods described herein can be used with a device that has, for example, a plurality, two or more, analyte detection membrane systems. The methods can be also be used with devices that have 2, 3, 4, or 5 analyte detection membrane systems. Where there are more than two analyte detection membrane systems (e.g. 3, 4, 5, 6, 7, 8, 9, or 10) the methods and the descriptions contained herein are modified to be consistent with the number of analyte detection membrane systems. These changes are made in accordance with the descriptions contained herein and any routine changes that would be known by one of skill in the art. The changes to encompass more than 2 analyte membrane detections systems based upon the descriptions contained herein combined with knowledge of one of skill in the art would not require undue experimentation. In some embodiments as described herein, the device comprises two or more analyte detection membrane systems. In some embodiments, the method comprises contacting a sample (e.g. the sample comprising multiple analytes) with the device and a portion of the sample being transported through a channel system to the conjugate pads of the two or more analyte detection membrane systems. In some embodiments, the method comprises detecting a positive or negative reaction for the analytes, wherein a positive reaction indicates that the presence of the multiple analytes. In some embodiments, the two or more analyte detection membrane systems are compressed by the force member. In some embodiments, the sample vertically flows from the conjugate pad to the test membrane. In some embodiments, the method further comprises compressing the analyte detection membrane system by the force member. In some embodiments, the method comprises moving the conjugate pad of the two or more detection systems after a portion of the sample has contacted and flowed through the conjugate pad, thereby exposing the test membrane for analysis. In some embodiments, the test membrane is exposed within the portal opening for detection. In some embodiments, the conjugate pad of the two or more detection systems is moved by moving the movable locking member. In some embodiments, the moving the movable locking member comprises rotating the movable locking member around the central axis of the device. In some embodiments, the movable locking member is moved laterally or vertically. In some embodiments, the moving lockable member moves the conjugate pad of the two or more detection systems simultaneously or sequentially. In some embodiments, the method further comprises relieving the compression of the two or more analyte detection systems. The pressure can be relieved or lessened, for example, by moving the movable locking member. In some embodiments, the movable locking member is moved (e.g. rotated) by turning or moving the moving member that is connected to the movable locking member.

In some embodiments, one or more of the analyte detection membrane systems are compressed prior to the sample contacting the channel system. In some embodiments, one or more of the analyte detection membrane systems are compressed prior to the sample coming into contact with the conjugate pad of the one or more of the analyte detection membrane systems. In some embodiments, each of the analyte detection membrane systems is compressed simultaneously. In some embodiments, each of the analyte detection membrane systems is compressed independently. In some embodiments, each of the analyte detection membrane systems present in a device is compressed prior to a sample coming into contact with the conjugate pad.

In some embodiments, the method comprises relieving the pressure applied by a force member on the two or more analyte detection membrane systems, wherein said force member moves vertically or horizontally to relieve said pressure. In some embodiments, the method comprises the force member moving from a first position to a second position to relieve the pressure. In some embodiments, the force member moves into or comes into contact with a force actuator outlet when the movement of the force member relieves or reduces the pressure or relieves or reduces the force being applied to the analyte detection membrane system. In some embodiments, the force member drops partially or completely out of the device.

In some embodiments of a device that can be used to detect multiple analytes with a single signal, the present invention provides a device for detecting an analyte comprising a pressure actuator, a pressure release, an analyte detection membrane system, an analyte detection membrane system receptacle, and an outlet. In some embodiments, the analyte detection membrane system receptacle is of sufficient size and shape to accept the analyte detection membrane system. In some embodiments, the receptacle is a groove. In some embodiments, the receptacle is a case that can be, but not necessarily, removed from the device.

In some embodiments, the analyte detection membrane system, as described herein, can be encompassed or contained within a cartridge or housing. The housing can comprise a first and/or second housing member. In some embodiments, where the analyte detection membrane system is contained within a housing or a cartridge, the receptacle is of sufficient size and shape to accept the housing or the cartridge. In some embodiments, the housing or cartridge comprises an inlet. The inlet can be used to apply the sample to the analyte detection membrane system. In some embodiments, the cartridge or housing comprises a second outlet that allows the sample to flow through and out of the housing and cartridge. The analyte detection membrane system can be any analyte detection membrane system as described herein.

In some embodiments of a device that can be used to detect multiple analytes with a single signal, the device comprises a pressure actuator. The pressure actuator, for example, can be the force member that is described in herein. In some embodiments, the pressure actuator is an air valve or vacuum valve that either applies air pressure to the analyte detection membrane system or draws a vacuum through the analyte detection membrane system. In some embodiments, the pressure actuator can be regulated by a pressure release or pressure regulator. The pressure release or pressure regulator can be, for example, a vacuum release. The release or regulator can be used to regulate the pressure or vacuum being applied to the analyte detection membrane system. The pressure or vacuum can be applied to the analyte detection membrane system through an outlet or tube that is present in the device. The outlet can be the same outlet present in the cartridge or housing described herein or it can be a different outlet or tube. The outlet or tube can be used so that the pressure or vacuum to be applied with specificity rather than allowing it to diffuse across the entire device.

In some embodiments, the housing (e.g. cartridge) encasing the analyte membrane detection comprises an upper housing and a lower housing. In some embodiments, the housing comprises a plurality of membrane or pad holders. In some embodiments, the housing comprises one or more membrane or pad holders. In some embodiments, the housing comprises 1, 2, 3, 4, or 5 membrane or pad holders. In some embodiments, the housing comprises at least 1, 2, 3, 4, or 5 membrane or pad holders. In some embodiments, the housing comprises an inlet. In some embodiments, the housing comprises an outlet. In some embodiments, the vacuum actuator directly or indirectly contacts the housing outlet.

In some embodiments of a device that can be used to detect multiple analytes with a single signal, the device and any device described herein comprises an ejector for ejection the housing. The ejector can be used to facilitate the removal of the housing that contains the analyte detection membrane system. In some embodiments, the devices comprise a housing separator. The housing separator can be used to facilitate the separation of the housing. In some embodiments, the ejector can also act as the housing separator.

In addition to the methods described herein, in some embodiments, a method of detecting multiple analytes comprises applying a sample containing the multiple analytes to a device comprising a pressure actuator, a pressure regulator, an analyte detection membrane system, an analyte detection membrane system receptacle, and an outlet or any other device or analyte detection membrane system described herein. In some embodiments, the sample is contacted with the analyte detection membrane system, wherein the sample vertically flows through the analyte detection membrane system. In some embodiments, the method comprises detecting the presence or absence of the analyte. This can be done according to the bridging complex that is formed through the use of the interaction units, capture reagents, and signal detection units described herein.

In some embodiments of using the devices to detect multiple analytes, detecting comprises removing or moving the conjugate pad present in the analyte detection membrane system a sufficient amount to visualize the result, wherein a positive result indicates the presence of the multiple analytes. In some embodiments, detection comprises removing the analyte detection membrane system from the device and further removing or moving the conjugate pad a sufficient amount to visualize the detection of the analyte or multiple analytes with a single signal. In some embodiments, the analyte detection membrane system is contained within a housing or cartridge, and therefore, in some embodiments, the housing or cartridge is removed from the device prior to the movement or removal of the conjugate pad. In some embodiments, the housing is separated into a first (e.g. upper) and a second (e.g. lower) housing prior to the removal or movement of the conjugate pad as described herein. In some embodiments, the separation of the housing into a first and a second housing removes or moves the conjugate pad to visualize the test membrane as described herein. In some embodiments, the housing is separated manually and/or mechanically. In some embodiments, the housing (e.g. cartridge) is ejected from the device. In some embodiments, the housing is ejected from the device by an ejector. In some embodiments, the housing is separated by a separator. In some embodiments, the ejector also functions as a separator.

In some embodiments, the method comprises applying pressure on or drawing a vacuum through an analyte detection membrane system. In some embodiments, the method comprises releasing or reducing the pressure or the vacuum. In some embodiments, the pressure or vacuum is released or reduced by using the pressure regulator. In some embodiments of the methods described herein, the sample that is contacted with the analyte detection membrane system flows through the analyte membrane system at a flow rate that is regulated by a pressure actuator. In some embodiments, the entire sample flows through the analyte detection membrane system at a constant rate. In some embodiments, the sample flows through the analyte detection membrane system at a variable rate. In some embodiments, the variable rate comprises at least one period of time where the flow rate of a portion of the sample is 0. For example, the pressure being applied or vacuum being drawn can be regulated such that the sample stops flowing through the analyte detection membrane system for a period of time. This can be referred to as a "dwell." As described elsewhere in the present document, the dwell can be implemented by placing impermeable or slightly impermeable membranes between the conjugate pad and the other layers of the analyte detection membrane system. The dwell, however, can also be regulated by regulating (e.g. changing) the pressure that is applied to the analyte detection membrane system. The dwell can also be regulated by regulating (e.g. changing) the vacuum that is being drawn through the analyte detection membrane system. Any method of regulating the flow rate through the analyte detection membrane system, including but not limited to, the flow rate through the conjugate pad and/or the test membrane can be used.

The devices herein, can also be automated or used in conjunction with an optical reader or other type of spectrometer. The advantages of combining the systems and devices described herein with an optical reader or other type of spectrometer is that the sensitivity of the devices and assays can be increased such that less analyte present in the sample is necessary to identify a sample as being positive for that analyte. This greater sensitivity can be then be used, for example, to determine if food contains pathogens, a person has a certain disease or condition, or if a product has an analyte that is otherwise undetectable using other devices and methods in the same amount of time it takes to use the presently described methods and devices.

Accordingly, in some embodiments of a device that can be used to detect multiple analytes with a single signal, the present invention provides a device for detecting multiple analytes comprising a sample inlet, an analyte detection cartridge receptacle, an analyte detection cartridge receptacle inlet, an optional conjugate pad remover, a pressure actuator, a spectrometer (e.g. optical reader), a display unit, a signal processing unit. The pressure actuator can be a force member whose position is modified to regulate the pressure being applied to the analyte detection membrane system that is used in conjunction with a device. The pressure actuator can also regulate the pressure by drawing a vacuum through the analyte detection membrane system that is used in conjunction with a device. The spectrometer can be any spectrometer that can detect the presence of a signal. The signal can be an optical signal. The signal can be a signal that is emitted in a spectrum chosen from, for example, infrared spectrum; near-infrared spectrum; visible spectrum, x-ray spectrum, ultra-violet spectrum, gamma rays, electromagnetic spectrum, and the like.

The spectrometer can be connected to the signal processing unit (e.g. computer). The signal processing unit can take the signal that is transmitted to it and analyze the signal to determine the presence or absence of the sample. An example of a signal processing unit is, but not limited to, a computer. The signal processing unit can programmed to analyze the signal transmitted by the spectrometer. The programming can implement an algorithm to analyze the signal to determine the presence or absence of an analyte in the sample. The algorithm can be based upon criteria that are pre-installed in the signal processing unit's memory or that are entered by the user of the device. The types of information that can be entered can be cut-offs for a positive or negative signal, processing times, and the like. The signal processing unit can also be used to regulate the pressure applied to or the vacuum drawn through the analyte detection membrane system.

The signal processing unit can be used or programmed to regulate the flow rate of the sample through the analyte detection membrane system. The flow rate can be regulated by regulating the pressure that is applied to or a vacuum that is drawn through the analyte detection membrane system. As described above with respect to the methods described herein, the sample that is contacted with the analyte detection membrane system flows through the analyte membrane system at a flow rate that is regulated by a pressure actuator. The pressure regulator can be in turn regulated by, for example, the signal processing unit. In some embodiments, the entire sample flows through the analyte detection membrane system at a constant rate, which is regulated by the signal processing unit. In some embodiments, the sample flows through the analyte detection membrane system at a variable rate, which is regulated by the signal processing unit. In some embodiments, the variable rate comprises at least one period of time where the flow rate of a portion of the sample is 0, which can be regulated by the signal processing unit. For example, the pressure being applied or vacuum being drawn can be regulated by the signal processing unit such that the sample stops flowing through the analyte detection membrane system for a period of time. As discussed herein, this can be referred to as a "dwell." The dwell, for example, can be regulated by regulating (e.g. changing) the pressure that is applied to the analyte detection membrane system, which can be implemented or controlled by the signal processing unit. The dwell can also be regulated by regulating (e.g. changing) the vacuum that is being drawn through the analyte detection membrane system, which can be implemented or controlled by the signal processing unit. Any method of regulating the flow rate through the analyte detection membrane system, including but not limited to, the flow rate through the conjugate pad and/or the test membrane can be used and such method can be regulated or implemented by the signal processing unit.

In some embodiments of a device that can be used to detect multiple analytes with a single signal, the devices described herein and throughout, comprises an analyte detection cartridge receptacle positioning member. The detection cartridge receptacle positioning member can be used, for example, to place the analyte detection membrane system in the proper position to accept the sample and/or for the sample to be analyzed. In some embodiments, the system is positioned for spectrometer analysis. The detection cartridge receptacle positioning member can be, in some embodiments, motorized and/or controlled by the signal processing unit. In some embodiments, the detection cartridge receptacle positioning member is not motorized but can controlled by a manual controller, such as, but not limited to a lever or screw that allows that receptacle's position to be modified. In some embodiments, the signal processing unit controls the movement of the analyte membrane detection receptacle by moving the analyte membrane detection receptacle moving member. In some embodiments, the analyte detection cartridge receptacle positioning member is in contact with analyte detection cartridge receptacle.

In some embodiments of a device that can be used to detect multiple analytes with a single signal, the devices described herein can comprise a waste receptacle. The waste receptacle can be in the interior of the device or outside but still contacting the device. The waste receptacle can accept analyte detection membrane systems that have been used. In some embodiments, as described herein, the analyte detection membrane system is contained in a housing (e.g. cartridge). The housing can then be ejected into the waste receptacle. The ejection can be manual or automated. In some embodiments, the ejection is controlled by a signal processing unit. In some embodiments, the signal processing unit controls an ejector that ejects the analyte detection membrane system from the analyte detection membrane system receptacle into the waste receptacle. Like all of the devices described herein, in some embodiments, the device comprises an analyte detection membrane system, which can or cannot be encased in a housing (e.g. cartridge).

In some embodiments of a device that can be used to detect multiple analytes with a single signal, the pressure actuator contacts the analyte detection membrane system. In some embodiments, the pressure actuator is attached to the device at a point that allows movement of the pressure actuator. In some embodiments, the pressure actuator is attached at a pivot point that allows the pressure actuator to pivot at a single contact point.

In some embodiments, the devices described herein comprise a display. In some embodiments, the display is an electronic display. In some embodiments, the signal processing unit receives an input from the spectrometer and displays information on the display unit. The display unit can be display various information, including but not limited to, the presence and/or absence of one or more analytes, status, and the like.

In some embodiments, the present invention comprises detecting the multiple analytes using a device comprising a signal processing unit or a device described herein. In some embodiments, the method comprises contacting the device with a sample that contacts the analyte detection membrane system within the device. The sample then flows through the analyte detection membrane system. In some embodiments, the method comprises detecting the presence or absence of the analyte. In some embodiments, the detecting comprises the optical reader detecting an optical signal from the analyte membrane system, the optical reader communicating the optical signal to the signal processing unit, the signal processing unit analyzing the optical signal to determine the presence or absence of the analyte; and the signal processing unit displaying a result on the display unit. The displayed result can be visual and/or audible. The signal analyzed can be a signal in a spectrum chosen from infrared spectrum; near infrared spectrum; visible spectrum, x-ray spectrum, ultra-violet spectrum, gamma rays, or electromagnetic spectrum. In some embodiments, the signal is in the near-infrared spectrum. In some embodiments, the method comprises ejecting the analyte detection membrane system into a waste receptacle. In some embodiments, the signal processing unit is a computer.

Referring to the drawings, in some embodiments, FIGS. 1 through 36 depict embodiments of devices, components of such representative devices, and various views of such embodied devices that can be used in the methods and/or in conjunction with or without other devices and/or systems described herein.

These devices described herein are non-limiting and any other device, including other vertical flow devices, can be used to detect multiple analytes according to the methods described herein using the bridging complexes that are created using the various labels and capture reagents.

Figure 8:
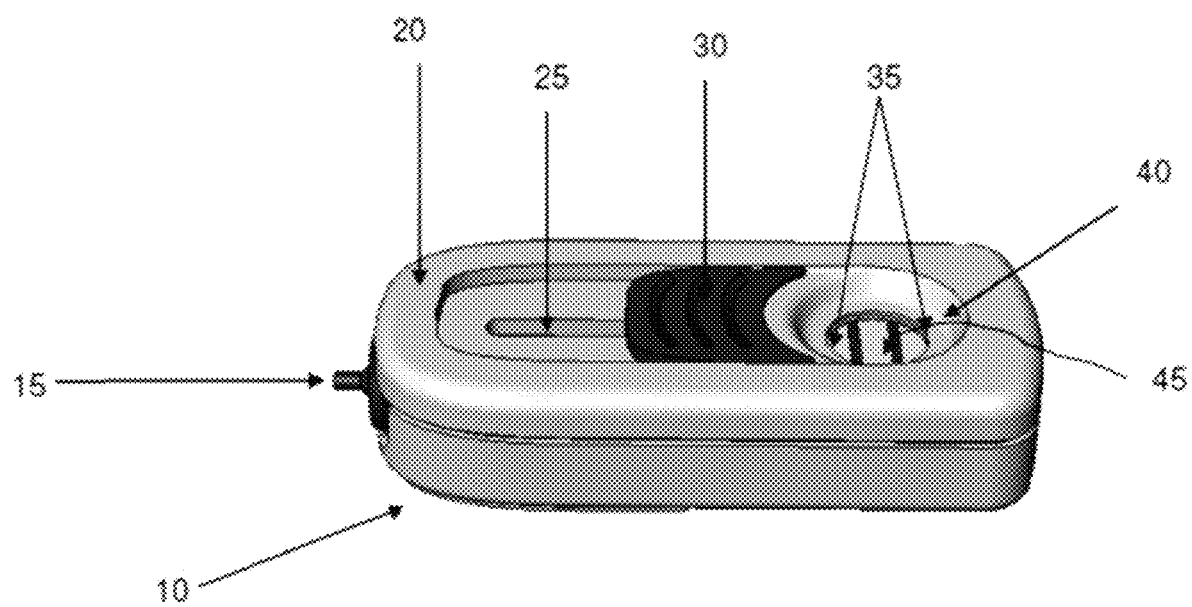
FIG. 8 depicts a perspective view of a representative device according to some embodiments of the present invention.

FIG. 8 depicts a device that can be used to detect multiple analytes with a single signal comprising a first housing member (10), a buffer container (15), a second housing member (20), a groove for the sliding button (25), a sliding button (30), an inlet opening (35), a collar (40), and a test membrane (45). FIG. 8 depicts a test membrane (45) comprising two capture reagents. The first (10) and second (20) housing members can also be referred to as the lower and upper housing members, respectively. In FIG. 1, the sample would be applied through the inlet opening (35) and can be allowed to vertically flow through to the test membrane (45). In FIG. 8, the groove (25) allows the sliding button to move, which when attached to the locking member moves the locking member and can, in some embodiments, move the conjugate pad and change the position of the force member.

Figure 9:
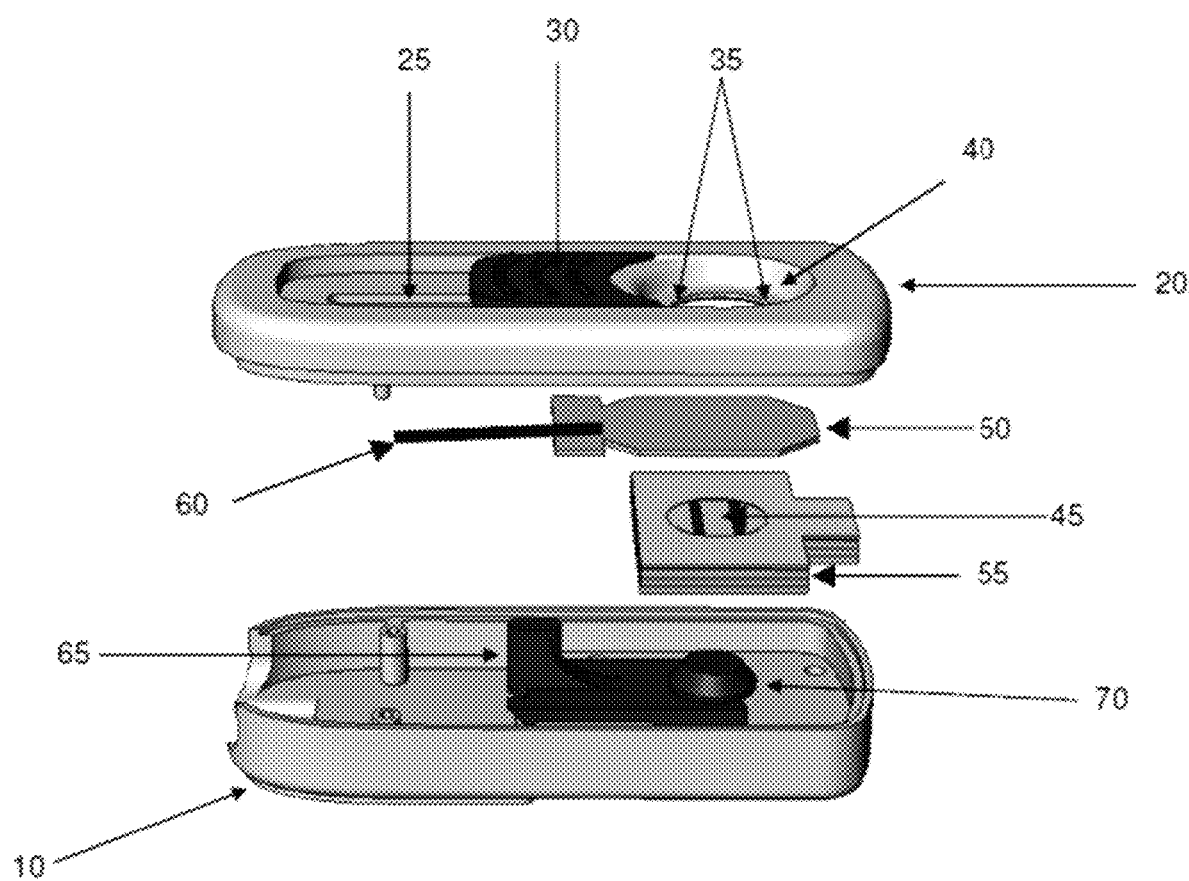
FIG. 9 depicts some components of a representative device according to some embodiments of the present invention.

FIG. 9 depicts a device that can be used to detect multiple analytes with a single signal comprising a first housing member (10), a second housing member (20), a groove for the sliding button (25), a sliding button (30), an inlet opening (35), a collar (40), a test membrane (45), a conjugate pad (50), a plurality of absorbent members (e.g. pads) (55), an attachment member (60), a locking member (65), and a force member (70). FIG. 9 depicts the conjugate pad (50), test membrane (45) and absorbent pad (55) arranged substantially parallel to one another. The force member (70) when in contact with the absorbent member would be applying pressure that is substantially perpendicular to the conjugate pad. As can be seen in FIG. 9, a sample that is contacted with the device through the inlet opening (35) would flow vertically through the conjugate pad (50) to the test membrane (45). Not explicitly shown in FIG. 9, but in some embodiments, a the permeable membrane is also substantially parallel to the conjugate pad (50) and to the test membrane (45), with a first surface of the permeable membrane contacting a surface of the conjugate pad (50) a second surface of the permeable membrane contacting a surface of the test membrane (45).

Figure 10:
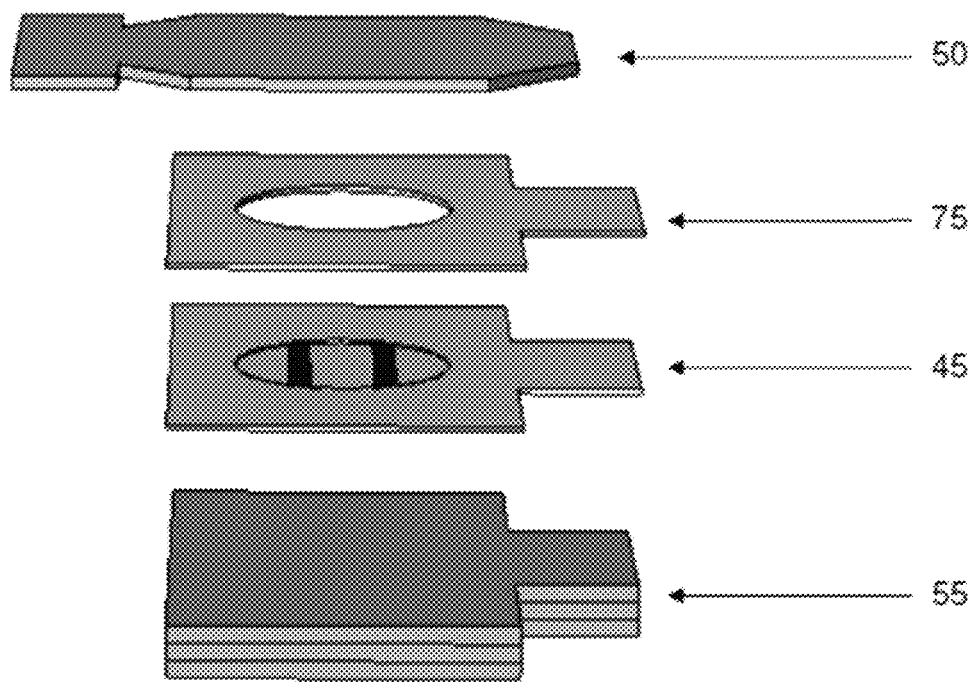
FIG. 10 depicts some components of a representative device according to some embodiments of the present invention.

FIG. 10 depicts a conjugate pad (50), a permeable membrane (75), a test membrane (45), and a plurality of absorbent members (55) that can be used to detect multiple analytes with a single signal. FIG. 10 depicts the components that can be used to detect multiple analytes with a single signal being substantially parallel with one another. FIG. 10 depicts the permeable membrane (75) comprising an opening. This opening can be used to allow visualization and detection of the test membrane's results.

Figure 11:
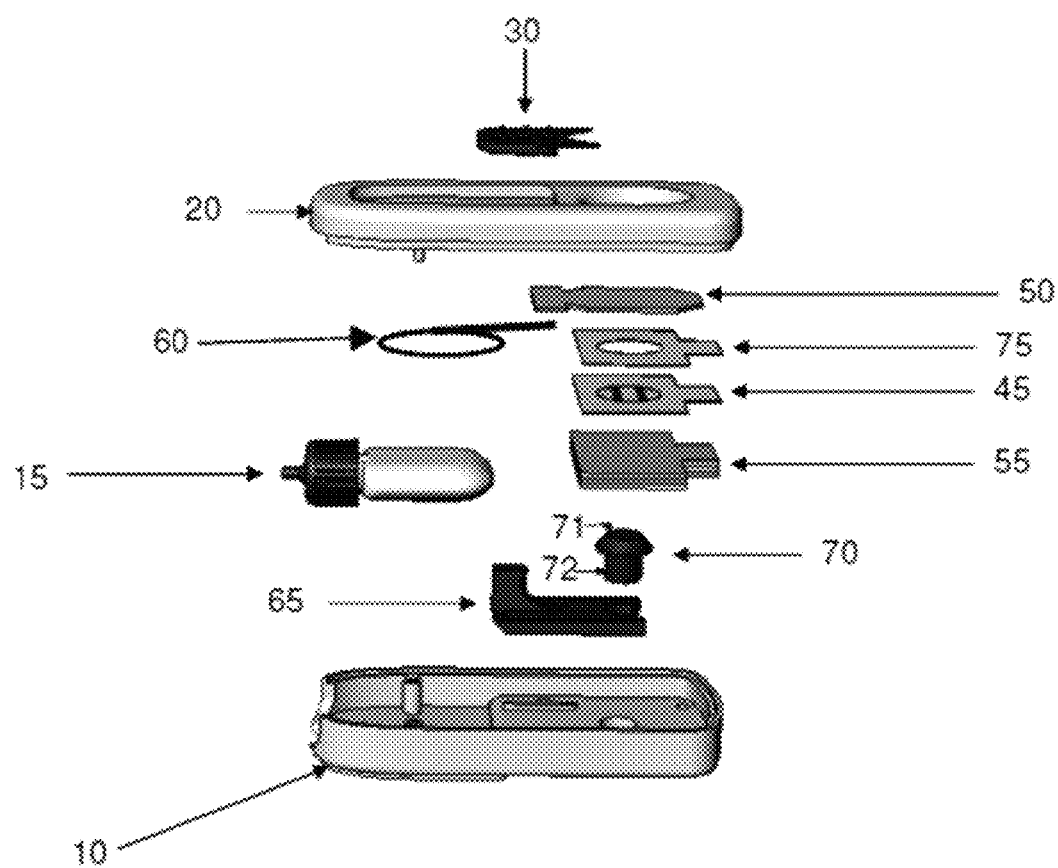
FIG. 11 depicts some components of a representative device according to some embodiments of the present invention.

FIG. 11 depicts a device that can be used to detect multiple analytes with a single signal comprising a first housing member (10), a buffer container (15), a second housing member (20), a sliding button (30), a test membrane (45), a conjugate pad (50), a permeable membrane (75), a plurality of absorbent members (e.g. pads) (55), an attachment member (60), a locking member (65), and a force member (70). FIG. 11 also depicts the force member (70) comprising a shaft (72) and a head (71) where the head (71) is wider than the shaft (72).

FIG. 12 depicts a partial view of a device that can be used to detect multiple analytes with a single signal comprising a first housing member (10), a locking member (65), a sliding button (30), and force member (70). FIG. 12 depicts the locking member (65) in contact with the force member (70) such that the force member (70) is in a raised method. FIG. 12 also depicts the movement of the locking member (65) and the sliding button (30) away from the force member (70) allowing the force member to change positions. In some embodiments, the change in position is that the force member is lowered.

Figure 13:
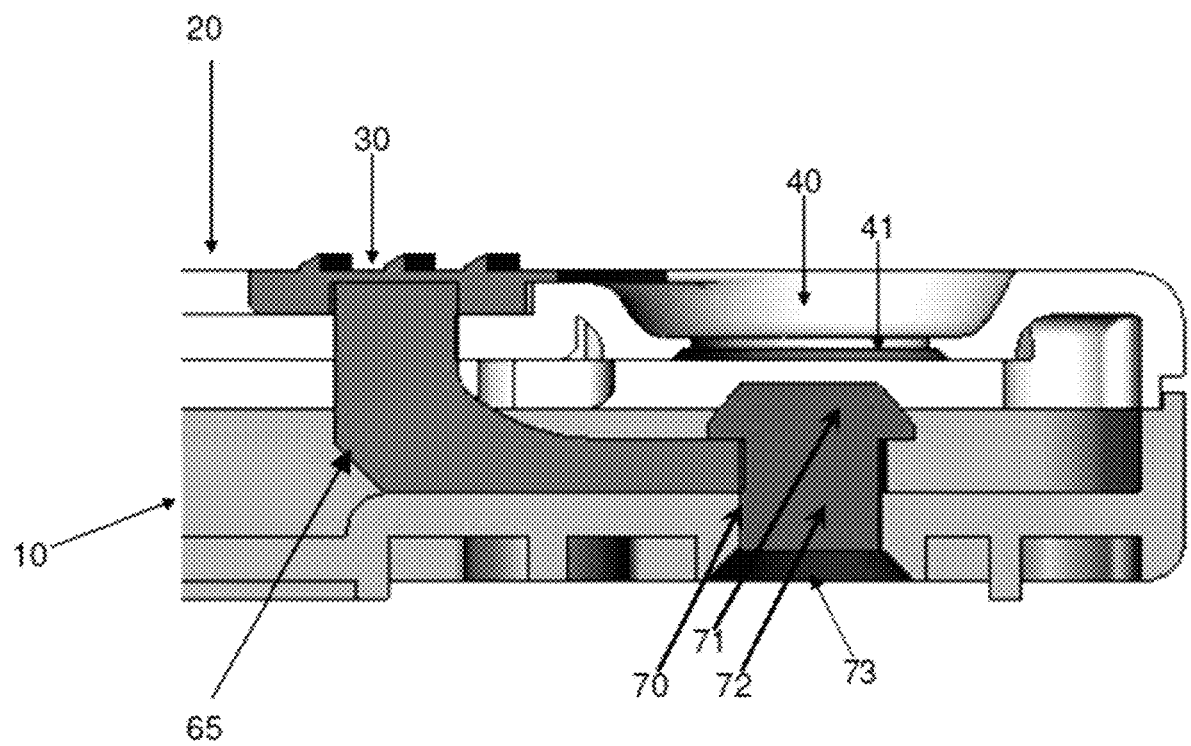
FIG. 13: Depicts a lateral view of some components of a representative device according to some embodiments of the present invention.

FIG. 13 depicts a side cut away view of a device that can be used to detect multiple analytes with a single signal comprising a first housing member (10), a second housing member (20), a sliding button (30), a locking member (65), a collar (40), an O-ring (41), a force member (70), and a support for the force member (73). The support for the shaft can be, for example, part of the first housing member (10) and is shaded differently for example purposes only. FIG. 13 depicts the button (30) in contact with the locking member (65) in such a way that movement of the button (30) will move the locking member (65). Movement of the locking member (65) will take away the support from the force member (70), which would allow the force member (70) to change positions. FIG. 13 also depicts the shaft (72) and the head (71) of the force member. The head (71) creates a lip where the locking member (65) can slide under and support the force member (70).

Figure 14:
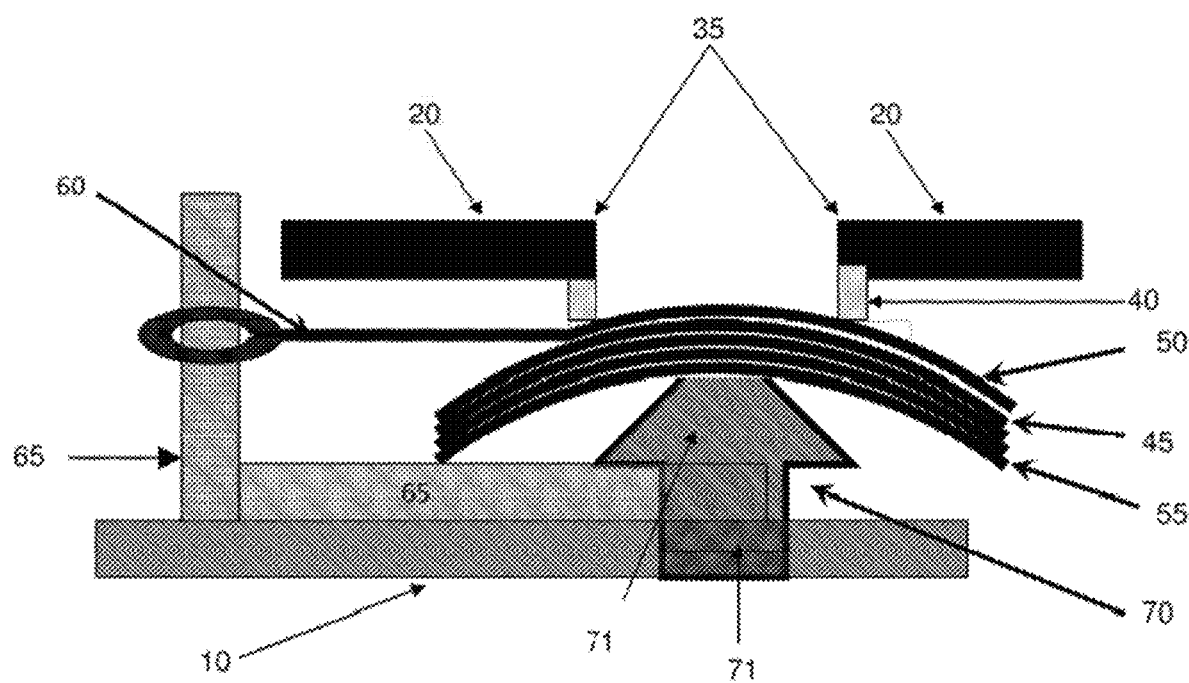
FIG. 14 depicts a lateral view of some components of a representative device according to some embodiments of the present invention.

FIG. 14 depicts a partial view of a device that can be used to detect multiple analytes with a single signal comprising a first housing member (10), a second housing member (20), an inlet opening (35), a test membrane (45), a conjugate pad (50), a plurality of absorbent members (55), an attachment member (60), a locking member (65), and a force member (70). FIG. 8 depicts the attachment member (60) attached to the conjugate pad (50) and the locking member (65). FIG. 14 also depicts the conjugate pad being compressed against the second housing member (20) and the perimeter of the inlet opening (35). FIG. 14 depicts the head of the force member (71) applying the pressure by contacting the plurality of absorbent members (55). In FIG. 14, a sample can be applied to the device through the inlet opening (35) so that the sample contacts the conjugate pad (50) and because of the pressure the sample through vertical flow contacts the test membrane (45).

Figure 15A:
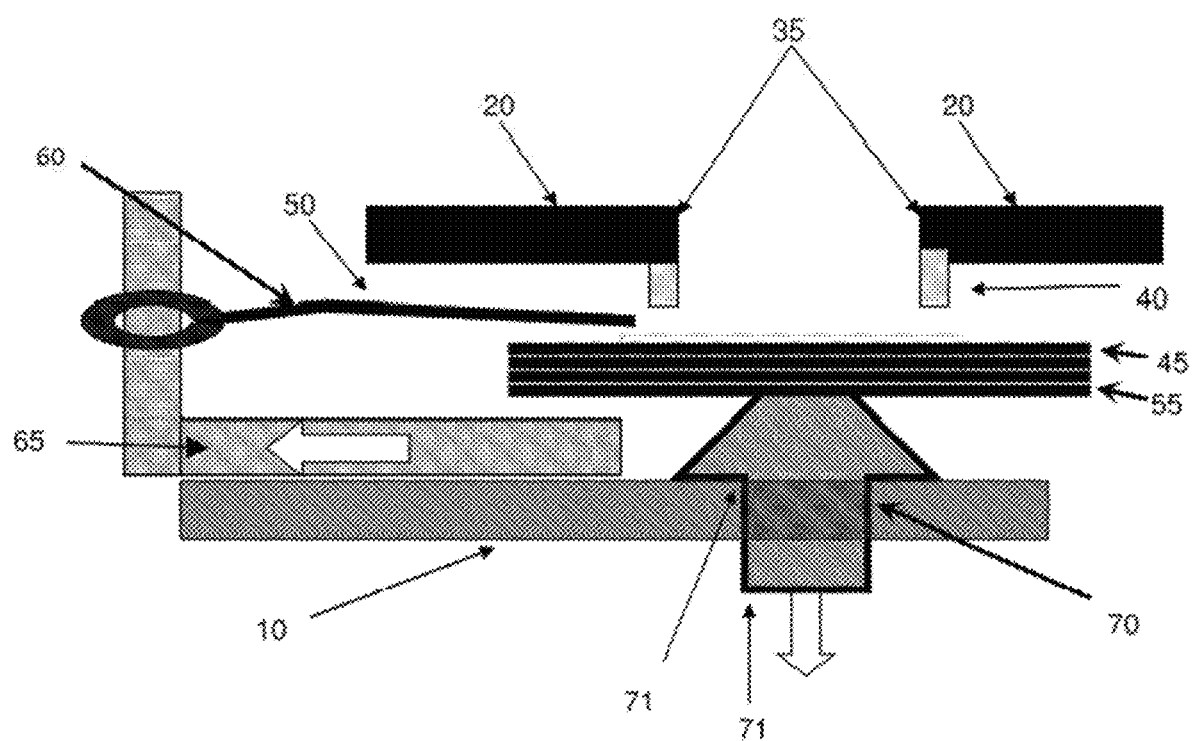
FIG. 15A depicts a lateral view of some components of a representative device according to some embodiments of the present invention.
Figure 15B:
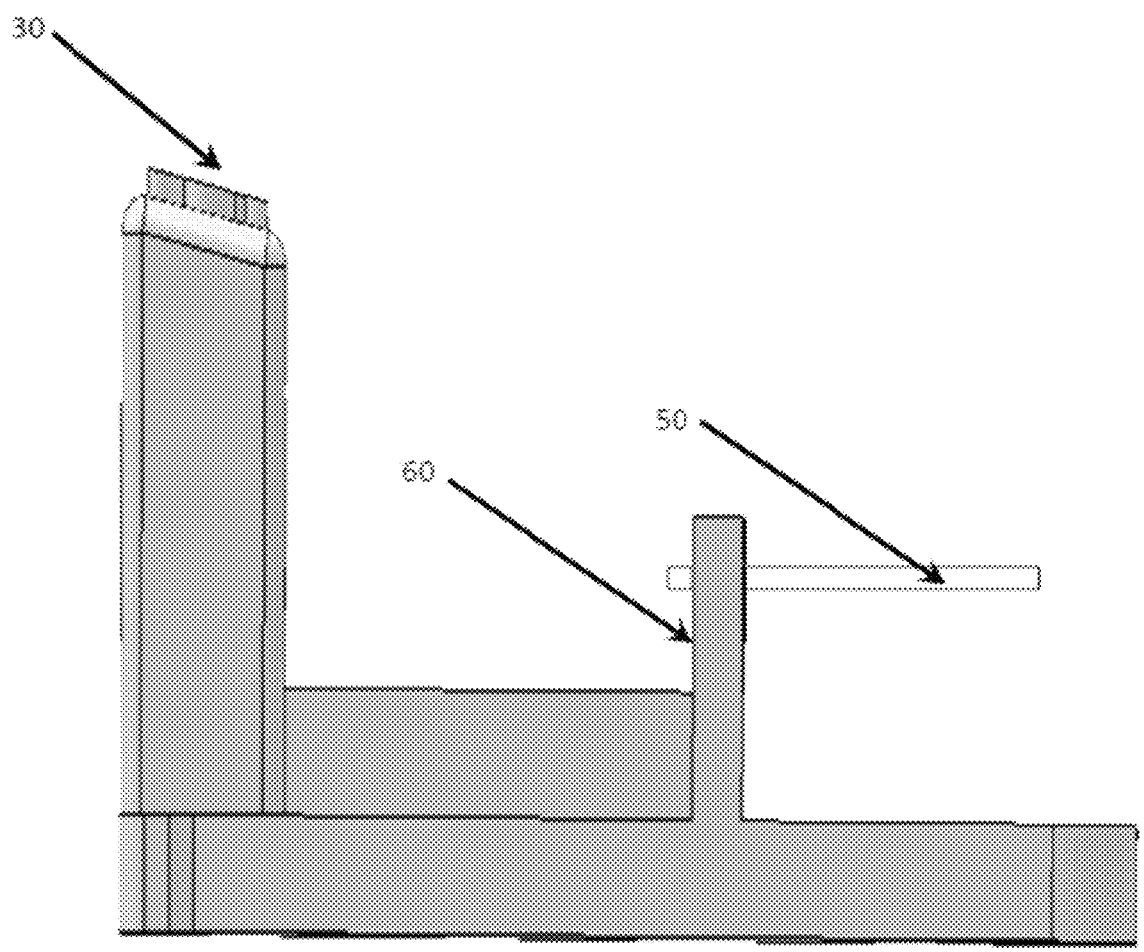
FIG. 15B depicts a view of some components, such as but not limited to, a non-flexible attachment member, of a representative device according to some embodiments of the present invention.
Figure 15C:
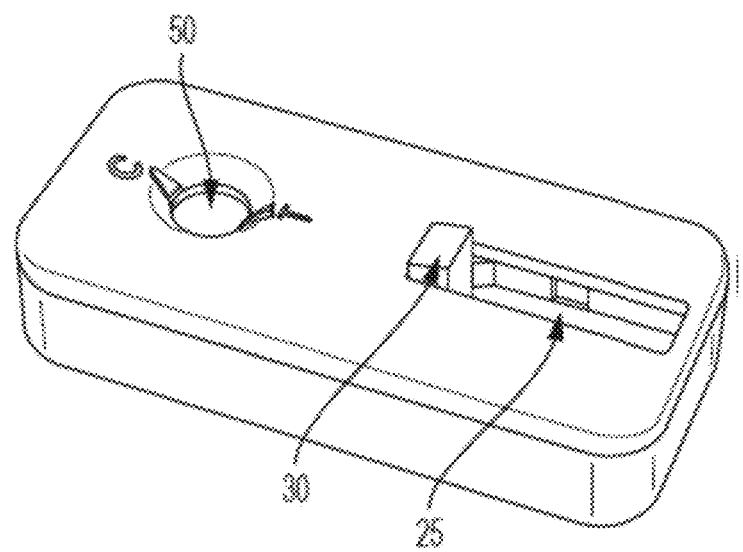
FIG. 15C depicts a perspective view of a representative device according to some embodiments of the present invention.
Figure 15D:
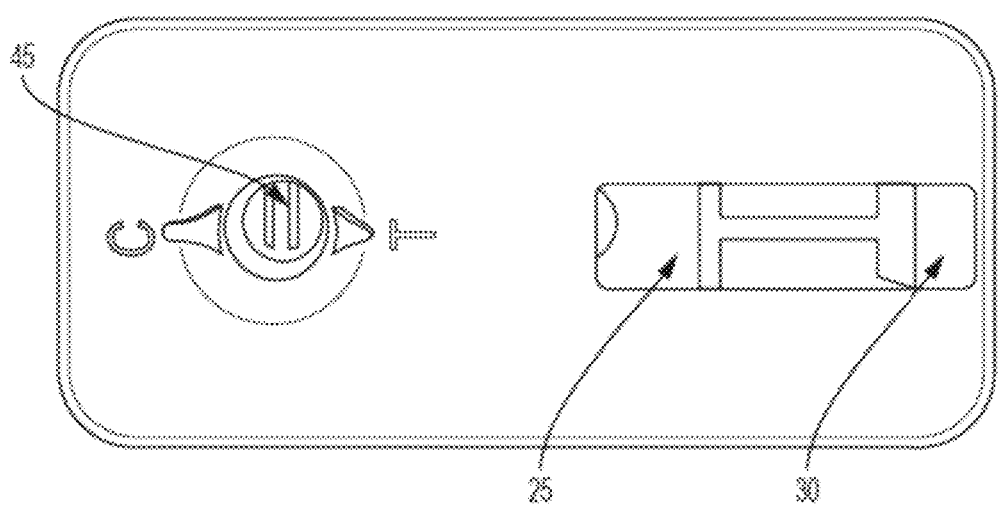
FIG. 15D depicts a perspective view of a representative device according to some embodiments of the present invention.

FIG. 15A depicts a partial view of a device that can be used to detect multiple analytes with a single signal comprising a first housing member (10), a second housing member (20), an inlet opening (35), a test membrane (45), a conjugate pad (50), a plurality of absorbent members (55), an attachment member (60), a locking member (65), and a force member (70). FIG. 8 depicts the movement of the locking member (65), which is attached to the attachment member (60). The movement of the attachment member (60), which is attached to the conjugate pad (50) moves the conjugate pad. FIG. 15A depicts the test force member (70) changing positions and a lessening or elimination of the pressure and/or compression of the test membrane (45). FIGS. 15C and 15D also depicts the movement of the conjugate pad (50) away from the inlet opening (35) revealing the test membrane (45) for visualization and/or detection.

Figure 16:
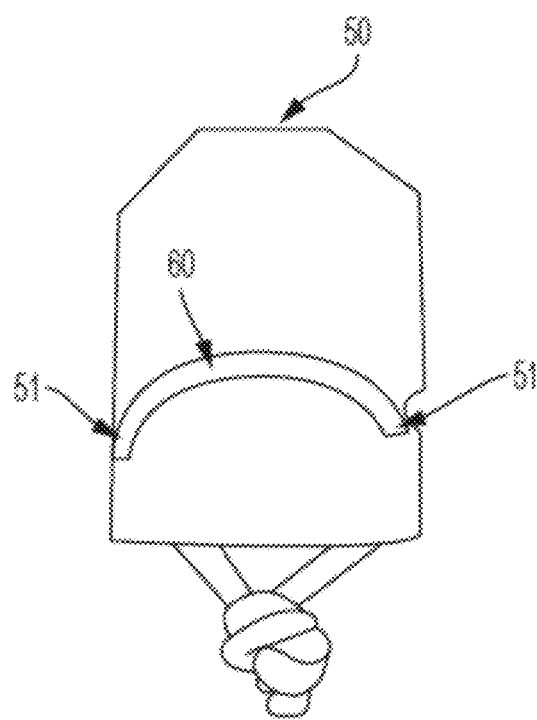
FIG. 16 depicts a flexible attachment member attached to a conjugate pad.

FIG. 16 depicts an attachment member (60) attached to a conjugate pad (50). FIG. 16 depicts notches (51) in the conjugate pad (50) as locations for the attachment member (60) to attach to. The attachment member can also be attached through other means such as through adhesives, staples, and other forms of attachment.

Figure 17:
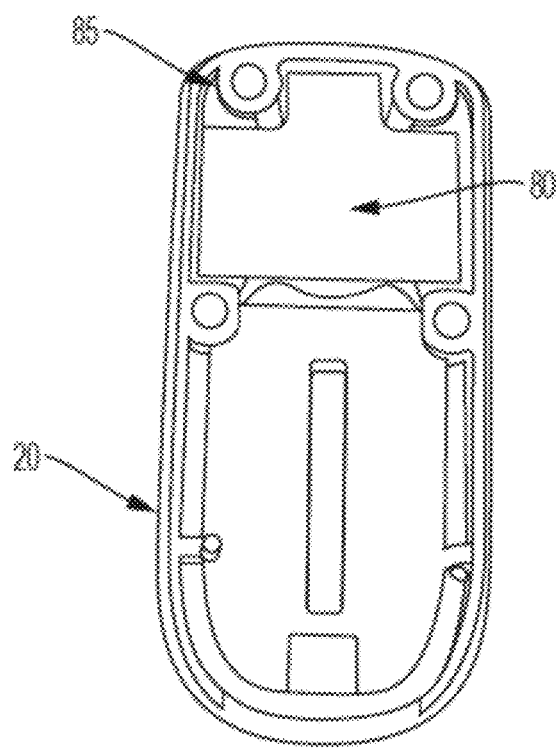
FIG. 17 depicts membranes in a representative housing member.

FIG. 17 depicts a partial view of device that can be used to detect multiple analytes with a single signal comprising a second housing member (20), a plurality of pads or membranes (80), wherein the plurality of pads comprises a test membrane, a permeable membrane, and one or more absorbent members, and retaining members (85) that can retain the plurality of pads or membranes (80). FIG. 10 depicts the structures that when the conjugate pad is moved the plurality of pads remains in place. Any means or other structure can be used to keep the plurality of pads in place.

FIG. 18 depicts a representative device that can be used to detect multiple analytes with a single signal comprising a first housing member (1002) that further comprises a housing inlet (1006), and a second housing member (1004). In some embodiments, the first and second housing members can be constructed as a single unit. The housing inlet allows for the introduction of a sample onto the components inside the housing. The housing inlet can be of sufficient size to handle an appropriate amount of volume of a solution that is added to the device. In some embodiments, the size of the opening created by the housing inlet is sufficient to handle about 0.1 to about 3 ml, about 0.1 to about 2.5 ml, about 0.5 to about 2.0 ml, about 0.1 to about 1.0 ml, about 0.5 to about 1.5 ml, about 0.5 to about 1.0 ml, and about 1.0 to about 2.0 ml. In some embodiments, the dimensions of the device are such that any dimension (e.g., width, depth, or height) is less than or equal to about 5.08 cm (2.000 inches). In some embodiments, the height of the device is less than about 0.635 cm (0.250 inches), less than about 0.254 cm (0.100 inches), less than about 0.191 cm (0.075 inches), less than about 0.165 cm (0.065 inches), less than about 0.152 cm (0.06 inches), or less than about 0.140 cm (0.055 inches). In some embodiments, the height of the device is about 0.127 cm (0.050 inches). In some embodiments, the width or depth of the device is less than or equal to about 5.08 cm (2.000 inches), about 4.83 cm (1.900 inches), about 4.699 cm (1.850 inches), about 4.572 cm (1.800 inches), about 4.445 cm (1.750 inches), about 4.191 cm (1.650 inches), about 4.064 cm (1.600 inches), or about 3.81 cm (1.500 inches). In some embodiments, the device is about 0.127 cm (0.050 inches) in height, about 4.445 cm (1.750 inches) in depth, and about 3.81 cm (1.500 inches) in width.

In some embodiments, the device that can be used to detect multiple analytes with a single signal comprises a plurality of components comprising one or more of: a removable member, a conjugate pad, an adhesive member, a test membrane, an absorbent member, a force member, a support member, or any combination thereof.

In some embodiments, the device that can be used to detect multiple analytes with a single signal comprises a force member, a removable member, a conjugate pad, a test membrane, an adhesive member and/or an absorbent member. In some embodiments, the device comprises an analyte detection membrane system. In some embodiments, the analyte detection membrane system comprises a conjugate pad, a test membrane, and an absorbent member. In some embodiments, the analyte detection membrane system comprises an additional permeable membrane, but the device can also be free of a permeable membrane. In some embodiments, the analyte detection membrane system comprises in the following order: a conjugate pad, an adhesive member, a test membrane, and an absorbent member.

FIG. 19 depicts an exploded view of the inside of a representative device that can be used to detect multiple analytes with a single signal comprising a removable member (1005), a conjugate pad (1050), an adhesive member (1010), a test membrane (1030), an absorbent member (1040), and a support member (1020), wherein the support member further comprises an optional support member inlet (1025). The removable member and the adhesive member can also comprise optional removable member inlet (1008) and adhesive member inlet (1012), respectively. Such components could reside within, for example, the device of FIG. 18.

Figure 20:
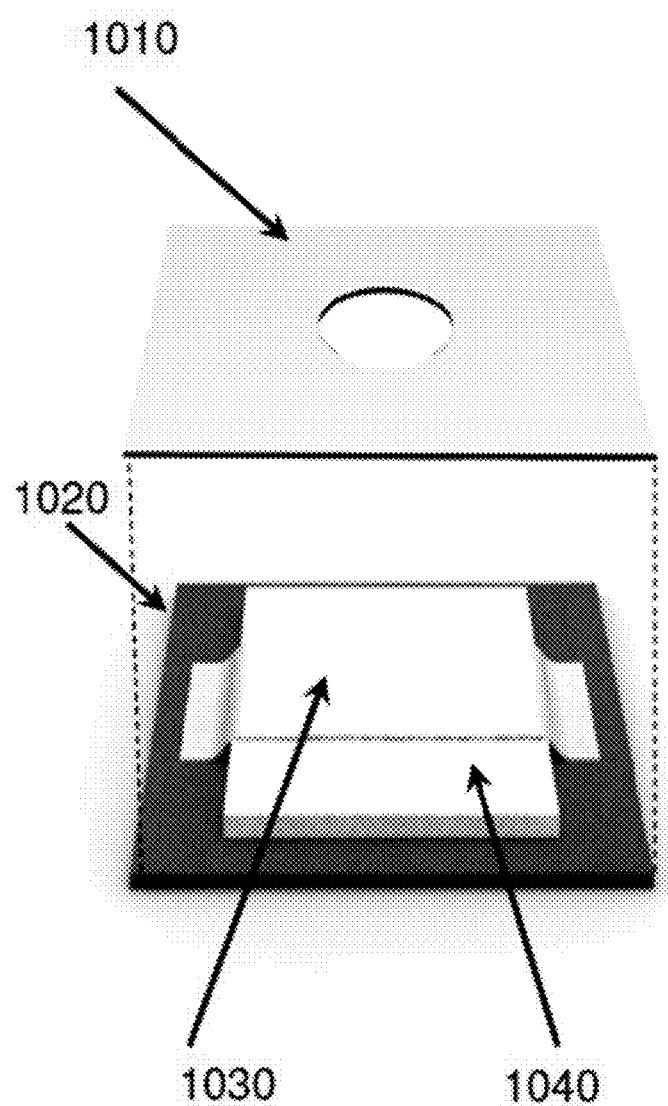
FIG. 20 depicts one type of analyte detection membrane system for a representative device according to some embodiments of the present invention.

FIG. 20 depicts representative components of another representative device that can be used to detect multiple analytes with a single signal comprising an adhesive member (1010), a support member (1020), a test membrane (1030), and an absorbent member (1040). As can be seen in FIG. 20, a sample can flow through the adhesive member (1010) and contact the test membrane (1030).

Figure 21:
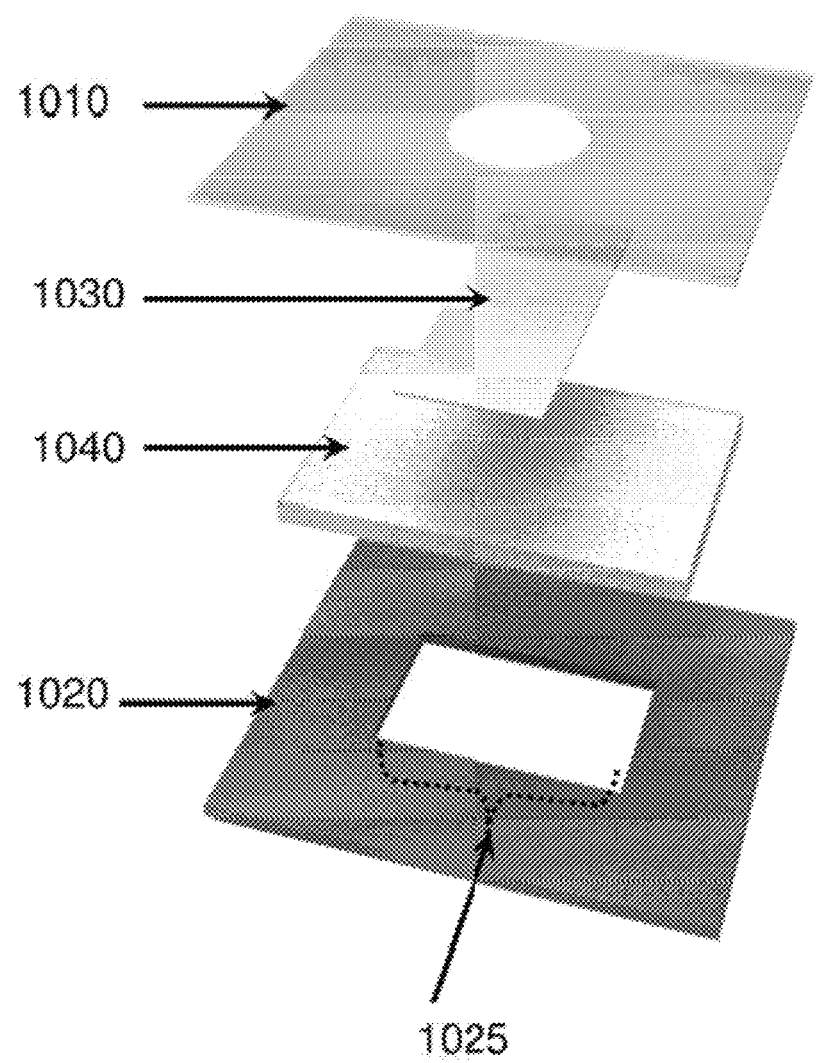
FIG. 21 depicts one type of analyte detection membrane system for a representative device according to some embodiments of the present invention.

FIG. 21 depicts an adhesive member (1010), a support member (1020), a test membrane (1030), and an absorbent member (1040). FIG. 21 depicts the components being substantially parallel with one another. FIG. 21 further depicts the support member (1020) comprising a support member inlet (1025). This inlet can be used to allow the sample to vertically flow through the device.

Figure 22:
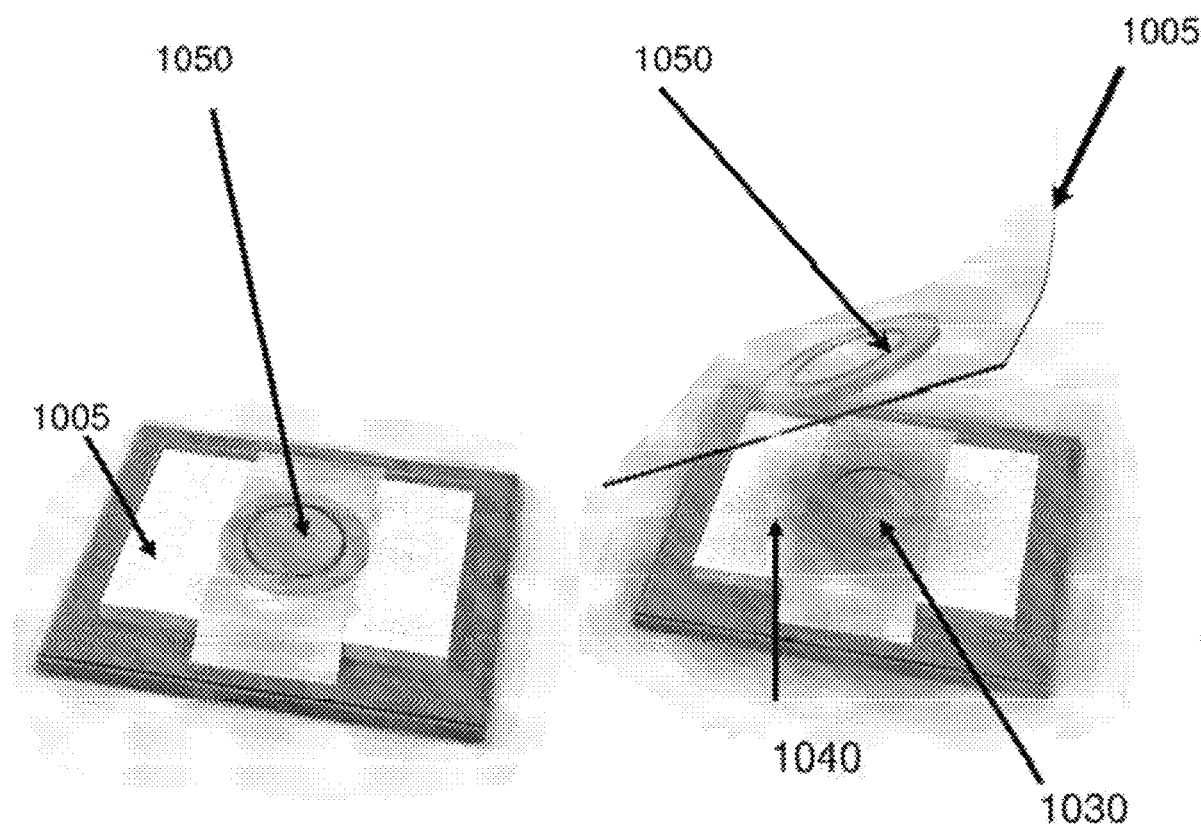
FIG. 22 depicts one type of analyte detection membrane system for a representative device according to some embodiments of the present invention.

FIG. 22 depicts, in part, a conjugate pad (1050), a test membrane (1030), and an absorbent member (1040). FIG. 22 also depicts the conjugate pad in contact and/or attached to a removable member (1005). FIG. 22 also depicts the removable member being removed or moved away from the device that can be used to detect multiple analytes with a single signal, which also removes or moves away from the device the conjugate pad. The movement of the conjugate pad allows the test membrane to be visualized, which facilitates analysis and detection of analytes, including multiple analytes with a single signal.

FIG. 23 depicts examples of force members (e.g. clips). Representative force members can come in a variety of shapes, sizes, and configurations, but each member applies pressure on the components that are placed in or on the force member. Each force member can also comprise an opening (+) into which the analyze sample is applied. FIG. 23 depicts non-limiting examples of force members with a first member (110) and a second member (100).

Figure 24A:
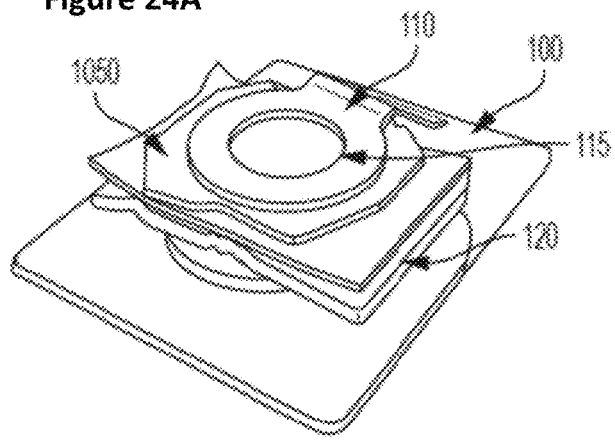
FIGS. 24A-24D depict a representative device according to some embodiments of the present invention.
Figure 24B:
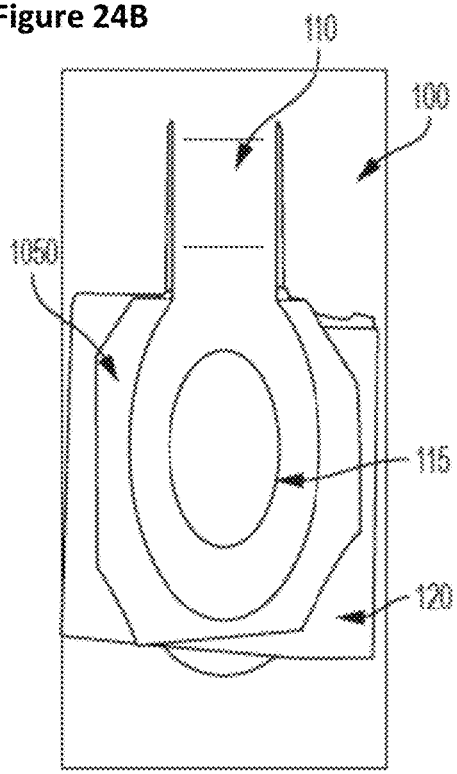
Figure 24C:
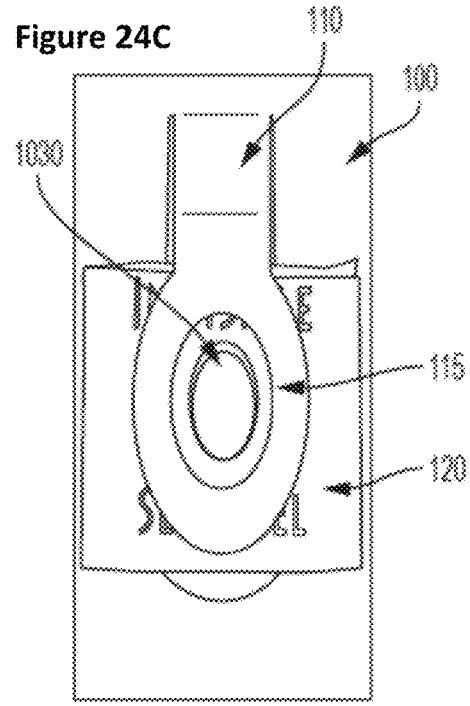
Figure 24D:
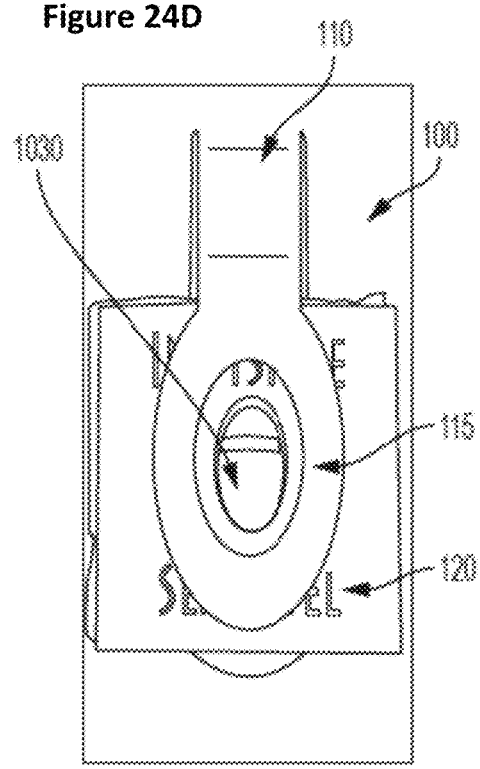

FIGS. 24A, 24B, 24C, and 24D depict, in part, a force member comprising a first member (110), b) a second member (100), an inlet (115), and an analyte detection membrane system (120). FIGS. 24A and 24B also depict, in part, a conjugate pad (1050). The conjugate pad is not seen in FIGS. 24C and 24D. FIGS. 24C and 24D also depict, in part, a test membrane (1030) that is part of the analyte detection membrane system. FIG. 24D also depicts in part, a test membrane (1030) that has been reacted with a control, which is visualized by the band.

Figure 25A:
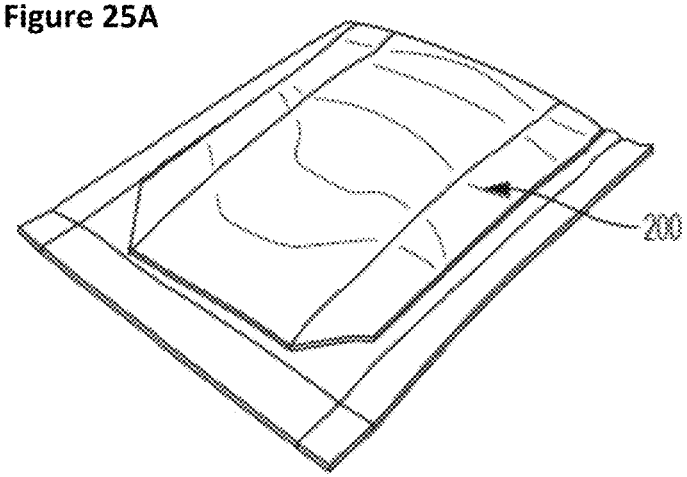
FIGS. 25A-25C depict a representative device according to some embodiments of the present invention.
Figure 25B:
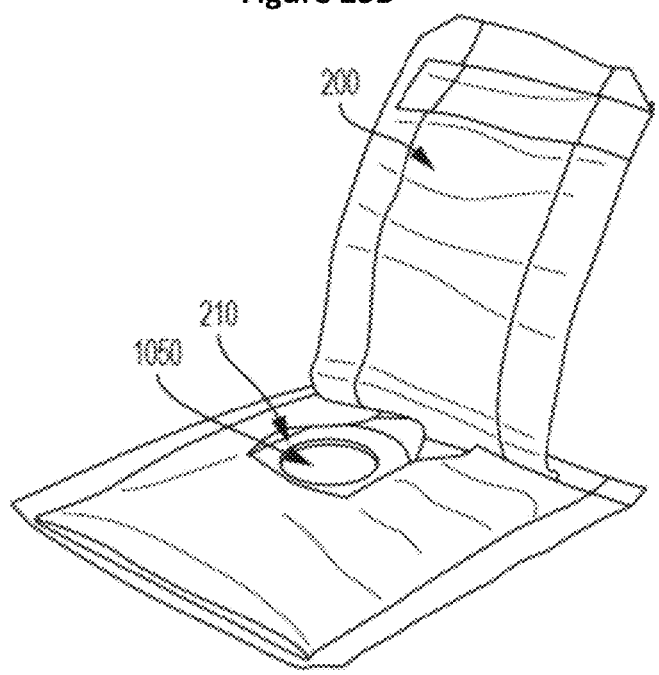
Figure 25C:
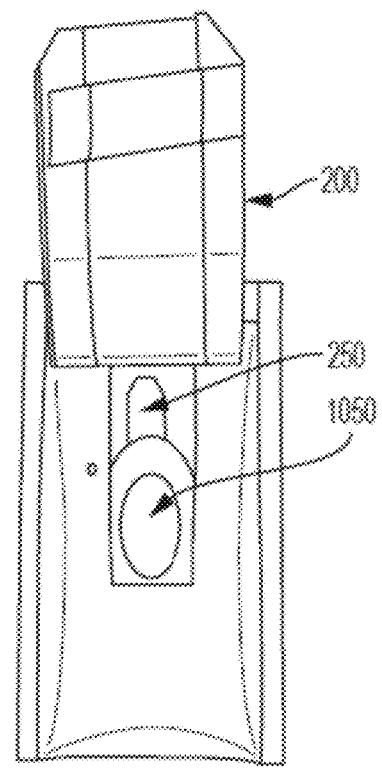

FIG. 25 depicts, in part, a container comprising a removable or movable tab (200), an inlet (210), a conjugate pad (1050), and the tab of the conjugate pad (1050). The tab of the conjugate pad (255) can be used to remove the conjugate pad (1050) from the device to expose the test membrane. For example, a user could pull the tab of the conjugate pad (255) to remove the conjugate pad (1050) from the container. What is not visualized is the analyte detection membrane system that is compressed between a first member (110) and a second member (100) as described herein.

Figure 26:
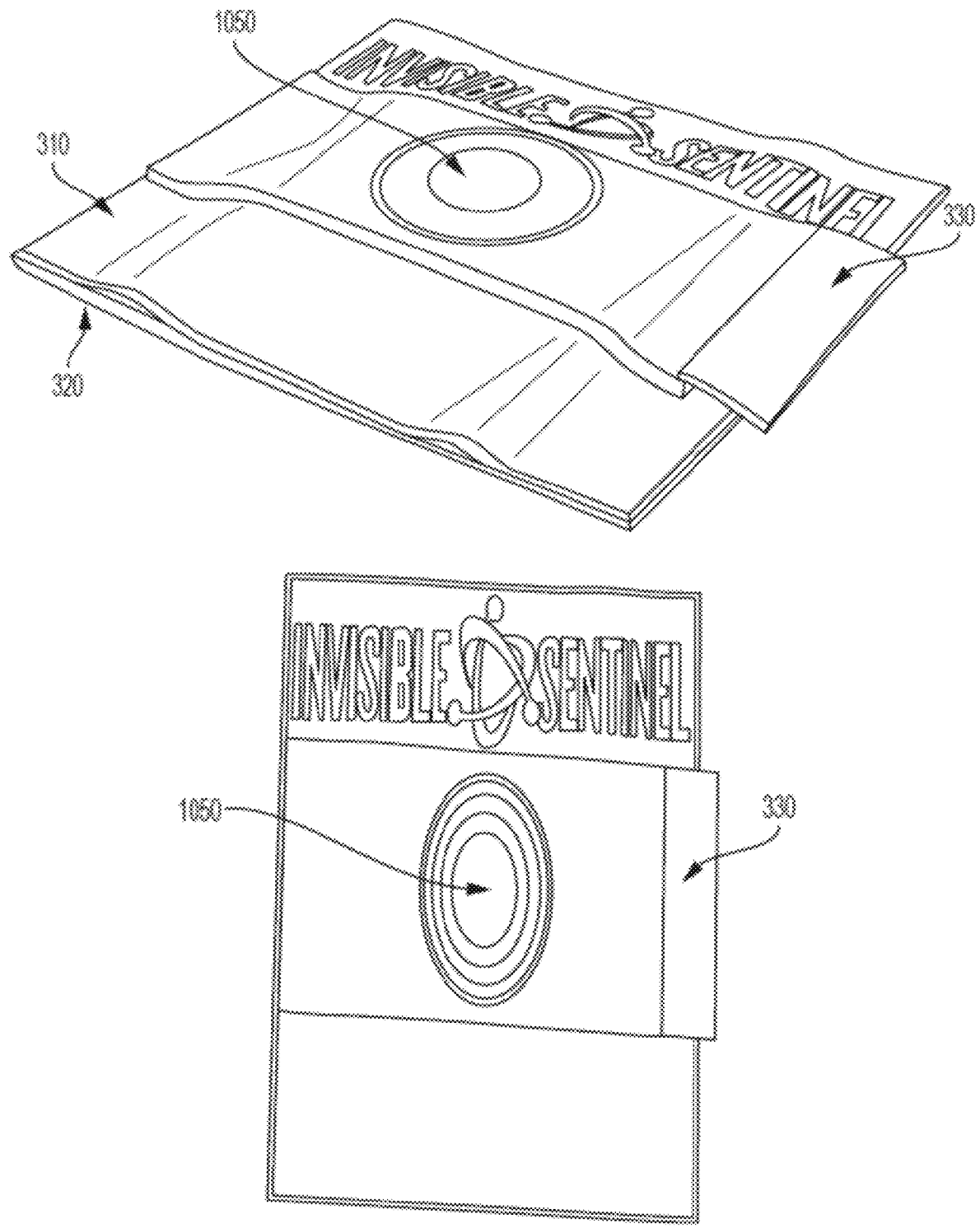
FIG. 26 depicts representative devices according to some embodiments of the present invention.

FIG. 26 depicts, in part, a first outer member (310), a second outer member (320), a movable or removable tab (330), and a conjugate pad (1050). The movable or removable tab (330) comprises an inlet that exposes the conjugate pad (1050) so that the sample can be applied to the conjugate pad. FIG. 26 does not show the first inner member (110) and the second inner member (100) compressing the analyte detection membrane system (120). The removable or movable tab (330) when moved or removed, moves or removes the conjugate pad (1050), which allows the test membrane to visualized and analyzed.

The removable member inlet within the removable member allows the introduction of a sample onto the conjugate pad. The inlet can be of sufficient size to handle an appropriate amount of volume of a solution that is added to the device. In some embodiments, the size of the inlet is large enough to handle about 0.1 to about 3 ml, about 0.1 to about 2.5 ml, about 0.5 to about 2.0 ml, about 0.1 to about 1.0 ml, about 0.5 to about 1.5 ml, about 0.5 to about 1.0 ml, and about 1.0 to about 2.0 ml. The removable member can also be constructed such that a portion of the removable member is permeable to solutions (i.e., the area defined by the removable member inlet) and another area is impermeable. The permeable area can act as an inlet because it would allow solutions to cross the removable member and contact the conjugate pad. The removable member inlet can have any one of numerous shapes and sizes. In some embodiments, the first housing member serves as the removable member. In other embodiments, the first housing member and the removable member are separate components. In embodiments where the first housing member and the removable member are separate components, at least a portion of the housing inlet and removable member inlet overlap such that a solution can enter through both inlets.

In some embodiments, the removable member contacts a first surface of a conjugate pad. The removable member can also be attached to the conjugate pad. The removable member can be attached to the conjugate pad by any means such that when the removable member is removed from the device or its position is changed, the conjugate pad is also removed or the position of the conjugate pad is also changed. The removable member can be attached to the conjugate pad with, for example, but not limited to, an adhesive. Adhesives include, but are not limited to, glue, tape, or other substance that would allow the removable member and the conjugate pad to be attached to one another.

The removable member, in some embodiments, directly contacts the conjugate pad or indirectly contacts the conjugate pad through another layer. The sample can be, in some embodiments, directly applied to the conjugate pad through the opening in the removable member.

Figure 27A:
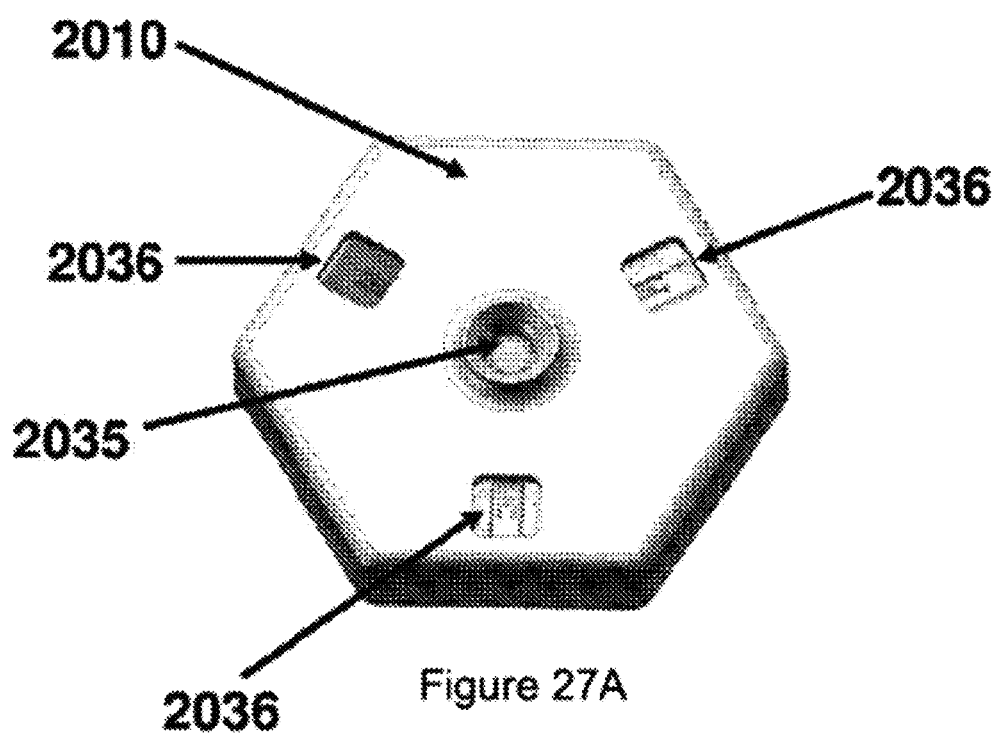
FIGS. 27A-27B depict a view of a representative device according to some embodiments of the present invention.
Figure 27B:
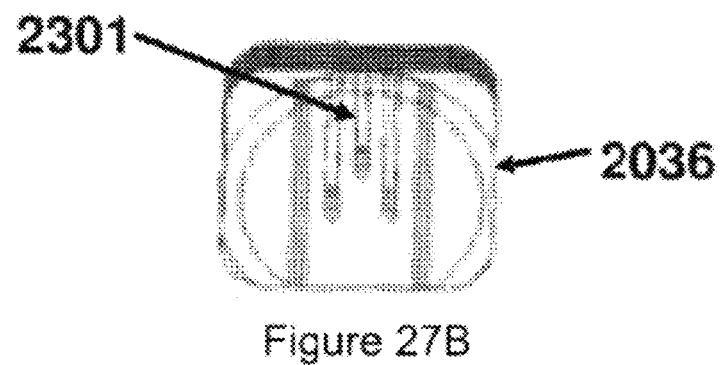

FIG. 27A depicts, in part, an overhead view of a device that can be used to detect multiple analytes with a single signal comprising a plurality of portals (2036), an inlet (2035), and a housing member (2010). FIG. 27A also depicts, in part, a portion of the channel system (2300) that is visible through the portal (2301). FIG. 27B depicts, in part, an enlarged area of the device, specifically, the portal (2036). In the portal one can also see a plurality of capillary tubes (2301).

Figure 28:
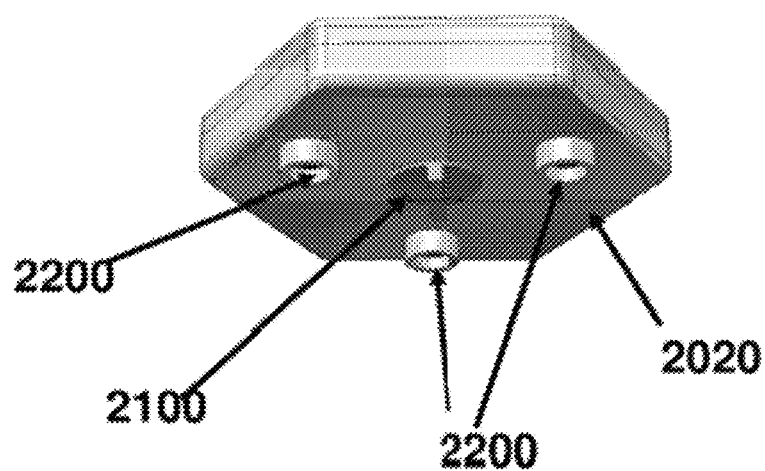
FIG. 28 depicts an underneath view of a representative device according to some embodiments of the present invention.

FIG. 28 depicts an underneath view of a device that can be used to detect multiple analytes with a single signal comprising a plurality of force actuator outlets (2200), a housing member (2020), and a moving member (2100).

Figure 29:
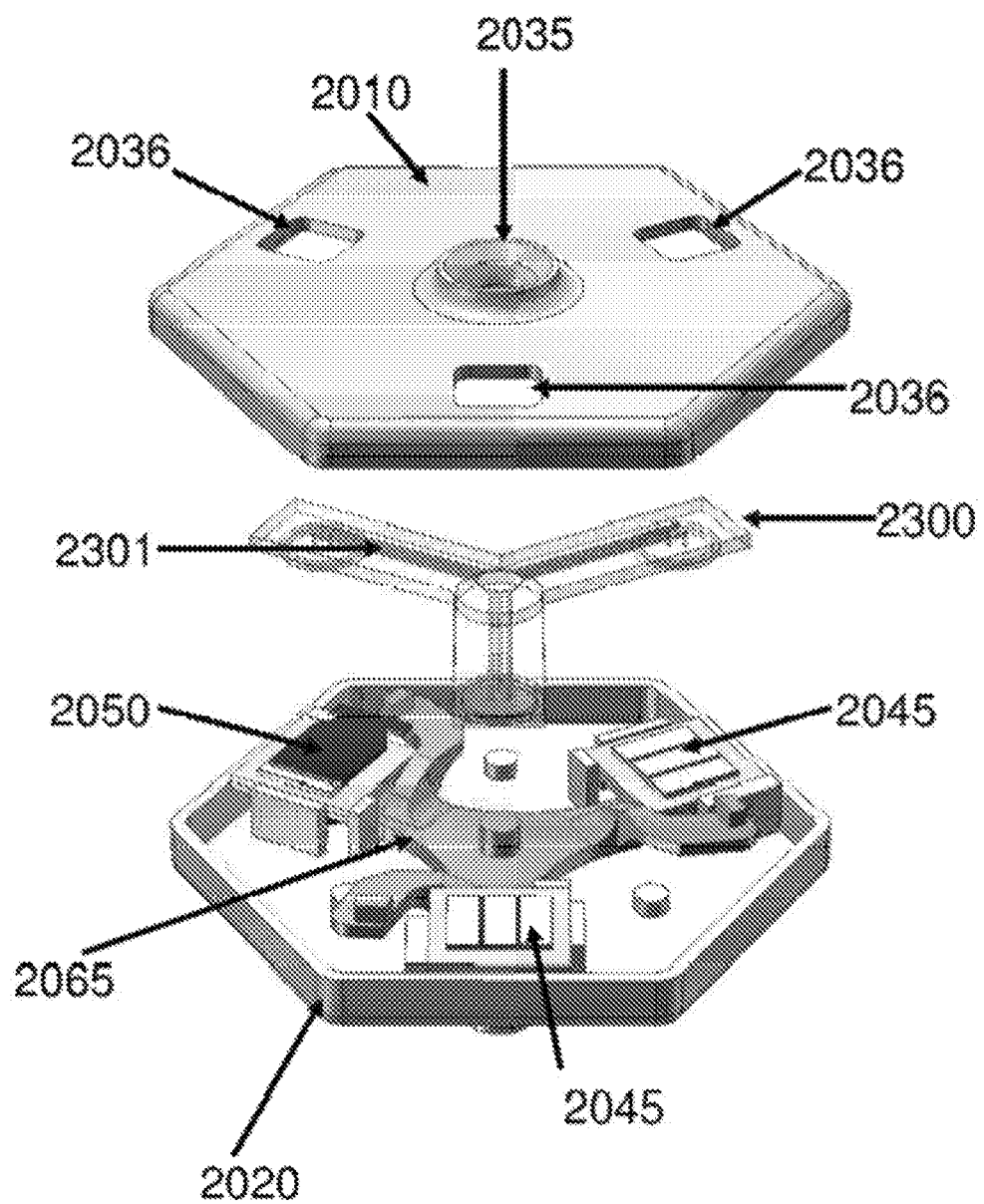
FIG. 29 depicts an exploded view of a representative device according to some embodiments of the present invention.

FIG. 29 depicts, in part, a first housing member (2010), a second housing member (2020) a plurality of portals (2036), an inlet (2035), a channel system (2300), a plurality of capillary tubes (2301), a conjugate pad (2050), a plurality of test membranes (2045), and movable locking member (2065). The channel system depicted in FIG. 29 is depicted as consisting 3 branches, which is equal to the number of analyte detection membrane systems present in the device.

Figure 30:
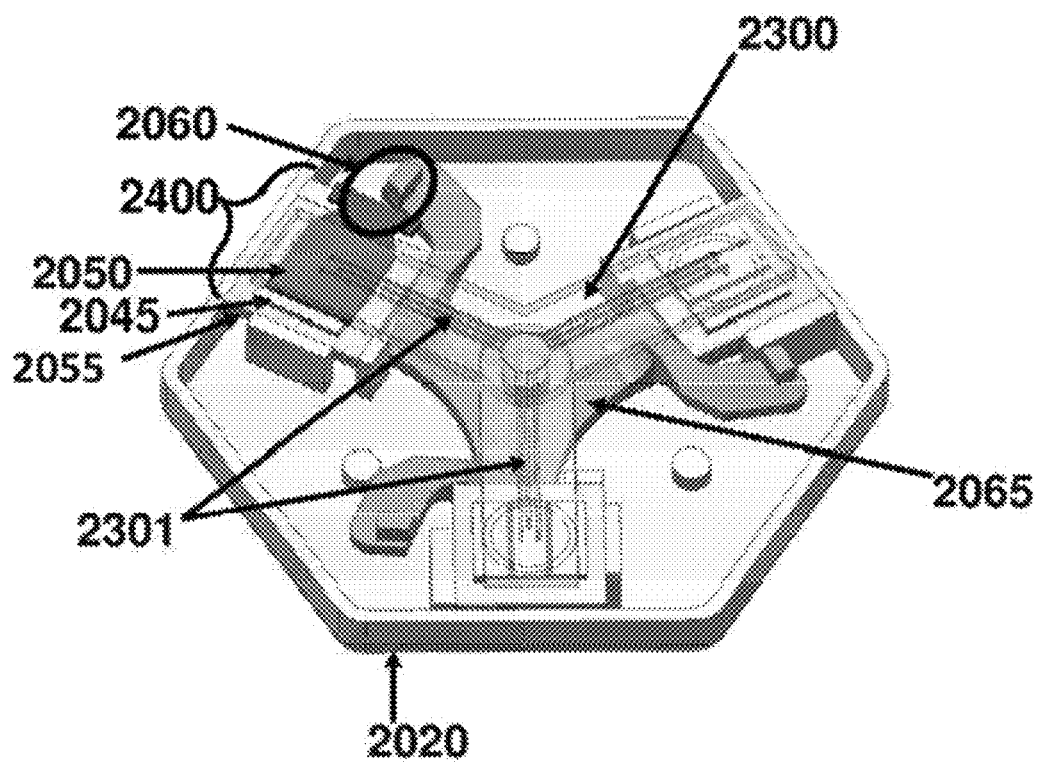
FIG. 30 depicts an interior view of a representative device according to some embodiments of the present invention.

FIG. 30 depicts, in part, a second housing member (2020), a channel system (2300), a plurality of capillary tubes (2301), a conjugate pad (2050), a test membrane (2045), and an absorbent membrane (2055), and a movable locking member (2065), a flexible attachment member (2060), an analyte detection membrane system (2400)

Figure 31A:
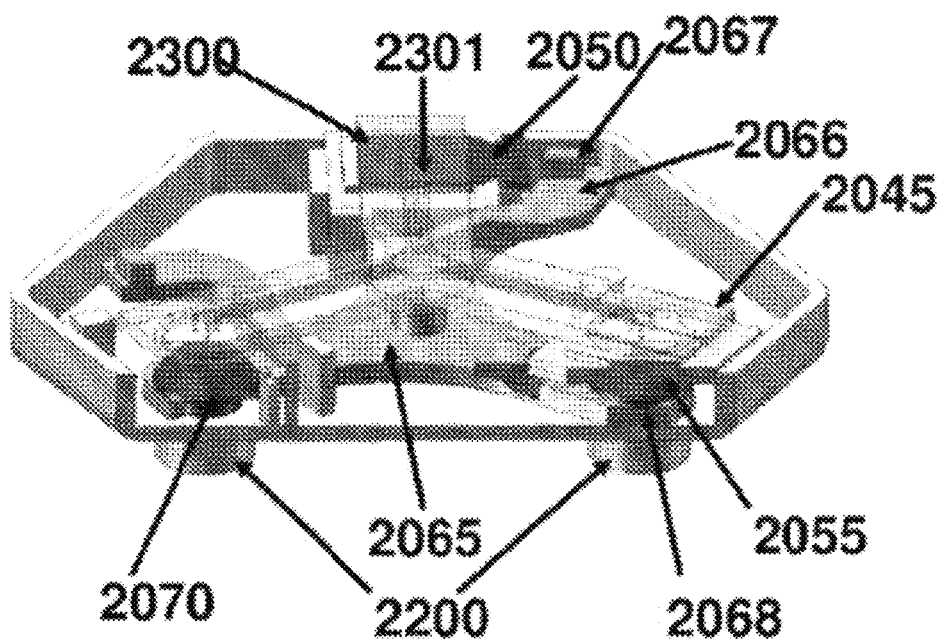
FIGS. 31A-31B depict a cross-sectional view of a representative device according to some embodiments of the present invention.

FIG. 31A depicts, in part, a plurality of force actuator outlets (2200), a channel system (2300), a plurality of capillary tubes (2301), a plurality of force members (2070), a movable locking member (2065), a plurality of movable locking member extensions (2068), a conjugate pad (2050), a plurality of flexible or non-flexible attachment member extensions (2066) and nodule (2067), a test membrane (2045), and absorbent membrane (2055).

Figure 31B:
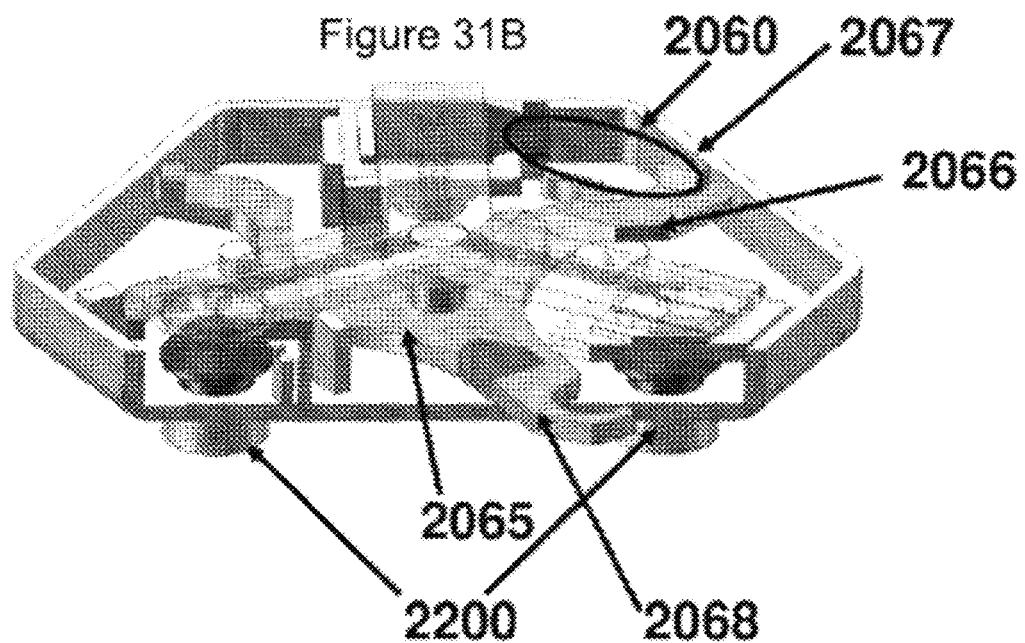

FIG. 31B depicts, in part, a similar portion of the device shown in FIG. 24A, however, the movable locking member (2065) has been rotated around a central axis and the movable locking member extension (2068) no longer supports the force member (2070) and the force member has receded or dropped into the force actuator outlet (2200).

Figure 32:
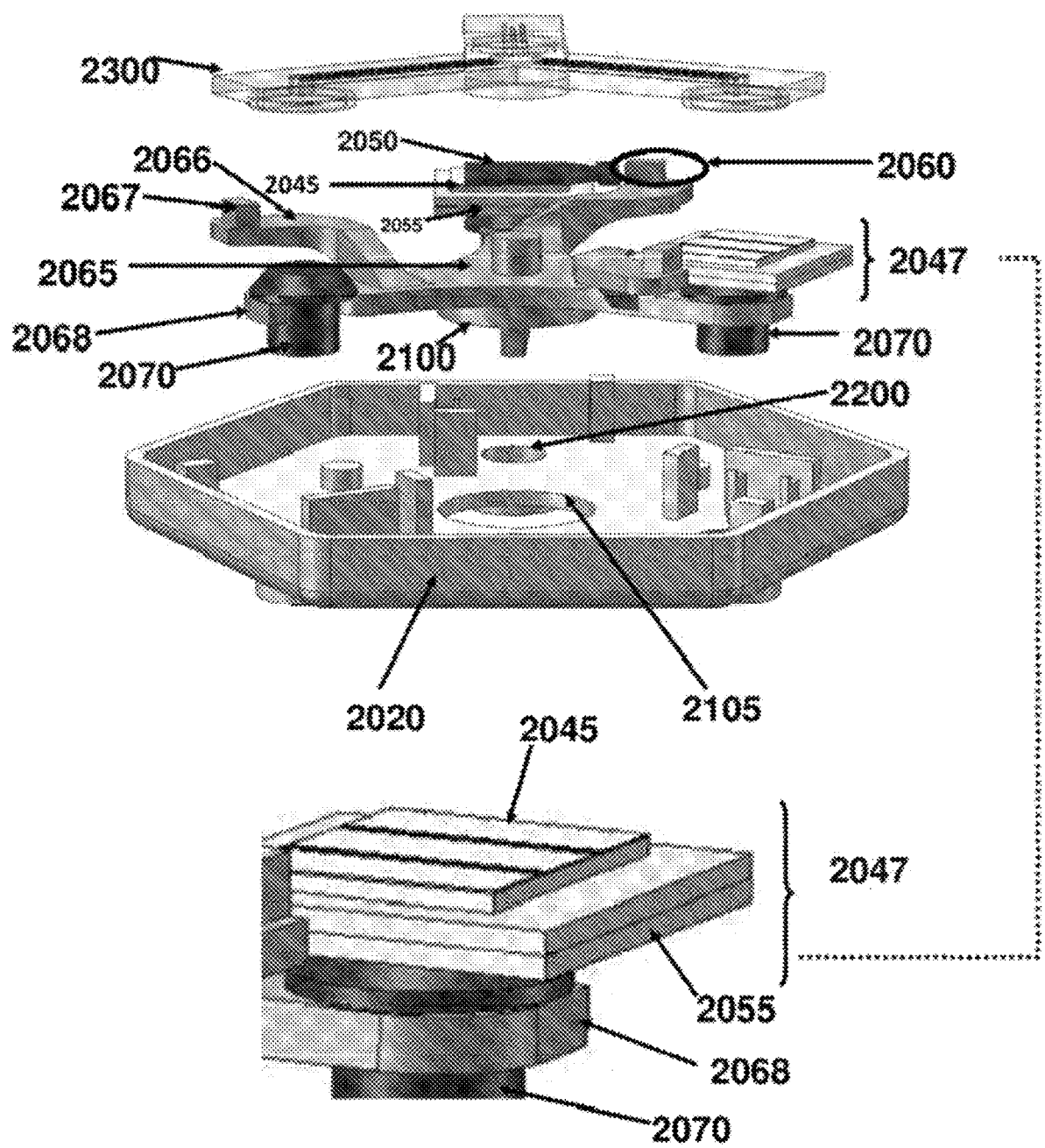
FIG. 32 depicts an exploded view of a representative device according to some embodiments of the present invention.

FIG. 32 depicts, in part, an exploded view of a device that can be used to detect multiple analytes with a single signal comprising a channel system (2300), a conjugate pad (2050), a test membrane (2045), a plurality of force members (2070), a movable member (2100) that can turn the movable locking member depicted (2065). FIG. 32 also depicts, in part, movable locking member extension (2068), a plurality of flexible or non-flexible attachment member extensions (2066) and nodule (2067), a flexible attachment member (2060), an outlet (2105), a second housing member (2020), a plurality of force actuator outlets (2200), and a portion of an analyte detection membrane system (2047). The area comprising the portion of the analyte detection membrane system (2047) has been enlarged and depicts, in part, a force member (2070), a test membrane (2045), an absorbent member (2055), and portion of the movable locking member extension (2068).

FIG. 33 depicts, in part, a housing (2020), a capillary channel (2301) and the channel system (2300). A portion of FIG. 33 has been enlarged to depict the conjugate pad (2050), the absorbent member (2055), and a plurality of capillary tubes (2301).

Figure 34:
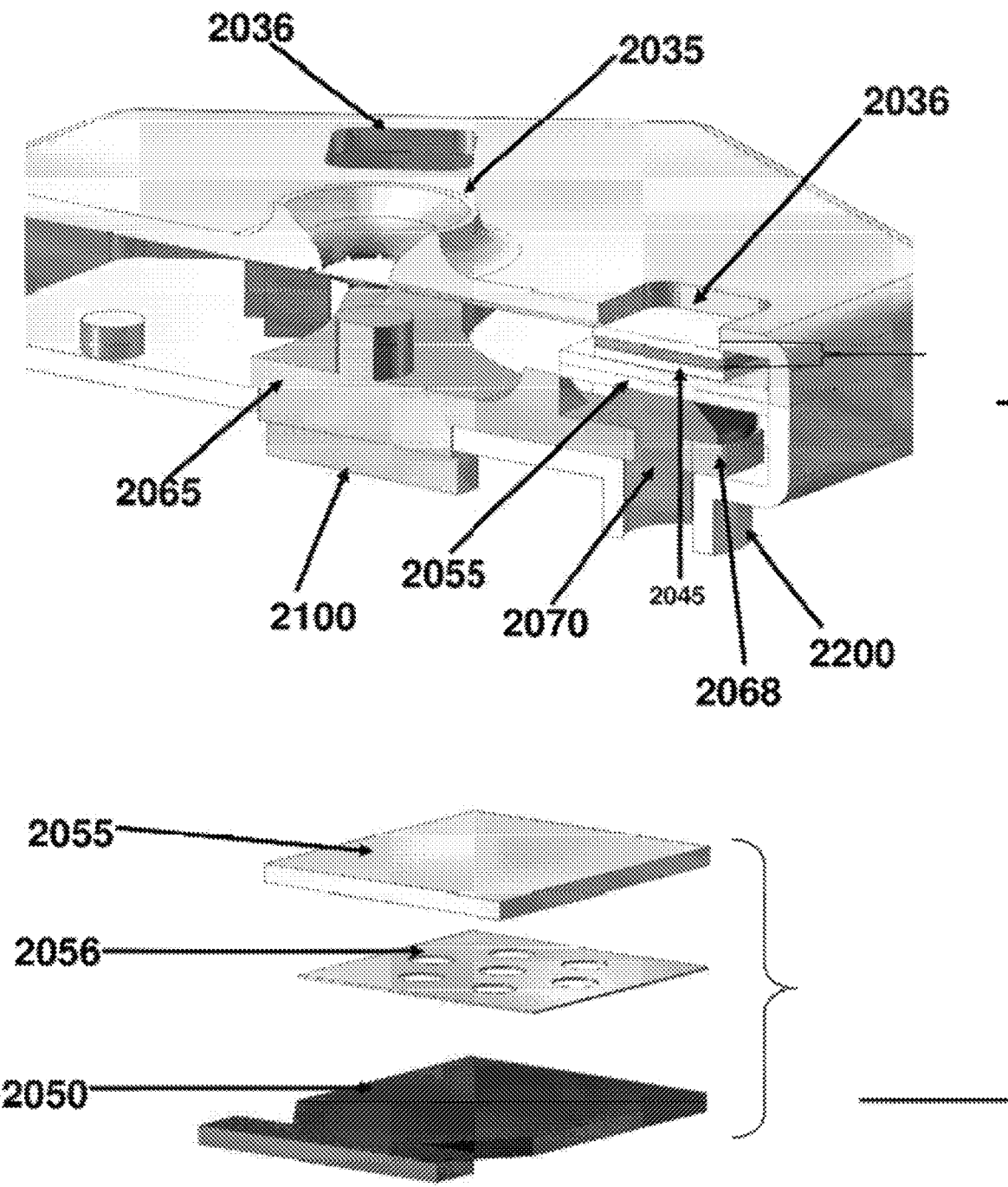
FIG. 34 depicts a cross-sectional view of a representative device according to some embodiments of the present invention.

FIG. 34 depicts, in part, a cross-sectional view of a device that can be used to detect multiple analytes with a single signal comprising a plurality of portals (2036), an inlet (2035), a movable locking member (2065), a movable member that can move the movable locking member (2100), a force member (2700), a force actuator outlet (2200), a plurality of absorbent members (2055), a test membrane (2045), and a movable locking member extension (2068). FIG. 34 also depicts an exploded view of a portion of the analyte detection membrane system comprising a conjugate pad (2050), a permeable membrane (2056), and an absorbent member (2055).

Figure 35:
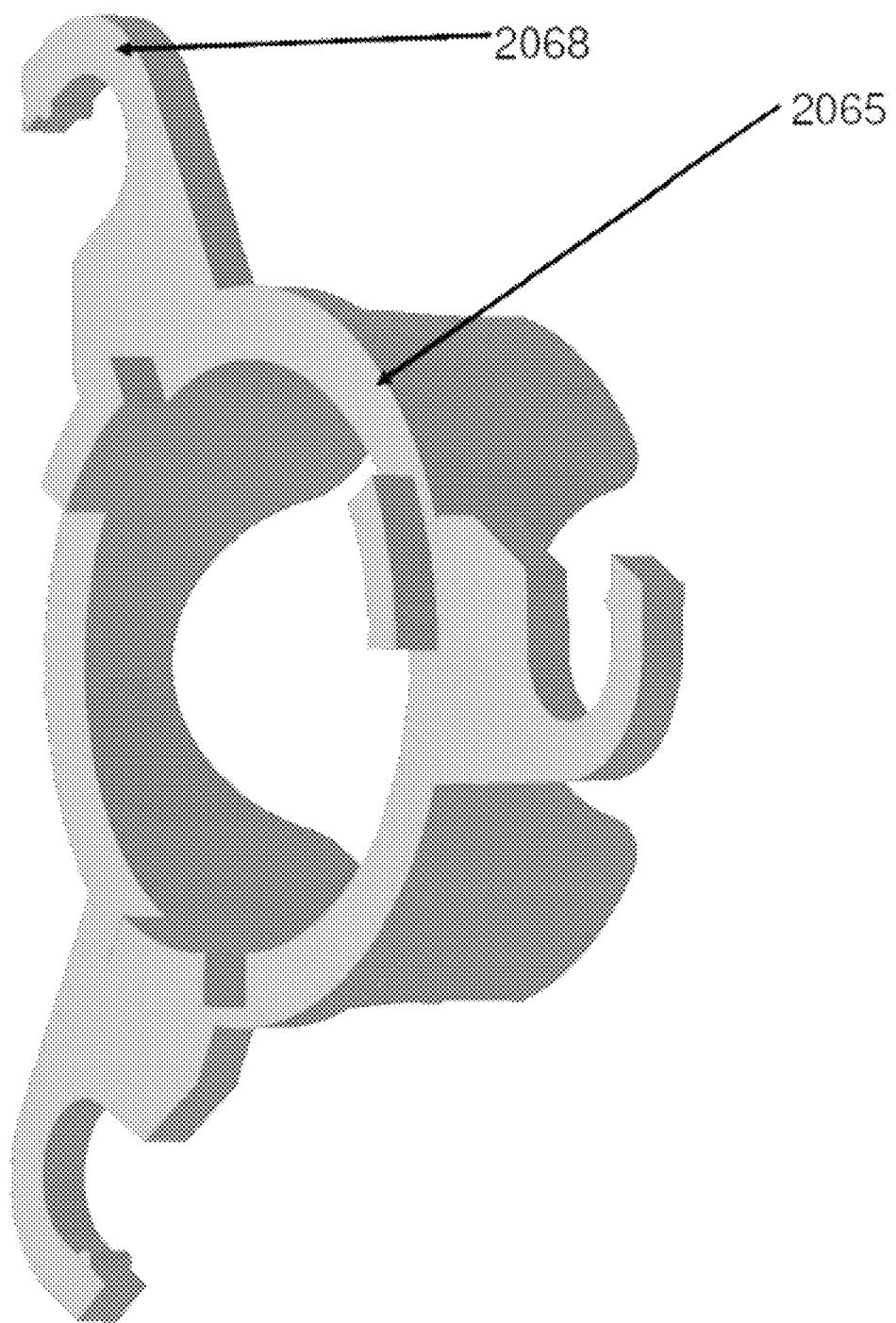
FIG. 35 depicts a representative movable locking member according to some embodiments of the present invention.

FIG. 35 depicts, in part, a non-limiting example of a movable locking member (2065) and a movable locking member extension (2068).

Figure 36:
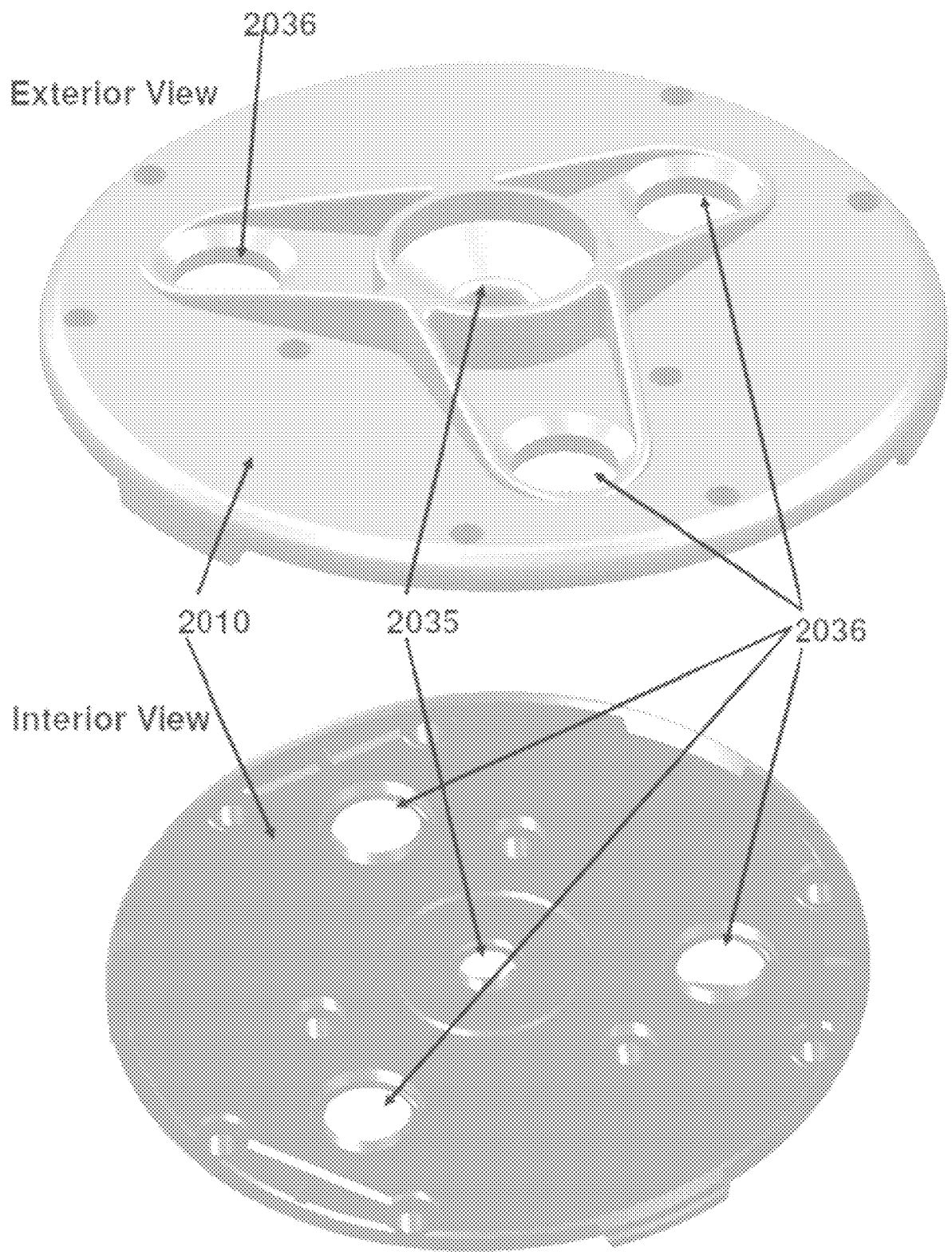
FIG. 36 depicts a representative housing according to some embodiments of the present invention.

FIG. 36 depicts, in part, an exterior view and an interior view of a housing comprising a plurality of portals (2036) and an inlet (2035).

Figure 37:
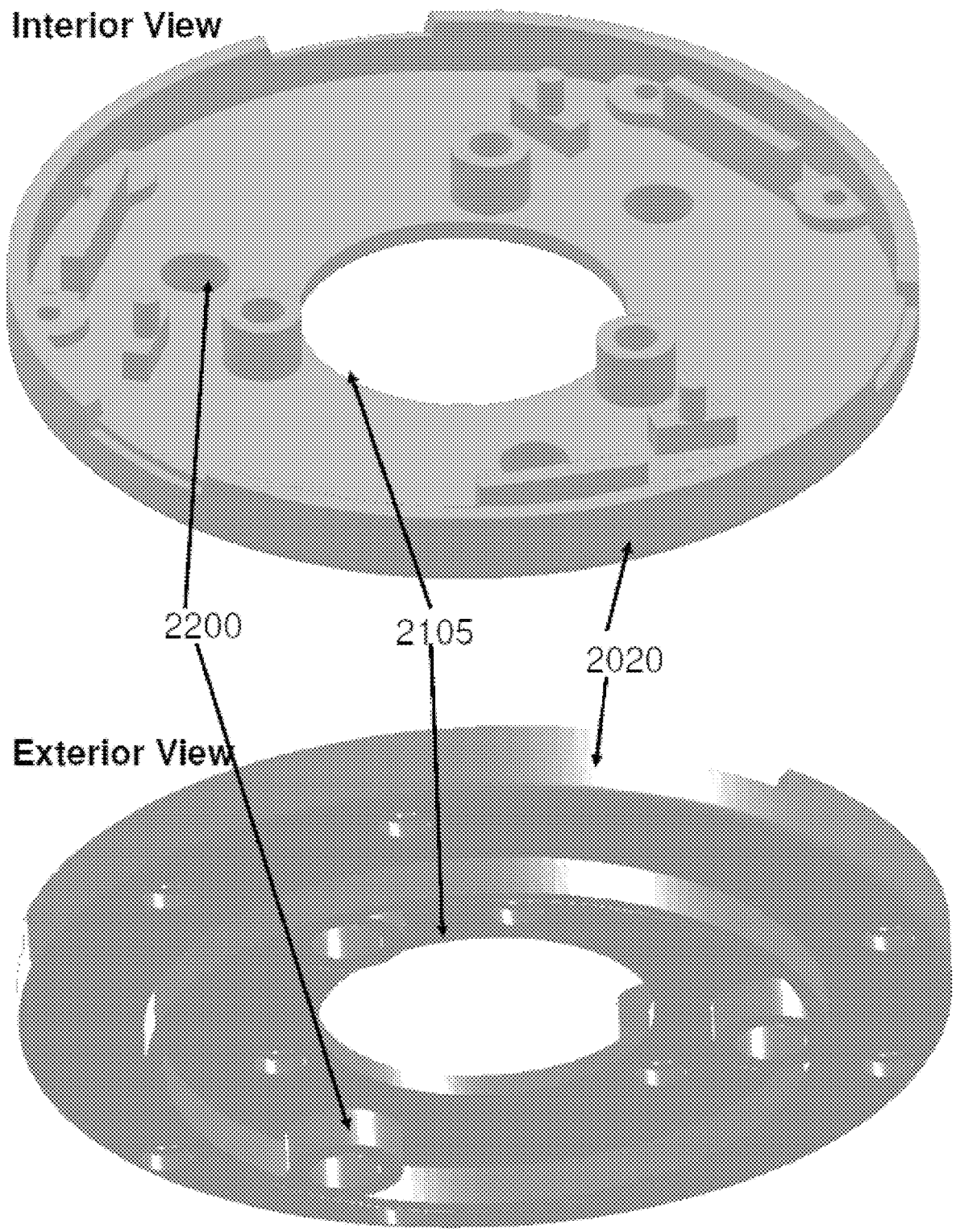
FIG. 37 depicts a representative housing according to some embodiments of the present invention.

FIG. 37 depicts, in part, an interior view and an exterior view of a housing comprising a plurality of force actuator outlets (2200) and a movable member outlet (2105).

Figure 38A:
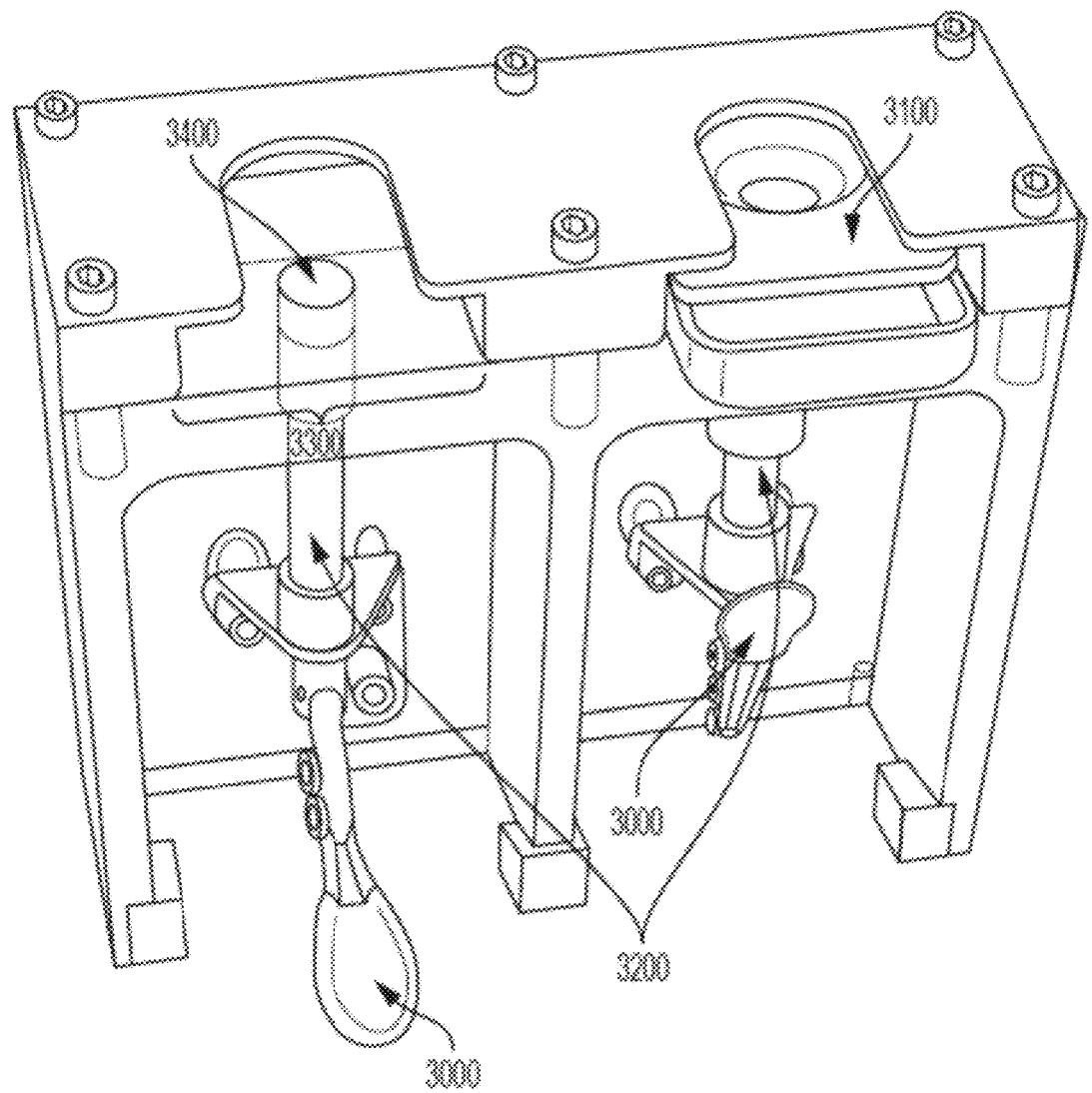
FIG. 38A depicts a representative device according to some embodiments of the present invention.
Figure 38B:
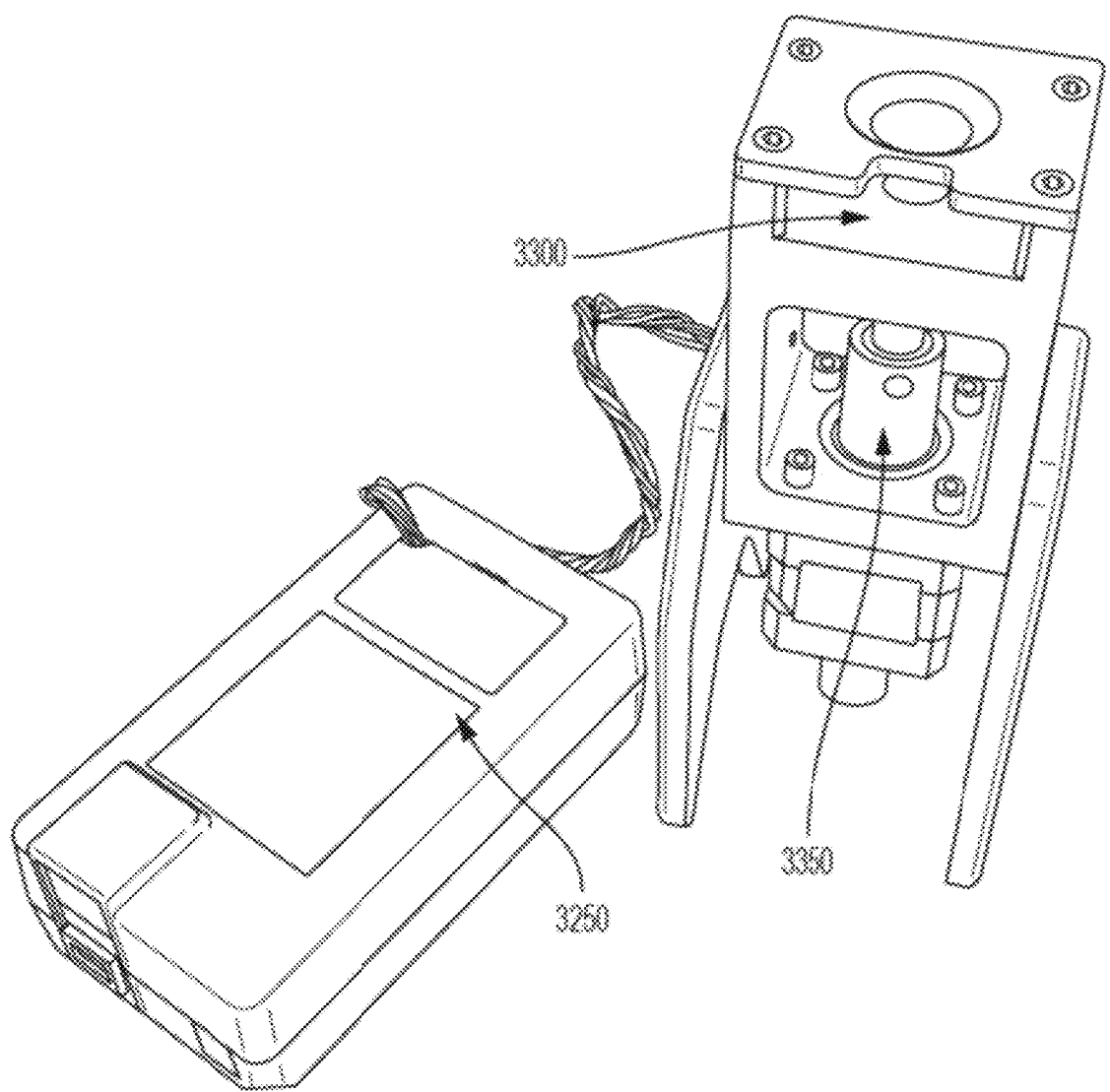
FIG. 38B depicts a representative device according to some embodiments of the present invention.

FIG. 38 depicts, in part, a device comprising a cartridge (3100) that can encompass an analyte detection membrane system, a force actuator (3200) and force release (3000), and outlet (3400), and an analyte detection membrane system receptacle (3300).

Figure 39:
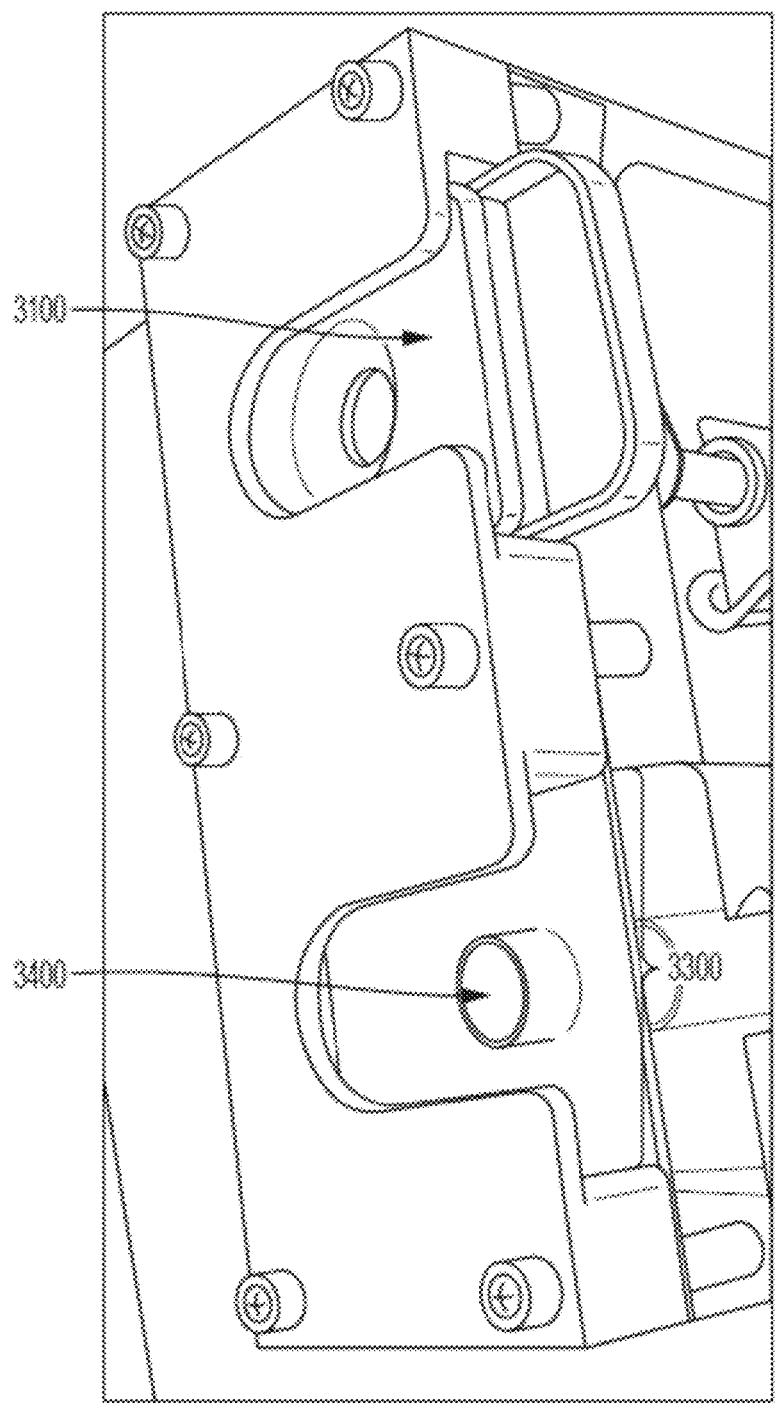
FIG. 39 depicts an enlarged view of a representative device according to some embodiments of the present invention.

FIG. 39 depicts, in part, an enlarged view of the outlet (3400), the receptacle (3300), and the cartridge (3100) depicted in FIG. 31.

Figure 40:
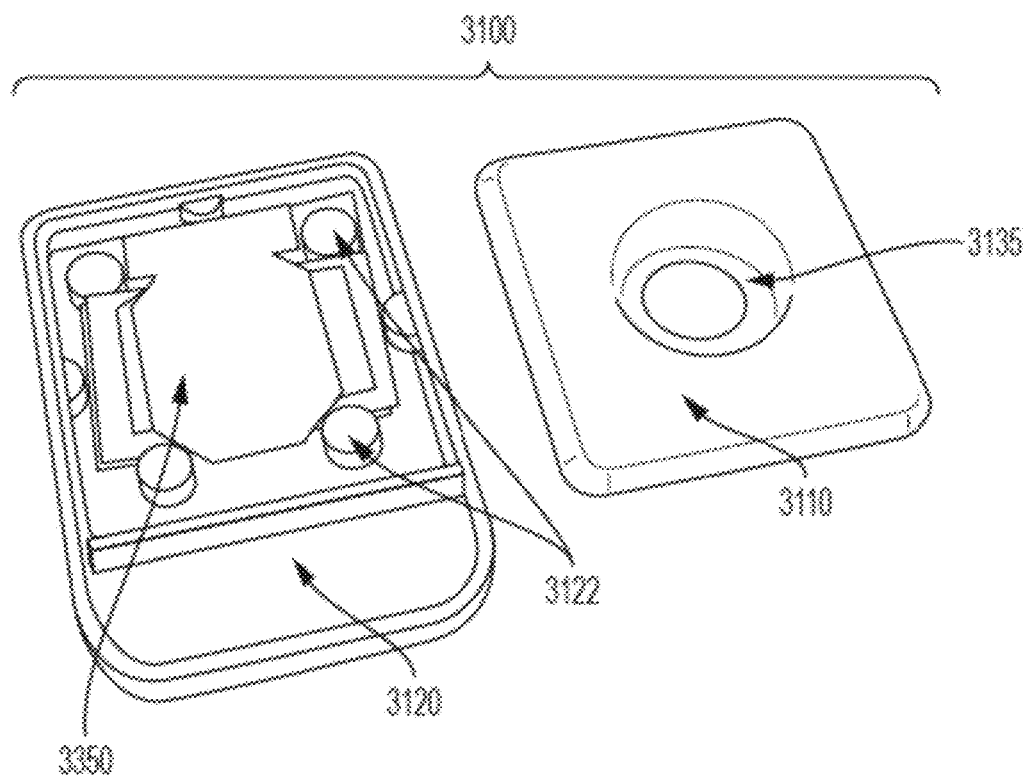
FIG. 40 depicts an exploded view of a cartridge and analyte detection membrane system according to some embodiments of the present invention.

FIG. 40 depicts, in part, an exploded view of a cartridge (3100) comprising a first housing member (3110), an inlet (3135), a conjugate pad (3350), a second housing member (3120), and a plurality of a membrane holders (3122).

Figure 41:
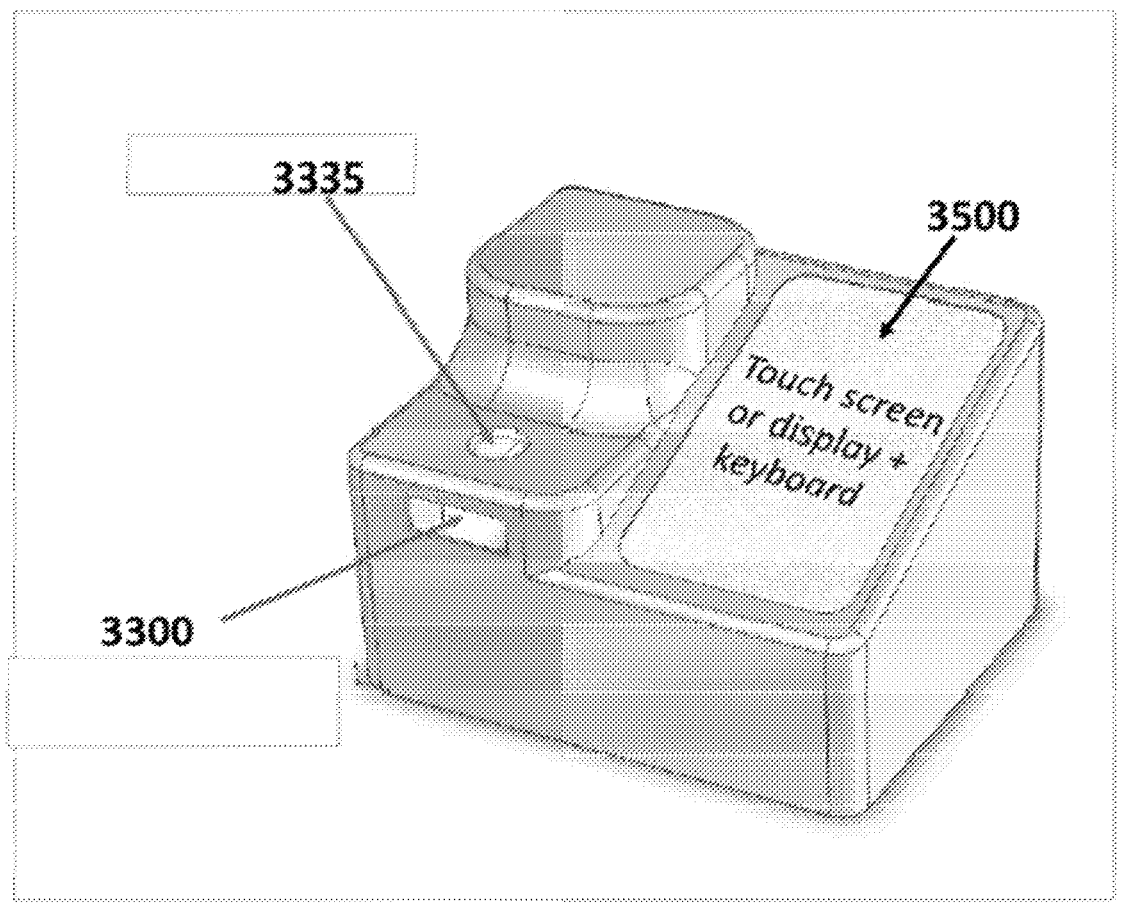
FIG. 41 depicts a representative device according to some embodiments of the present invention.

FIG. 41 depicts, in part, a device for detecting an analyte comprising an inlet (3335), a membrane system receptacle (3300), and display (3500).

Figure 42:
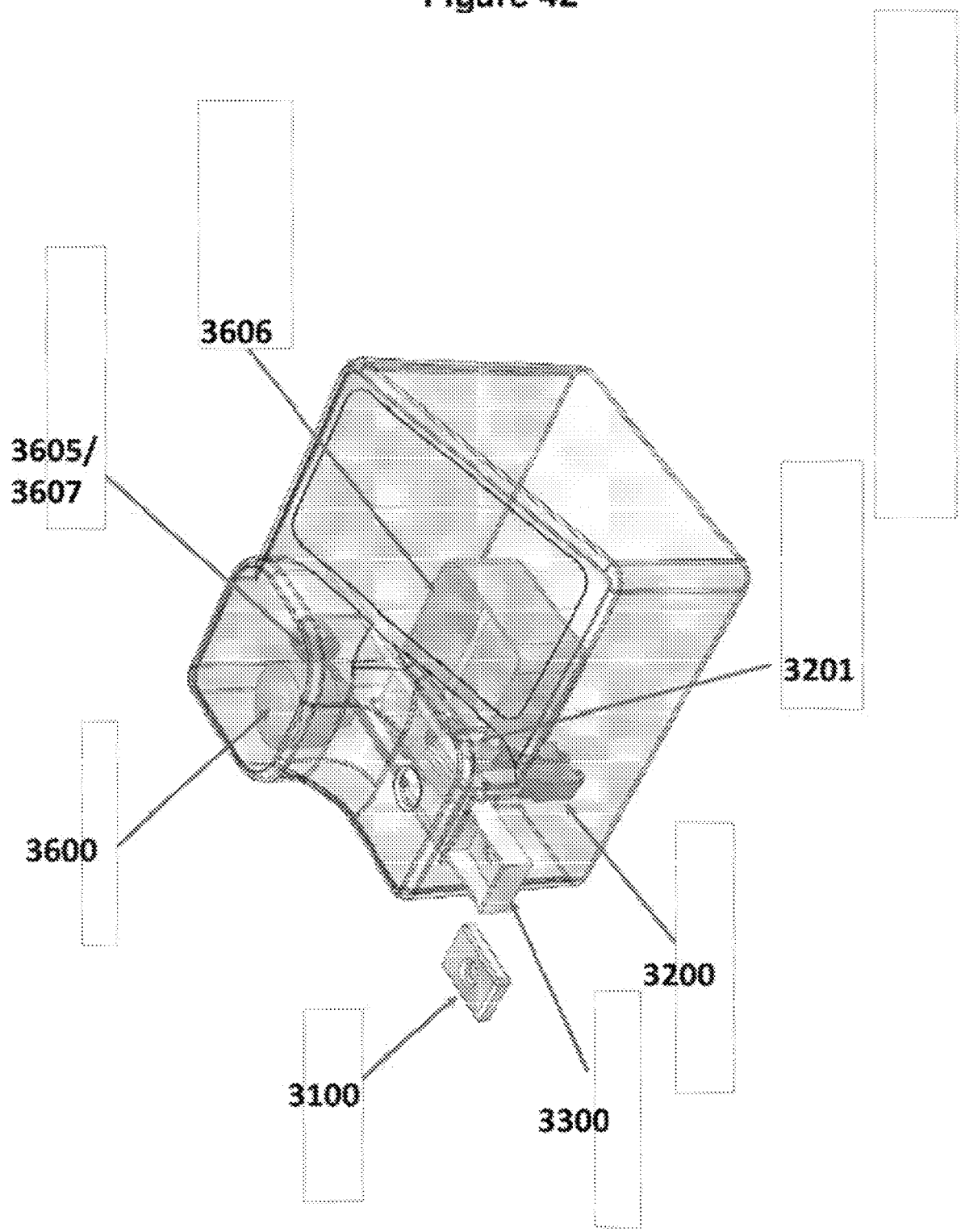
FIG. 42 depicts a representative device according to some embodiments of the present invention.

FIG. 42 depicts, in part, the interior of the device that can be used to detect multiple analytes with a single signal depicted in FIG. 41. The device comprises a cartridge comprising an analyte detection membrane system (3100), a membrane system receptacle (3300), a force actuator (3200), a spectrometer (e.g. optical reader or photodetector (3600), an optional conjugate pad remover (3201), an optional waste receptacle (3606), a motor and membrane system receptacle mover (3605/3607).

Figure 43:
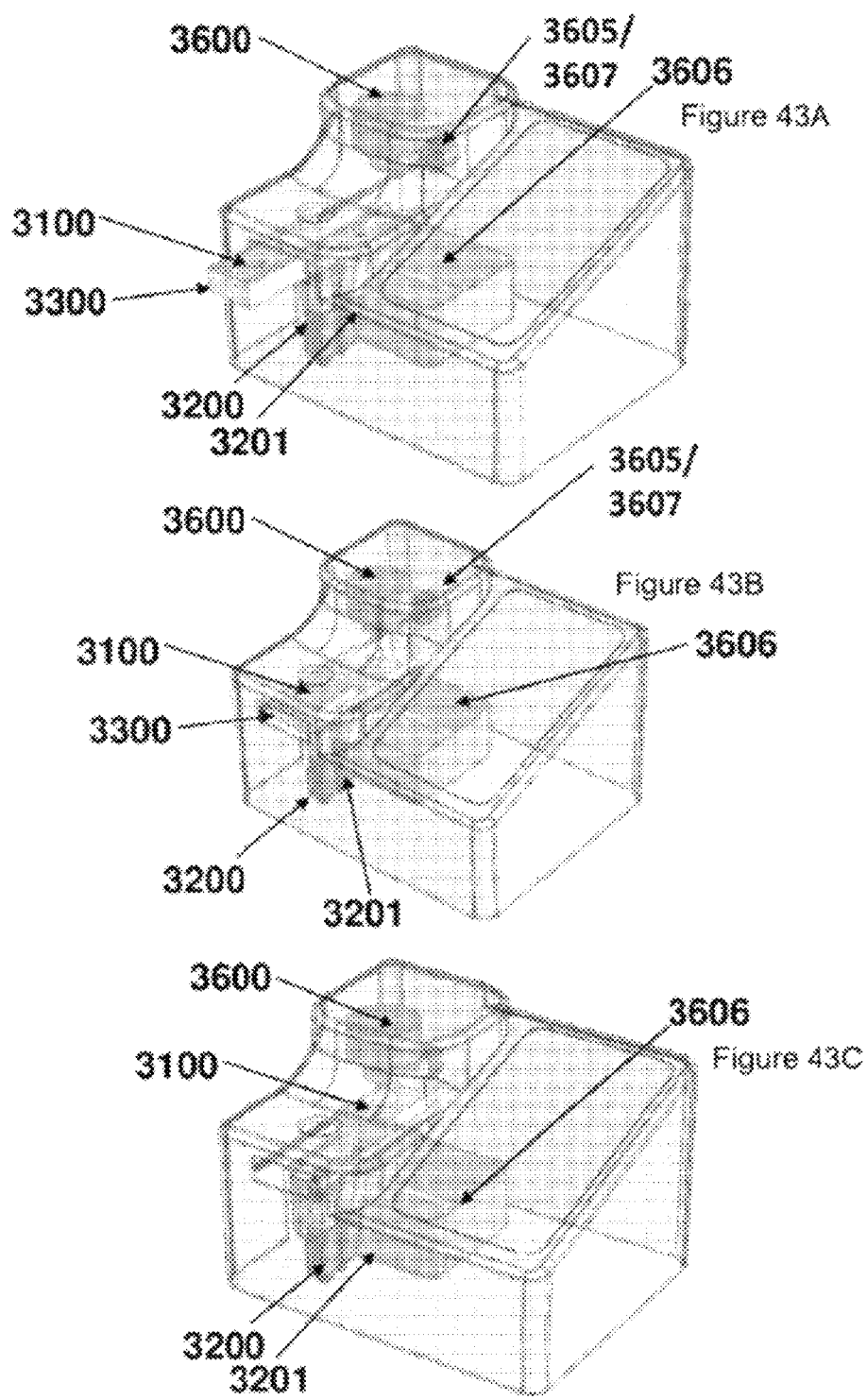
FIGS. 43A-43C depict a representative device according to some embodiments of the present invention.

FIG. 43, shows the interior of a device that can be used to detect multiple analytes with a single signal depicted in FIGS. 41 and 42 at various stages of use with the same components depicted in FIG. 35. FIG. 43A depict the cartridge being inserted into the receptacle. FIG. 43B depicts the receptacle holding the cartridge being moved beneath the inlet for sample application and FIG. 43C depicts the sample being analyzed by the spectrometer.

Figure 44:
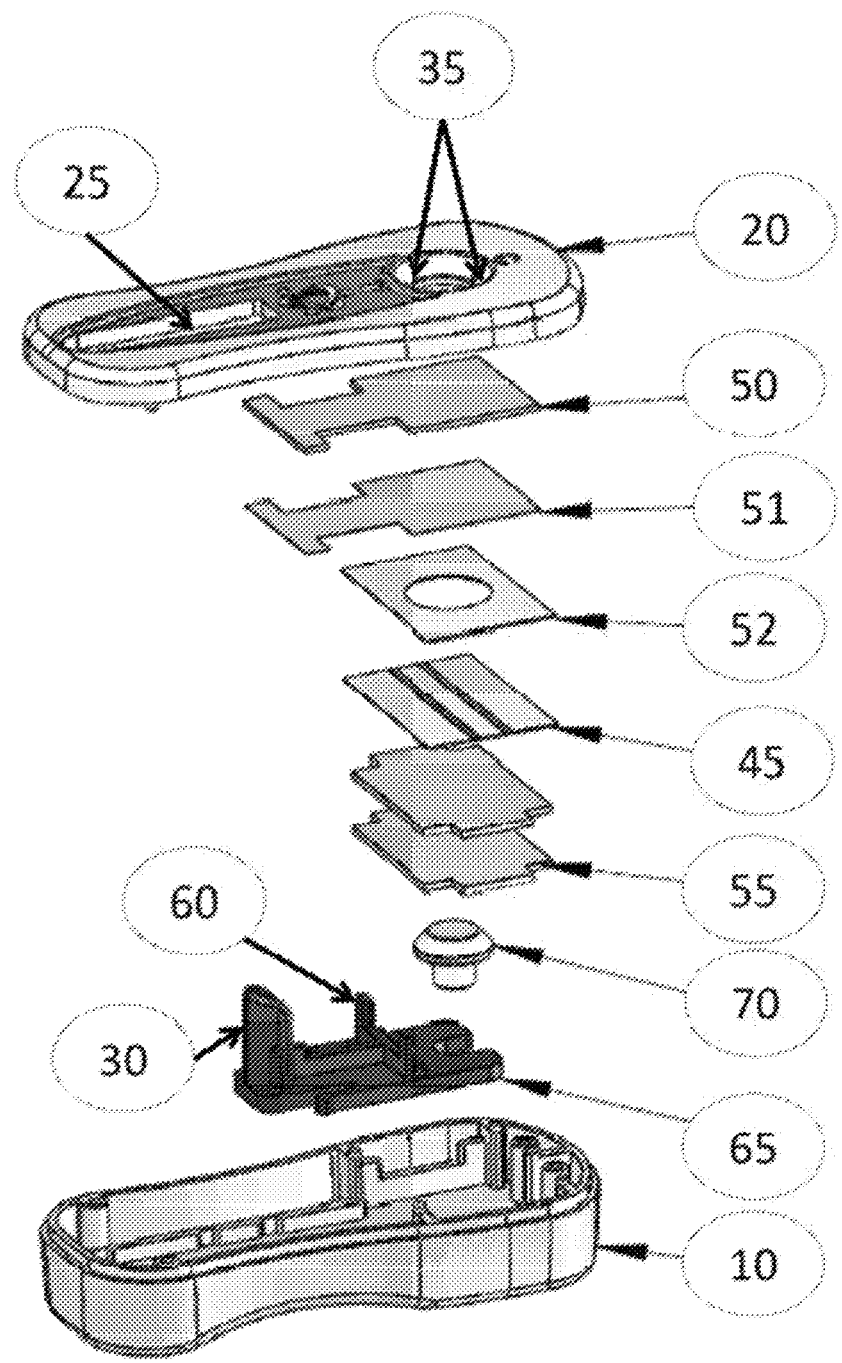
FIG. 44 depicts an exploded view of a representative device according to some embodiments of the present invention.

FIG. 44 depicts an exploded view of a device that can be used for the detection of a plurality of analytes with a single signal comprising a first housing member (10), a second housing member (20), a groove for the sliding button (25), a sliding button (30), an inlet opening (35), a test membrane (45), a conjugate pad (50), an additional membrane (51), an adhesive (52), a plurality of absorbent members (e.g. pads) (55), an attachment member (60), a locking member (65), and a force member (70). The components can be assembled as described and/or shown herein to make a device that can detect analytes using vertical flow.

Figure 45:
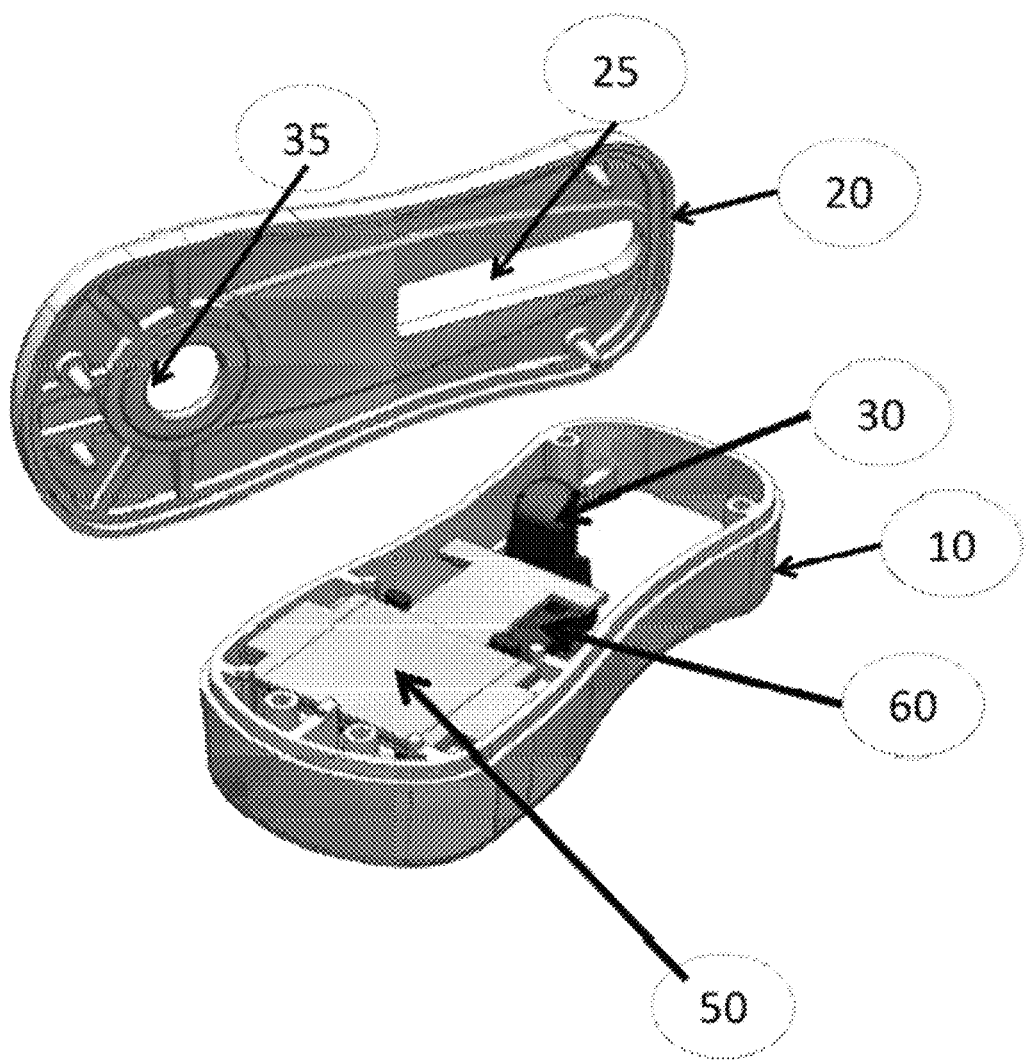
FIG. 45 depicts an exploded view of a representative device according to some embodiments of the present invention.

FIG. 45 depicts a partially exploded view of a device that can be used for the detection of a plurality of analytes with a single signal comprising a first housing member (10), a second housing member (20), a groove for the sliding button (25), a sliding button (30), an inlet opening (35), a test membrane not seen, a conjugate pad (50), a plurality of absorbent members (e.g. pads) (not shown), an attachment member (60), a locking member (not shown), and a force member (not shown). Other variations of this device can also be made and used in accordance with the methods described herein.

The embodiments are now described with reference to the following examples. These examples are provided for the purpose of illustration only and the embodiments should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1

Two separate PCR reactions were performed with Shiga toxin genes as the template that generated amplicons labeled with: 1) digoxigenin and biotin, and 2) FITC and biotin. The amplicons were then either mixed together in the presence or absence of streptavidin (bridge unit) or ran separately in a rapid flow through assay: Sample A) amplicon 1 alone, Sample B) amplicon 2 alone, or Sample C) amplicon 1+amplicon 2 with and without streptavidin. The flow through assay consisted of a solid support (nitrocellulose membrane) coated with anti-digoxigenin (first capture reagent) and colloidal gold particles coated with anti-FITC antibody. In this context, only Sample C with streptavidin generated a single positive test signal whereas Sample A and Sample B, or Sample C without streptavidin, resulted in a negative test.

Example 2: Detecting Multiple Analytes Using Amplicon Bridging Materials:

PCR reagents: OneTaq Hot Start Polymerase (New England Biolabs); 5× Standard Reaction buffer; Haptenated MHALT1.RV (Integrated DNA Technologies (IDT)); Haptenated MgC.CH1AS (IDT); INV018.7E4 $V_H$ gene template (ZG); dNTPs; $dH_2O$.

PCR was performed in a standard theremocycler at a ramp rate of 3-4° C./s. PCR reactions were run through a vertical flow assay such as those described herein including the Veriflow Cassette (Invisible Sentinel).

Amplicons were generated according to standard protocols. One amplicon was generated dual labeled with fluorescein isothiocyanate (FITC) and tetramethylrhodamine (TAMRA) and another amplicon was generated that is dual labeled with TAMRA and digoxigenin (DIG). The DNA amplicons from the PCR reaction can be optionally precipitated. If precipitation was performed, it was done by either by EtOH or Isopropanol+1/10 v Sodium Acetate 3M, pH 5.2 precipitation. To facilitate precipitation, 1 uL of tRNA glycogen can also be added. The precipitation was allowed to take place at −20° C. for a minimum of 2 hours or −80° C. for 15 mins. Precipitated DNA was centrifuged at top speed for about 15 minutes. Supernatant was discarded the DNA pellet was allowed to air dry 15 mins. An optional second rinse with 20 uL ICE cold 70% EtOH can be performed followed by centrifugation and drying. DNA pellet was suspended with TE (Tris-HCl/EDTA) and the DNA was allowed to rehydrate for about 24 hours at room temperature. The amplicons generated were generic sequences and not specific to any particular bacteria.

The amplicons were mixed with a biotinylated antibody recognizing FITC and an antibody that recognized rhodamine (i.e. the TAMRA label). The mixture can be incubated for longer period of times, e.g. 5, 10, 15, 20, 25, or 30 min, but such longer times were not necessary. The incubated mixture was added to a Veriflow Cassette (vertical flow device), which contained a test membrane comprising an unlabeled anti-digoxigenin antibody and a conjugate pad containing streptavidin-gold conjugate. The device detected the presence of the bridged complex, which contains both amplicons with a single signal (the colloidal gold). The appropriate controls were performed and the colloidal gold was only detected when all components necessary to create the bridging complex were present. Without wishing to be bound to any particular theory FIG. 3 illustrates the complex that can be formed with the different components. When bridging complex is formed (see, FIG. 3) the colloidal gold signal is detected. Other types of detectable signals can also be used. If one of the amplicons is not present no signal was detected. After the sample is run through the device the streptavidin-colloidal gold complex is released from the conjugate pad and the conjugate pad is removed. Examples of how to make and use the vertical flow devices can be found herein and in U.S. Pat. Nos. 8,012,770, 8,183,059 and U.S. patent application Ser. Nos. 13/500,997, 13/360,528, 13/445,233, each of which is hereby incorporated by reference in its entirety. These results demonstrate that two analytes can be specifically detected with a single detectable signal, which in this example was colloidal gold. The detection of the signal was not dependent upon precipitating the amplicons after performing the PCR reaction step.

The disclosures of each and every patent, patent application, publication, and accession number cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of determining the presence of a first analyte of interest and a second analyte of interest in a test sample comprising:
reacting the test sample with a first set of primers that are specific to the first analyte of interest and a second set of primers that are specific to the second analyte of interest under conditions to produce a reaction mixture, the reaction mixture comprising first analyte of interest amplification products and second analyte of interest amplification products when the first analyte of interest and the second analyte of interest are present in the test sample;
wherein the first analyte of interest amplification products comprise a first interaction unit that binds to a first capture reagent and a second interaction unit that binds to a bridge unit;
wherein the second analyte of interest amplification products comprise a first interaction unit that binds to the bridge unit and a second interaction unit;
wherein the bridge unit comprises a second capture reagent;
contacting a solid support comprising the first capture reagent affixed to the solid support with the reaction mixture, the bridge unit, and a signal detection unit comprising a third capture reagent; and
detecting the presence or absence of the signal detection unit which determines the presence or absence of the first analyte of interest and second analyte of interest concurrently, wherein:
the signal detection unit that binds to: i) the second analyte, ii) to the second analyte's first interaction unit or second interaction unit, iii) to a component of the first and second analyte complex, or iv) a component of an analyte-bridge complex that is only present when the complex contains the first and second analytes.

2. The method of claim 1, wherein the solid support is an agarose, sepharose, polyacrylamide, agarose/polyacrylamide co-polymers, dextran, cellulose, polypropylene, polycarbonate, nitrocellulose, or glass paper solid support.

3. The method of claim 1, wherein the first and second interaction unit of the first analyte of interest and the first and second interaction unit of the second analyte of interest are each, independently, a heterologous interaction unit.

4. The method of claim 1, wherein the second interaction unit of the first analyte of interest and the first interaction unit of the second analyte of interest comprise the same heterologous interaction unit.

5. The method of claim 3, wherein the first interaction unit of the first analyte of interest and the second interaction unit of the second analyte of interest comprise the same heterologous interaction unit.

6. The method of claim 1, wherein the first and second analytes of interest are, independently, an amplification product, a peptide, a sugar, an antigen, a nucleic acid molecule, or any combination thereof.

7. The method of claim 1, wherein the bridge unit is a multivalent capture reagent.

8. The method of claim 7, wherein the bridge unit is an immunoglobulin molecule.

9. The method of claim 1, wherein the signal detection unit comprises a radioactive tag, colloidal gold, a fluorescent tag, a nanoparticle, an emissive nanoparticle, a quantum dot, a magnetic particle, or an enzyme.

10. A method of determining the presence of a first analyte of interest, a second analyte of interest, and a third analyte of interest in a test sample comprising:
reacting the test sample with a first set of primers that are specific to the first analyte of interest, a second set of primers that are specific to the second analyte of interest, and a third set of primers that are specific to the third analyte of interest under conditions to produce a reaction mixture, the reaction mixture comprising first analyte of interest amplification products, second analyte of interest amplification products, and third analyte of interest amplification products when the first analyte of interest, the second analyte of interest, and third analyte of interest are present in the test sample;
wherein the first analyte of interest amplification products comprise a first interaction unit that binds to a first capture reagent and a second interaction unit that binds to a first bridge unit;
wherein the second analyte of interest amplification products comprise a first interaction unit that binds to the first bridge unit and a second interaction unit that bind to a second bridge unit;
wherein the third analyte of interest amplification products comprise a first interaction unit that bind to the second bridge unit and a second interaction unit;
wherein the first bridge unit comprises a second capture reagent;
wherein the second bridge unit comprises a third capture reagent;
contacting a solid support comprising the first capture reagent affixed to the solid support with the reaction mixture, the bridge unit, and a signal detection unit comprising a fourth capture reagent; and
detecting the presence or absence of the signal detection unit which determines the presence or absence of the first analyte of interest and second analyte of interest concurrently, wherein:
the signal detection unit that binds to: i) the third analyte, ii) to the third analyte's first interaction unit or second interaction unit, iii) to a component of the first, second, and third analyte complex, or iv) a component of an analyte-bridge complex that is only present when the complex contains the first, second, and third analytes.

11. The method of claim 10, wherein the solid support is an agarose, sepharose, polyacrylamide, agarose/polyacrylamide co-polymers, dextran, cellulose, polypropylene, polycarbonate, nitrocellulose, or glass paper solid support.

12. The method of claim 10, wherein the first and second interaction unit of the first analyte of interest the first and second interaction unit of the second analyte of interest, and the first and second interaction unit of the third analyte of interest are each, independently, a heterologous interaction unit.

13. The method of claim 10, wherein the second interaction unit of the first analyte of interest and the first interaction unit of the second analyte of interest comprise the same heterologous interaction unit.

14. The method of claim 13, wherein the first interaction unit of the first analyte of interest and the second interaction unit of the second analyte of interest comprise the same heterologous interaction unit.

15. The method of claim 10, wherein the second interaction unit of the second analyte of interest and the first interaction unit of the third analyte of interest comprise the same heterologous interaction unit.

16. The method of claim 15, wherein the first interaction unit of the second analyte of interest and the second interaction unit of the third analyte of interest comprise the same heterologous interaction unit.

17. The method of claim 10, wherein the first, second, and third analytes of interest are, independently, an amplification product, a peptide, a sugar, an antigen, a nucleic acid molecule, or any combination thereof.

18. The method of claim 10, wherein the first and second bridge units are each multivalent capture reagents.

19. The method of claim 18, wherein the first and second bridge units are immunoglobulin molecules.

20. The method of claim 10, wherein the signal detection unit comprises a radioactive tag, colloidal gold, a fluorescent tag, a nanoparticle, an emissive nanoparticle, a quantum dot, a magnetic particle, or an enzyme.

* * * * *